United States Patent
Knapp et al.

(10) Patent No.: US 8,273,928 B2
(45) Date of Patent: Sep. 25, 2012

(54) PROCESSES FOR SEPARATION OF FLUOROOLEFINS FROM HYDROGEN FLUORIDE BY AZEOTROPIC DISTILLATION

(75) Inventors: Jeffrey P. Knapp, Wilmington, DE (US); Barry Asher Mahler, Glen Mills, PA (US); Donald J. Toton, New Castle, DE (US)

(73) Assignee: E I Du Pont de Nemours and Company, Wilmington, DE (US)

( * ) Notice: Subject to any disclaimer, the term of this patent is extended or adjusted under 35 U.S.C. 154(b) by 769 days.

(21) Appl. No.: 11/844,403

(22) Filed: Aug. 24, 2007

(65) Prior Publication Data

US 2008/0051612 A1    Feb. 28, 2008

Related U.S. Application Data

(60) Provisional application No. 60/839,737, filed on Aug. 24, 2006.

(51) Int. Cl.
*C07C 21/18* (2006.01)
(52) U.S. Cl. .......................... 570/136; 570/134; 570/135
(58) Field of Classification Search .......................... None
See application file for complete search history.

(56) References Cited

U.S. PATENT DOCUMENTS

| | | | |
|---|---|---|---|
| 2,831,902 A | 4/1958 | Hamilton et al. | |
| 3,947,558 A * | 3/1976 | van Eijl | 423/483 |
| 5,396,000 A | 3/1995 | Nappa et al. | |
| 5,679,875 A | 10/1997 | Aoyama et al. | |
| 6,031,141 A | 2/2000 | Mallikarjuna et al. | |
| 6,303,838 B1 | 10/2001 | Boehmer et al. | |
| 6,369,284 B1 | 4/2002 | Nappa et al. | |
| 2003/0028057 A1 | 2/2003 | Owens et al. | |
| 2006/0116538 A1* | 6/2006 | Miller et al. | 570/178 |
| 2007/0099811 A1 | 5/2007 | Miller et al. | |
| 2007/0100173 A1 | 5/2007 | Miller et al. | |
| 2007/0100174 A1 | 5/2007 | Miller et al. | |
| 2007/0100175 A1 | 5/2007 | Miller et al. | |
| 2007/0100176 A1 | 5/2007 | Miller et al. | |

FOREIGN PATENT DOCUMENTS

| | | |
|---|---|---|
| EP | 0 940 382 B1 | 9/1999 |
| WO | WO 99/20585 | 4/1999 |
| WO | WO 99/26907 | 6/1999 |
| WO | WO 99/26908 | 6/1999 |

OTHER PUBLICATIONS

Jeanneaux et al., "Addition Thermique Des IODO-1-Perfluoroalcanes Sur Les Perfluoroalkylethylenes", Journal of Fluorine Chemistry, 4, (1974), pp. 261-270.
PCT International Search Report for International Application No. PCT/US2007/018837 dated Dec. 14, 2007.

* cited by examiner

*Primary Examiner* — Karl J Puttlitz

(57) ABSTRACT

The present disclosure relates to a process for separating a fluoroolefin from a mixture comprising hydrogen fluoride and fluoroolefin, comprising azeotropic distillation both with and without an entrainer. In particular are disclosed processes for separating any of HFC-1225ye, HFC-1234ze, HFC-1234yf or HFC-1243zf from HF.

12 Claims, 8 Drawing Sheets

PROCESSES FOR SEPARATION OF FLUOROOLEFINS FROM HYDROGEN FLUORIDE BY AZEOTROPIC DISTILLATION

CROSS REFERENCE(S) TO RELATED APPLICATION(S)

This application claims the priority benefit of U.S. Provisional Application No. 60/839,737, filed Aug. 24, 2006.

BACKGROUND INFORMATION

1. Field of the Disclosure

This disclosure relates in general to processes for separating HF from fluoroolefins.

2. Description of the Related Art

The chemical manufacture of fluoroolefins may produce mixtures of the desired fluoroolefins and hydrogen fluoride (HF). The separation of fluoroolefins and HF is not always easily accomplished. Existing methods of distillation and decantation are very often ineffective for separation of these compounds. Aqueous scrubbing may be effective, but requires the use of large amounts of scrubbing solutions and produces excessive waste as well as wet product that must then be dried. Therefore, there is a need for new methods of separating HF from fluoroolefins.

SUMMARY

The present disclosure provides a process for separating a mixture comprising HF and fluoroolefin, said process comprising: a) feeding the composition comprising HF and fluoroolefin to a first distillation column; b) removing an azeotrope composition comprising HF and fluoroolefin as a first distillate and either i) HF or ii) fluoroolefin as a first column bottoms composition; c) condensing the first distillate to form two liquid phases, being i) an HF-rich phase and ii) a fluoroolefin-rich phase; and d) recycling a first liquid phase enriched in the same compound that is removed as the first column bottoms, said first liquid phase being either i) HF-rich phase or ii) fluoroolefin-rich phase, back to the first distillation column.

Also disclosed is a process for separating a fluoroolefin from a mixture comprising hydrogen fluoride and said fluoroolefin, wherein said fluoroolefin is present in a concentration greater than the azeotrope concentration for hydrogen fluoride and said fluoroolefin, said process comprising: a) feeding said mixture comprising hydrogen fluoride and said fluoroolefin to a first distillation column; b) removing an azeotrope composition comprising hydrogen fluoride and fluoroolefin as a first distillate from the first distillation column; c) recovering fluoroolefin essentially free of hydrogen fluoride as a first bottoms composition from the first distillation column; d) condensing the first distillate to form two liquid phases, being i) a hydrogen fluoride-rich phase and ii) a fluoroolefin-rich phase; and e) recycling the fluoroolefin-rich phase to the first distillation column.

Also provided is a process for separating hydrogen fluoride from a mixture comprising hydrogen fluoride and a fluoroolefin, wherein hydrogen fluoride is present in a concentration greater than the azeotrope concentration for hydrogen fluoride and said fluoroolefin, said process comprising: a) feeding said mixture comprising hydrogen fluoride and fluoroolefin to a first distillation column; b) removing an azeotrope or azeotrope-like composition comprising fluoroolefin and HF as a first distillate from the first distillation column; c) recovering hydrogen fluoride essentially free of fluoroolefin as a first bottoms composition from the first distillation column; d) condensing the first distillate to form two liquid phases, being a fluoroolefin-rich phase and a hydrogen fluoride-rich phase; and e) recycling the HF-rich phase to the first distillation column.

Also provided is a process for the purification of a fluoroolefin from a mixture comprising fluoroolefin and HF, wherein said fluoroolefin is present in said mixture in a concentration greater than the azeotrope concentration for said fluoroolefin and HF, said process comprising: a) adding an entrainer to the mixture comprising fluoroolefin and HF thus forming a second mixture; b) distilling said second mixture in a first distillation step to form a first distillate composition comprising HF, fluoroolefin, and entrainer, and a first bottoms composition comprising fluoroolefin; c) condensing said first distillate composition to form two liquid phases, being i) an HF-rich phase and ii) an entrainer-rich phase; and d) optionally recycling the fluoroolefin-rich phase back to the first distillation step.

Also provided is a process for the purification of HF from a mixture comprising a fluoroolefin and HF, wherein HF is present in a concentration greater than the azeotrope concentration for HF and said fluoroolefin, said process comprising: a) adding an entrainer to the mixture comprising fluoroolefin and HF thus forming a second mixture; b) distilling said second mixture in a first distillation step to form a first distillate composition comprising HF, entrainer, and fluoroolefin, and a first bottoms composition comprising HF; c) condensing said first distillate composition to form two liquid phases, being i) an entrainer-rich phase and ii) an HF-rich phase; and d) optionally recycling the HF-rich phase back to the first distillation step.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
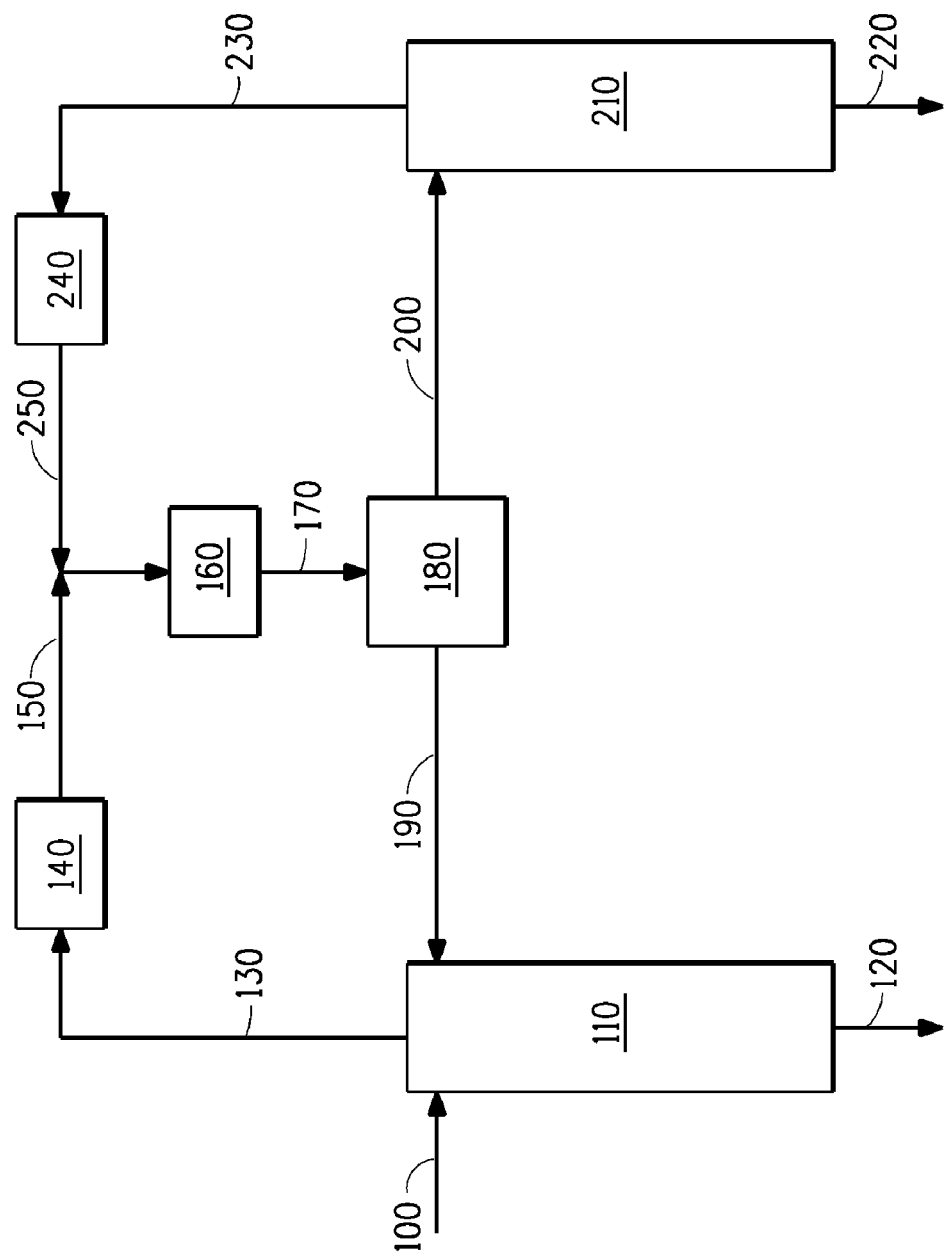
FIG. 1 is an illustration of one embodiment of an azeotropic distillation for the separation of HF and a fluoroolefin with no added entrainer.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

1. Definitions and Clarification of Terms

Before addressing details of embodiments described below, some terms are defined or clarified.

By azeotropic or azeotrope composition is meant a constant-boiling mixture of two or more substances that boils at a constant composition and thus behaves as a single substance. Constant-boiling compositions are characterized as azeotropic because they exhibit either a maximum or minimum boiling point, when compared with the boiling points of the individual components. Azeotropic compositions are also characterized by a minimum or a maximum in the vapor pressure measurements relative to the vapor pressure of the neat components in a PTx cell as a function of composition at a constant temperature. For homogenous azeotropes, where the vapor phase is in equilibrium with a single liquid phase, the compositions of the vapor and liquid phases are identical. However, for heterogeneous azeotropes, where the vapor phase is in equilibrium with two liquid phases, all three equilibrium phases can have different, but constant, compositions.

As used herein, the term "azeotrope-like composition" (also commonly referred to as a "near azeotropic composition") means a constant boiling, or substantially constant boiling liquid admixture of two or more substances that behaves as a single substance. One way to characterize an azeotrope-like composition is that the composition of the vapor produced by partial evaporation or distillation of the liquid does not change substantially throughout the partial evaporation or distillation. Similarly, the composition of the liquid phase or phases present does not change substantially during the partial evaporation or distillation. That is, the admixture boils/distills/refluxes without substantial composition change. This is to be contrasted with non-azeotrope-like compositions in which the liquid composition changes to a substantial degree during boiling or evaporation. Another way to characterize an azeotrope-like composition is that the bubble point vapor pressure of the composition and the dew point vapor pressure of the composition at a particular temperature are substantially the same. Herein, a composition is considered to be azeotrope-like if the difference in dew point pressure and bubble point pressure is less than or equal to 3 percent (based upon the bubble point pressure).

By high-boiling azeotrope is meant that an azeotropic or azeotrope-like composition boils at a higher temperature at any given pressure than any one of the compounds that comprise it would separately boil at that pressure. Alternately, by high-boiling azeotrope is meant any azeotropic or azeotrope-like composition that has a lower vapor pressure at any given temperature than any one of the compounds that comprise it would separately have at that temperature.

By low-boiling-azeotrope is meant that an azeotropic or azeotrope-like composition boils at a lower temperature at any given pressure than any one of the compounds that comprise it would separately boil at that pressure. Alternately, by low-boiling azeotrope is meant any azeotropic or azeotrope-like composition that has a higher vapor pressure at any given temperature than the vapor pressure of any one of the compounds that comprise the azeotrope would separately have at that temperature.

It is possible to characterize an azeotropic or azeotrope-like composition as a substantially constant-boiling admixture that may appear under many guises, depending upon the conditions chosen, by several criteria:

The composition can be defined as an azeotrope of two compounds because the term "azeotrope" is at once both definitive and limitative, and requires effective amounts of those two or more compounds for this unique composition of matter which can be a constant-boiling composition.

It is well known by those skilled in the art, that, at different pressures, the composition of a given azeotrope or azeotrope-like composition will vary at least to some degree, as will the boiling point temperature. Thus, an azeotropic or azeotrope-like composition of two compounds represents a unique type of relationship but with a variable composition which depends on temperature and/or pressure. Therefore, compositional ranges, rather than fixed compositions, are often used to define azeotropes and azeotrope-like compositions.

An azeotrope or azeotrope-like composition of two compounds can be characterized by defining compositions characterized by a boiling point at a given pressure, thus giving identifying characteristics without unduly limiting the scope of the invention by a specific numerical composition, which is limited by and is only accurate as the analytical equipment available.

It is recognized in the art that both the boiling point and the weight (or mole) percentages of each component of the azeotropic composition may change when the azeotrope or azeotrope-like liquid composition is allowed to boil at different pressures. Thus, an azeotropic or an azeotrope-like composition may be defined in terms of the unique relationship that exists among components or in terms of the exact weight (or mole) percentages of each component of the composition characterized by a fixed boiling point at a specific pressure.

As used herein, the term "azeotrope" is meant to refer to azeotrope compositions and/or azeotrope-like compositions.

By entrainer is meant any compound that, when added to a first mixture, forms one or more azeotropes with the components of the mixture to facilitate separation of the components of the mixture. As used herein, the terms "entrainer" and "entraining agent" are used interchangeably and are to be interpreted as having identical meaning.

The process equipment for all the processes disclosed herein and the associated feed lines, effluent lines and associated units may be constructed of materials resistant to hydrogen fluoride. Typical materials of construction, well-known to the art, include stainless steels, in particular of the austenitic type, and the well-known high nickel alloys such as Monel® nickel-copper alloys, Hastelloy® nickel based alloys and Inconel® nickel-chromium alloys.

By azeotropic distillation is meant a process in which a distillation column is operated under conditions to cause one or more azeotropic or azeotrope-like composition to form, and thereby facilitates the separation of the components of the mixture. Azeotropic distillations may occur where only the components of the mixture to be separated are distilled, or where an entrainer is added that forms an azeotrope with one or more of the components of the initial mixture. Entrainers that act in this manner, that is to say, that form an azeotrope with one of more of the components of the mixture to be separated thus facilitating the separation of those components by distillation, are more commonly called azeotroping agents or azeotropic entrainers.

In conventional or azeotropic distillations, the overhead or distillate stream exiting the column may be condensed using conventional reflux condensers. At least a portion of this condensed stream can be returned to the top of the column as reflux, and the remainder recovered as product or for optional processing. The ratio of the condensed material which is returned to the top of the column as reflux to the material removed as distillate is commonly referred to as the reflux ratio. The compounds and entrainer exiting the column as distillate or distillation bottoms stream can then be passed to a stripper or second distillation column for separation by using conventional distillation, or may be separated by other methods, such as decantation. If desired, the entrainer may then be recycled back to the first distillation column for reuse.

The specific conditions which can be used for practicing the invention depend upon a number of parameters, such as the diameter of the distillation column, feed points, number of separation stages in the column, among others. In one embodiment, the operating pressure of the distillation system may range from about 5 to 500 psia, in another embodiment, about 20 to 400 psia. Normally, increasing the reflux ratio results in increased distillate stream purity, but generally the reflux ratio ranges between 1/1 to 200/1. The temperature of the condenser, which is located adjacent to the top of the column, is normally sufficient to substantially fully condense the distillate that is exiting from the top of the column, or is that temperature required to achieve the desired reflux ratio by partial condensation.

The problems associated with conventional distillation can be solved by a distillation process using entrainers. The difficulty in applying this method is that there is no known way, short of experimentation, of predicting which if any compound will be an effective entrainer.

As used herein, by "essentially free of" is meant that a composition contains less than about 100 ppm (mole basis), less than about 10 ppm or less than about 1 ppm, of the specified component. If a composition is essentially free of more than one component, then the total concentration of those components is less than about 100 ppm, less than about 10 ppm, or less than about 1 ppm.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

Hydrogen fluoride (HF, anhydrous) is a commercially available chemical or can be produced by methods known in the art.

The term "fluoroolefin" is intended to mean a compound comprising carbon and fluorine and optionally hydrogen that additionally comprises at least one double bond.

In one embodiment, fluoroolefins comprise compounds with 2 to 12 carbon atoms, in another embodiment the fluoroolefins comprise compounds with 3 to 10 carbon atoms, and in yet another embodiment the fluoroolefins comprise compounds with 3 to 7 carbon atoms. Representative fluoroolefins include but are not limited to all compounds as listed in Table 1, Table 2, and Table 3.

The present invention provides fluoroolefins having the formula E- or Z—$R^1CH=CHR^2$ (Formula I), wherein $R^1$ and $R^2$ are, independently, $C_1$ to $C_6$ perfluoroalkyl groups. Examples of $R^1$ and $R^2$ groups include, but are not limited to, $CF_3$, $C_2F_5$, $CF_2CF_2CF_3$, $CF(CF_3)_2$, $CF_2CF_2CF_2CF_3$, $CF(CF_3)CF_2CF_3$, $CF_2CF(CF_3)_2$, $C(CF_3)_3$, $CF_2CF_2CF_2CF_2CF_3$, $CF_2CF_2CF(CF_3)_2$, $C(CF_3)_2C_2F_5$, $CF_2CF_2CF_2CF_2CF_2CF_3$, $CF(CF_3)CF_2CF_2C_2F_5$, and $C(CF_3)_2CF_2C_2F_5$. In one embodiment the fluoroolefins of Formula I, have at least about 4 carbon atoms in the molecule. In another embodiment, the fluoroolefins of Formula I have at least about 5 carbon atoms in the molecule. Exemplary, non-limiting Formula I compounds are presented in Table 1.

TABLE 1

| Code | Structure | Chemical Name |
|---|---|---|
| F11E | $CF_3CH=CHCF_3$ | 1,1,1,4,4,4-hexafluorobut-2-ene |
| F12E | $CF_3CH=CHC_2F_5$ | 1,1,1,4,4,5,5,5-octafluoropent-2-ene |
| F13E | $CF_3CH=CHCF_2C_2F_5$ | 1,1,1,4,4,5,5,6,6,6-decafluorohex-2-ene |
| F13iE | $CF_3CH=CHCF(CF_3)_2$ | 1,1,1,4,5,5,5-heptafluoro-4-(trifluoromethyl)pent-2-ene |
| F22E | $C_2F_5CH=CHC_2F_5$ | 1,1,1,2,2,5,5,6,6,6-decafluorohex-3-ene |
| F14E | $CF_3CH=CH(CF_2)_3CF_3$ | 1,1,1,4,4,5,5,6,6,7,7,7-dodecafluorohept-2-ene |
| F14iE | $CF_3CH=CHCF_2CF-(CF_3)_2$ | 1,1,1,4,4,5,5,6,6,6-nonafluoro-5-(trifluoromethyl)hex-2-ene |
| F14sE | $CF_3CH=CHCF(CF_3)-C_2F_5$ | 1,1,1,4,5,5,6,6,6-nonfluoro-4-(trifluoromethyl)hex-2-ene |
| F14tE | $CF_3CH=CHC(CF_3)_3$ | 1,1,1,5,5,5-hexafluoro-4,4-bis(trifluoromethyl)pent-2-ene |
| F23E | $C_2F_5CH=CHCF_2C_2F_5$ | 1,1,1,2,2,5,5,6,6,7,7,7-dodecafluorohept-3-ene |
| F23iE | $C_2F_5CH=CHCF(CF_3)_2$ | 1,1,1,2,2,5,5,6,6,6-nonafluoro-5-(trifluoromethyl)hex-3-ene |
| F15E | $CF_3CH=CH(CF_2)_4CF_3$ | 1,1,1,4,4,5,5,6,6,7,7,8,8,8-tetradecafluorooct-2-ene |
| F15iE | $CF_3CH=CH-CF_2CF_2CF(CF_3)_2$ | 1,1,1,4,4,5,5,6,7,7,7-undecafluoro-6-(trifluoromethyl)hept-2-ene |
| F15tE | $CF_3CH=CH-C(CF_3)_2C_2F_5$ | 1,1,1,5,5,6,6,6-octafluoro-4,4-bis(trifluoromethyl)hex-2-ene |
| F24E | $C_2F_5CH=CH(CF_2)_3CF_3$ | 1,1,1,2,2,5,5,6,6,7,7,8,8,8-tetradecafluorooct-3-ene |
| F24iE | $C_2F_5CH=CHCF_2CF-(CF_3)_2$ | 1,1,1,2,2,5,5,6,7,7,7-undecafluoro-6-(trifluoromethyl)hept-3-ene |
| F24sE | $C_2F_5CH=CHCF(CF_3)-C_2F_5$ | 1,1,1,2,2,5,5,6,6,7,7,7-undecafluoro-5-(trifluoromethyl)hept-3-ene |
| F24tE | $C_2F_5CH=CHC(CF_3)_3$ | 1,1,1,2,2,6,6,6-octafluoro-5,5-bis(trifluoromethyl)hex-3-ene |
| F33E | $C_2F_5CF_2CH=CH-CF_2C_2F_5$ | 1,1,1,2,2,3,3,6,6,7,7,8,8,8-tetradecafluorooct-4-ene |
| F3i3iE | $(CF_3)_2CFCH=CH-CF(CF_3)_2$ | 1,1,1,2,5,6,6,6-octafluoro-2,5-bis(trifluoromethyl)hex-3-ene |
| F33iE | $C_2F_5CF_2CH=CH-CF(CF_3)_2$ | 1,1,1,2,5,5,6,6,7,7,7-undecafluoro-2-(trifluoromethyl)hept-3-ene |
| F16E | $CF_3CH=CH(CF_2)_5CF_3$ | 1,1,1,4,4,5,5,6,6,7,7,8,8,,9,9,9-hexadecafluoronon-2-ene |
| F16sE | $CF_3CH=CHCF(CF_3)(CF_2)_2C_2F_5$ | 1,1,1,4,5,5,6,6,7,7,8,8,8-tridecafluoro-4-(trifluoromethyl)hept-2-ene |
| F16tE | $CF_3CH=CHC(CF_3)_2CF_2C_2F_5$ | 1,1,1,6,6,6-octafluoro-4,4-bis(trifluoromethyl)hept-2-ene |
| F25E | $C_2F_5CH=CH(CF_2)_4CF_3$ | 1,1,1,2,2,5,5,6,6,7,7,8,8,9,9,9-hexadecafluoronon-3-ene |
| F25iE | $C_2F_5CH=CH-CF_2CF_2CF(CF_3)_2$ | 1,1,1,2,2,5,5,6,6,7,8,8,8-tridecafluoro-7-(trifluoromethyl)oct-3-ene |
| F25tE | $C_2F_5CH=CH-C(CF_3)_2C_2F_5$ | 1,1,1,2,2,6,6,7,7,7-decafluoro-5,5-bis(trifluoromethyl)hept-3-ene |
| F34E | $C_2F_5CF_2CH=CH-(CF_2)_3CF_3$ | 1,1,1,2,2,3,3,6,6,7,7,8,8,9,9,9-hexadecafluoronon-4-ene |
| F34iE | $C_2F_5CF_2CH=CH-CF_2CF(CF_3)_2$ | 1,1,1,2,2,3,3,6,6,7,8,8,8-tridecafluoro-7-(trifluoromethyl)oct-4-ene |
| F34sE | $C_2F_5CF_2CH=CH-CF(CF_3)C_2F_5$ | 1,1,1,2,2,3,3,6,7,7,8,8,8-tridecafluoro-6-(trifluoromethyl)oct-4-ene |
| F34tE | $C_2F_5CF_2CH=CH-C(CF_3)_3$ | 1,1,1,5,5,6,6,7,7,7-decafluoro-2,2-bis(trifluoromethyl)hept-3-ene |
| F3i4E | $(CF_3)_2CFCH=CH-(CF_2)_3CF_3$ | 1,1,1,2,5,5,6,6,7,7,8,8,8-tridecafluoro-2(trifluoromethyl)oct-3-ene |
| F3i4iE | $(CF_3)_2CFCH=CH-CF_2CF(CF_3)_2$ | 1,1,1,2,5,5,6,7,7,7-decafluoro-2,6-bis(trifluoromethyl)hept-3-ene |
| F3i4sE | $(CF_3)_2CFCH=CH-CF(CF_3)C_2F_5$ | 1,1,1,2,5,5,6,7,7,7-decafluoro-2,5-bis(trifluoromethyl)hept-3-ene |
| F3i4tE | $(CF_3)_2CFCH=CH-C(CF_3)_3$ | 1,1,1,2,6,6,6-heptafluoro-2,5,5-tris(trifluoromethyl)hex-3-ene |
| F26E | $C_2F_5CH=CH(CF_2)_5CF_3$ | 1,1,1,2,2,5,5,6,6,7,7,8,8,9,9,10,10,10-octadecafluorodec-3-ene |
| F26sE | $C_2F_5CH=CHCF(CF_3)(CF_2)_2C_2F_5$ | 1,1,1,2,2,5,6,6,7,7,8,8,9,9,9-pentadecafluoro-5-(trifluoromethyl)non-3-ene |
| F26tE | $C_2F_5CH=CHC(CF_3)_2CF_2C_2F_5$ | 1,1,1,2,2,6,6,7,7,8,8,8-dodecafluoro-5,5-bis(trifluoromethyl)oct-3-ene |
| F35E | $C_2F_5CF_2CH=CH-(CF_2)_4CF_3$ | 1,1,1,2,2,3,3,6,6,7,7,8,8,9,9,10,10,10-octadecafluorodec-4-ene |
| F35iE | $C_2F_5CF_2CH=CH-CF_2CF_2CF(CF_3)_2$ | 1,1,1,2,2,3,3,6,6,7,7,8,9,9,9-pentadecafluoro-8-(trifluoromethyl)non-4-ene |
| F35tE | $C_2F_5CF_2CH=CH-C(CF_3)_2C_2F_5$ | 1,1,1,2,2,3,3,7,7,8,8,8-dodecafluoro-6,6-bis(trifluoromethyl)oct-4-ene |
| F3i5E | $(CF_3)_2CFCH=CH-(CF_2)_4CF_3$ | 1,1,1,2,5,5,6,6,7,7,8,8,9,9,9-pentadecafluoro-2-(trifluoromethyl)non-3-ene |
| F3i5iE | $(CF_3)_2CFCH=CH-CF_2CF_2CF(CF_3)_2$ | 1,1,1,2,5,5,6,6,7,8,8,8-dodecafluoro-2,7-bis(trifluoromethyl)oct-3-ene |
| F3i5tE | $(CF_3)_2CFCH=CH-C(CF_3)_2C_2F_5$ | 1,1,1,2,6,6,7,7,7-nonafluoro-2,5,5-tris(trifluoromethyl)hept-3-ene |
| F44E | $CF_3(CF_2)_3CH=CH-(CF_2)_3CF_3$ | 1,1,1,2,2,3,3,4,4,7,7,8,8,9,9,10,10,10-octadecafluorodec-5-ene |
| F44iE | $CF_3(CF_2)_3CH=CH-CF_2CF(CF_3)_2$ | 1,1,1,2,3,3,6,6,7,7,8,8,9,9,9-pentadecafluoro-2-(trifluoromethyl)non-4-ene |
| F44sE | $CF_3(CF_2)_3CH=CH-CF(CF_3)C_2F_5$ | 1,1,1,2,2,3,6,6,7,7,8,8,9,9,9-pentadecafluoro-3-(trifluoromethyl)non-4-ene |
| F44tE | $CF_3(CF_2)_3CH=CH-C(CF_3)_3$ | 1,1,1,5,5,6,6,7,7,8,8,8-dodecafluoro-2,2,-bis(trifluoromethyl)oct-3-ene |

TABLE 1-continued

| Code | Structure | Chemical Name |
|---|---|---|
| F4i4iE | $(CF_3)_2CFCF_2CH=CH-CF_2CF(CF_3)_2$ | 1,1,1,2,3,3,6,6,7,8,8,8-dodecafluoro-2,7-bis(trifluoromethyl)oct-4-ene |
| F4i4sE | $(CF_3)_2CFCF_2CH=CH-CF(CF_3)C_2F_5$ | 1,1,1,2,3,3,6,7,7,8,8,8-dodecafluoro-2,6-bis(trifluoromethyl)oct-4-ene |
| F4i4tE | $(CF_3)_2CFCF_2CH=CH-C(CF_3)_3$ | 1,1,1,5,5,6,7,7,7-nonafluoro-2,2,6-tris(trifluoromethyl)hept-3-ene |
| F4s4sE | $C_2F_5CF(CF_3)CH=CH-CF(CF_3)C_2F_5$ | 1,1,1,2,2,3,6,7,7,8,8,8-dodecafluoro-3,6-bis(trifluoromethyl)oct-4-ene |
| F4s4tE | $C_2F_5CF(CF_3)CH=CH-C(CF_3)_3$ | 1,1,1,5,6,6,7,7,7-nonafluoro-2,2,5-tris(trifluoromethyl)hept-3-ene |
| F4t4tE | $(CF_3)_3CCH=CH-C(CF_3)_3$ | 1,1,1,6,6,6-hexafluoro-2,2,5,5-tetrakis(trifluoromethyl)hex-3-ene |

Compounds of Formula I may be prepared by contacting a perfluoroalkyl iodide of the formula $R^1I$ with a perfluoroalkyltrihydroolefin of the formula $R^2CH=CH_2$ to form a trihydroiodoperfluoroalkane of the formula $R^1CH_2CHIR^2$. This trihydroiodoperfluoroalkane can then be dehydroiodinated to form $R^1CH=CHR^2$. Alternatively, the olefin $R^1CH=CHR^2$ may be prepared by dehydroiodination of a trihydroiodoperfluoroalkane of the formula $R^1CHICH_2R^2$ formed in turn by reacting a perfluoroalkyl iodide of the formula $R^{21}$ with a perfluoroalkyltrihydroolefin of the formula $R^1CH=CH_2$.

Said contacting of a perfluoroalkyl iodide with a perfluoroalkyltrihydroolefin may take place in batch mode by combining the reactants in a suitable reaction vessel capable of operating under the autogenous pressure of the reactants and products at reaction temperature. Suitable reaction vessels include fabricated from stainless steels, in particular of the austenitic type, and the well-known high nickel alloys such as Monel® nickel-copper alloys, Hastelloy® nickel based alloys and Inconel® nickel-chromium alloys.

Alternatively, the reaction may take be conducted in semi-batch mode in which the perfluoroalkyltrihydroolefin reactant is added to the perfluoroalkyl iodide reactant by means of a suitable addition apparatus such as a pump at the reaction temperature.

The ratio of perfluoroalkyl iodide to perfluoroalkyltrihydroolefin should be between about 1:1 to about 4:1, preferably from about 1.5:1 to 2.5:1. Ratios less than 1.5:1 tend to result in large amounts of the 2:1 adduct as reported by Jeanneaux, et. al. in *Journal of Fluorine Chemistry*, Vol. 4, pages 261-270 (1974).

Preferred temperatures for contacting of said perfluoroalkyl iodide with said perfluoroalkyltrihydroolefin are preferably within the range of about 150° C. to 300° C., preferably from about 170° C. to about 250° C., and most preferably from about 180° C. to about 230° C.

Suitable contact times for the reaction of the perfluoroalkyl iodide with the perfluoroalkyltrihydroolefin are from about 0.5 hour to 18 hours, preferably from about 4 to about 12 hours.

The trihydroiodoperfluoroalkane prepared by reaction of the perfluoroalkyl iodide with the perfluoroalkyltrihydroolefin may be used directly in the dehydroiodination step or may preferably be recovered and purified by distillation prior to the dehydroiodination step.

The dehydroiodination step is carried out by contacting the trihydroiodoperfluoroalkane with a basic substance. Suitable basic substances include alkali metal hydroxides (e.g., sodium hydroxide or potassium hydroxide), alkali metal oxide (for example, sodium oxide), alkaline earth metal hydroxides (e.g., calcium hydroxide), alkaline earth metal oxides (e.g., calcium oxide), alkali metal alkoxides (e.g., sodium methoxide or sodium ethoxide), aqueous ammonia, sodium amide, or mixtures of basic substances such as soda lime. Preferred basic substances are sodium hydroxide and potassium hydroxide.

Said contacting of the trihydroiodoperfluoroalkane with a basic substance may take place in the liquid phase preferably in the presence of a solvent capable of dissolving at least a portion of both reactants. Solvents suitable for the dehydroiodination step include one or more polar organic solvents such as alcohols (e.g., methanol, ethanol, n-propanol, isopropanol, n-butanol, isobutanol, and tertiary butanol), nitriles (e.g., acetonitrile, propionitrile, butyronitrile, benzonitrile, or adiponitrile), dimethyl sulfoxide, N,N-dimethylformamide, N,N-dimethylacetamide, or sulfolane. The choice of solvent may depend on the boiling point product and the ease of separation of traces of the solvent from the product during purification. Typically, ethanol or isopropanol are good solvents for the reaction.

Typically, the dehydroiodination reaction may be carried out by addition of one of the reactants (either the basic substance or the trihydroiodoperfluoroalkane) to the other reactant in a suitable reaction vessel. Said reaction may be fabricated from glass, ceramic, or metal and is preferably agitated with an impeller or stirring mechanism.

Temperatures suitable for the dehydroiodination reaction are from about 10° C. to about 100° C., preferably from about 20° C. to about 70° C. The dehydroiodination reaction may be carried out at ambient pressure or at reduced or elevated pressure. Of note are dehydroiodination reactions in which the compound of Formula I is distilled out of the reaction vessel as it is formed.

Alternatively, the dehydroiodination reaction may be conducted by contacting an aqueous solution of said basic substance with a solution of the trihydroiodoperfluoroalkane in one or more organic solvents of lower polarity such as an alkane (e.g., hexane, heptane, or octane), aromatic hydrocarbon (e.g., toluene), halogenated hydrocarbon (e.g., methylene chloride, chloroform, carbon tetrachloride, or perchloroethylene), or ether (e.g., diethyl ether, methyl tert-butyl ether, tetrahydrofuran, 2-methyl tetrahydrofuran, dioxane, dimethoxyethane, diglyme, or tetraglyme) in the presence of a phase transfer catalyst. Suitable phase transfer catalysts include quaternary ammonium halides (e.g., tetrabutylammonium bromide, tetrabutylammonium hydrosulfate, triethylbenzylammonium chloride, dodecyltrimethylammonium chloride, and tricaprylylmethylammonium chloride), quaternary phosphonium halides (e.g., triphenylmethylphosphonium bromide and tetraphenylphosphonium chloride), or cyclic polyether compounds known in the art as crown ethers (e.g., 18-crown-6 and 15-crown-5).

Alternatively, the dehydroiodination reaction may be conducted in the absence of solvent by adding the trihydroiodoperfluoroalkane to a solid or liquid basic substance.

Suitable reaction times for the dehydroiodination reactions are from about 15 minutes to about six hours or more depending on the solubility of the reactants. Typically the dehydroiodination reaction is rapid and requires about 30 minutes to about three hours for completion. The compound of formula I may be recovered from the dehydroiodination reaction mixture by phase separation after addition of water, by distillation, or by a combination thereof.

In another embodiment of the present invention, fluoroolefins comprise cyclic unsaturated fluorocarbons (cyclo-[CX=CY(CZW)$_n$-] (Formula II), wherein X, Y, Z, and W are independently selected from H and F, and n is an integer from 2 to 5). In one embodiment the fluoroolefins of Formula II, have at least about 3 carbon atoms in the molecule. In another embodiment, the fluoroolefins of Formula II have at least about 4 carbon atoms in the molecule. In yet another embodiment, the fluoroolefins of Formula II have at least about 5 carbon atoms in the molecule. Representative cyclic fluoroolefins of Formula II are listed in Table 2.

TABLE 2

| Cyclic unsaturated fluorocarbons | Structure | Chemical name |
|---|---|---|
| FC-C1316cc | cyclo-$CF_2CF_2CF=CF-$ | 1,2,3,3,4,4-hexafluorocyclobutene |
| HFC-C1334cc | cyclo-$CF_2CF_2CH=CH-$ | 3,3,4,4-tetrafluorocyclobutene |
| HFC-C1436 | cyclo-$CF_2CF_2CF_2CH=CH-$ | 3,3,4,4,5,5,-hexafluorocyclopentene |
| FC-C1418y | cyclo-$CF_2CF=CFCF_2CF_2-$ | 1,2,3,3,4,4,5,5-octafluorocyclopentene |
| FC-C151-10y | cyclo-$CF_2CF=CFCF_2CF_2CF_2-$ | 1,2,3,3,4,4,5,5,6,6-decafluorocyclohexene |

The compositions of the present invention may comprise a single compound of Formula I or formula II, for example, one of the compounds in Table 1 or Table 2, or may comprise a combination of compounds of Formula I or Formula II.

In another embodiment, fluoroolefins may comprise those compounds listed in Table 3.

TABLE 3

| Name | Structure | Chemical name |
|---|---|---|
| HFC-1114 (TFE) | $CF_2=CF_2$ | tetrafluoroethylene |
| HFC-1216 (HFP) | $CF_3CF=CF_2$ | hexafluoropropene |
| HFC-1225ye | $CF_3CF=CHF$ | 1,2,3,3,3-pentafluoro-1-propene |
| HFC-1225zc | $CF_3CH=CF_2$ | 1,1,3,3,3-pentafluoro-1-propene |
| HFC-1225yc | $CHF_2CF=CF_2$ | 1,1,2,3,3-pentafluoro-1-propene |
| HFC-1234ye | $CHF_2CF=CHF$ | 1,2,3,3-tetrafluoro-1-propene |
| HFC-1234yf | $CF_3CF=CH_2$ | 2,3,3,3-tetrafluoro-1-propene |
| HFC-1234ze | $CF_3CH=CHF$ | 1,3,3,3-tetrafluoro-1-propene |
| HFC-1234yc | $CH_2FCF=CF_2$ | 1,1,2,3-tetrafluoro-1-propene |
| HFC-1234zc | $CHF_2CH=CF_2$ | 1,1,3,3-tetrafluoro-1-propene |
| HFC-1243yf | $CHF_2CF=CH_2$ | 2,3,3-trifluoro-1-propene |
| HFC-1243zf | $CF_3CH=CH_2$ | 3,3,3-trifluoro-1-propene |
| HFC-1243yc | $CH_3CF=CF_2$ | 1,1,2-trifluoro-1-propene |
| HFC-1243zc | $CH_2FCH=CF_2$ | 1,1,3-trifluoro-1-propene |
| HFC-1243ye | $CH_2FCF=CHF$ | 1,2,3-trifluoro-1-propene |
| HFC-1243ze | $CHF_2CH=CHF$ | 1,3,3-trifluoro-1-propene |
| FC-1318my | $CF_3CF=CFCF_3$ | 1,1,1,2,3,4,4,4-octafluoro-2-butene |
| FC-1318cy | $CF_3CF_2CF=CF_2$ | 1,1,2,3,3,4,4,4-octafluoro-1-butene |
| HFC-1327my | $CF_3CF=CHCF_3$ | 1,1,1,2,4,4,4-heptafluoro-2-butene |
| HFC-1327ye | $CHF=CFCF_2CF_3$ | 1,2,3,3,4,4,4-heptafluoro-1-butene |
| HFC-1327py | $CHF_2CF=CFCF_3$ | 1,1,1,2,3,4,4-heptafluoro-2-butene |
| HFC-1327et | $(CF_3)_2C=CHF$ | 1,3,3,3-tetrafluoro-2-(trifluoromethyl)-1-propene |
| HFC-1327cz | $CF_2=CHCF_2CF_3$ | 1,1,3,3,4,4,4-heptafluoro-1-butene |
| HFC-1327cye | $CF_2=CFCHFCF_3$ | 1,1,2,3,4,4,4-heptafluoro-1-butene |
| HFC-1327cyc | $CF_2=CFCF_2CHF_2$ | 1,1,2,3,3,4,4-heptafluoro-1-butene |
| HFC-1336yf | $CF_3CF_2CF=CH_2$ | 2,3,3,4,4,4-hexafluoro-1-butene |
| HFC-1336ze | $CHF=CHCF_2CF_3$ | 1,3,3,4,4,4-hexafluoro-1-butene |
| HFC-1336eye | $CHF=CFCHFCF_3$ | 1,2,3,4,4,4-hexafluoro-1-butene |
| HFC-1336eyc | $CHF=CFCF_2CHF_2$ | 1,2,3,3,4,4-hexafluoro-1-butene |
| HFC-1336pyy | $CHF_2CF=CFCHF_2$ | 1,1,2,3,4,4-hexafluoro-2-butene |

TABLE 3-continued

| Name | Structure | Chemical name |
|---|---|---|
| HFC-1336qy | CH$_2$FCF=CFCF$_3$ | 1,1,1,2,3,4-hexafluoro-2-butene |
| HFC-1336pz | CHF$_2$CH=CFCF$_3$ | 1,1,1,2,4,4-hexafluoro-2-butene |
| HFC-1336mzy | CF$_3$CH=CFCHF$_2$ | 1,1,1,3,4,4-hexafluoro-2-butene |
| HFC-1336qc | CF$_2$=CFCF$_2$CH$_2$F | 1,1,2,3,3,4-hexafluoro-1-butene |
| HFC-1336pe | CF$_2$=CFCHFCHF$_2$ | 1,1,2,3,4,4-hexafluoro-1-butene |
| HFC-1336ft | CH$_2$=C(CF$_3$)$_2$ | 3,3,3-trifluoro-2-(trifluoromethyl)-1-propene |
| HFC-1345qz | CH$_2$FCH=CFCF$_3$ | 1,1,1,2,4-pentafluoro-2-butene |
| HFC-1345mzy | CF$_3$CH=CFCH$_2$F | 1,1,1,3,4-pentafluoro-2-butene |
| HFC-1345fz | CF$_3$CF$_2$CH=CH$_2$ | 3,3,4,4,4-pentafluoro-1-butene |
| HFC-1345mzz | CHF$_2$CH=CHCF$_3$ | 1,1,1,4,4-pentafluoro-2-butene |
| HFC-1345sy | CH$_3$CF=CFCF$_3$ | 1,1,1,2,3-pentafluoro-2-butene |
| HFC-1345fyc | CH$_2$=CFCF$_2$CHF$_2$ | 2,3,3,4,4-pentafluoro-1-butene |
| HFC-1345pyz | CHF$_2$CF=CHCHF$_2$ | 1,1,2,4,4-pentafluoro-2-butene |
| HFC-1345cyc | CH$_3$CF$_2$CF=CF$_2$ | 1,1,2,3,3-pentafluoro-1-butene |
| HFC-1345pyy | CH$_2$FCF=CFCHF$_2$ | 1,1,2,3,4-pentafluoro-2-butene |
| HFC-1345eyc | CH$_2$FCF$_2$CF=CF$_2$ | 1,2,3,3,4-pentafluoro-1-butene |
| HFC-1345ctm | CF$_2$=C(CF$_3$)(CH$_3$) | 1,1,3,3,3-pentafluoro-2-methyl-1-propene |
| HFC-1345ftp | CH$_2$=C(CHF$_2$)(CF$_3$) | 2-(difluoromethyl)-3,3,3-trifluoro-1-propene |
| HFC1345fye | CH$_2$=CFCHFCF$_3$ | 2,3,4,4,4-pentafluoro-1-butene |
| HFC-1345eyf | CHF=CFCH$_2$CF$_3$ | 1,2,4,4,4-pentafluoro-1-butene |
| HFC-1345eze | CHF=CHCHFCF$_3$ | 1,3,4,4,4-pentafluoro-1-butene |
| HFC-1345ezc | CHF=CHCF$_2$CHF$_2$ | 1,3,3,4,4-pentafluoro-1-butene |
| HFC-1345eye | CHF=CFCHFCHF$_2$ | 1,2,3,4,4-pentafluoro-1-butene |
| HFC-1354fzc | CH$_2$=CHCF$_2$CHF$_2$ | 3,3,4,4-tetrafluoro-1-butene |
| HFC-1354ctp | CF$_2$=C(CHF$_2$)(CH$_3$) | 1,1,3,3-tetrafluoro-2-methyl-1-propene |
| HFC-1354etm | CHF=C(CF$_3$)(CH$_3$) | 1,3,3,3-tetrafluoro-2-methyl-1-propene |
| HFC-1354tfp | CH$_2$=C(CHF$_2$)$_2$ | 2-(difluoromethyl)-3,3-difluoro-1-propene |
| HFC-1354my | CF$_3$CF=CHCH$_3$ | 1,1,1,2-tetrafluoro-2-butene |
| HFC-1354mzy | CH$_3$CF=CHCF$_3$ | 1,1,1,3-tetrafluoro-2-butene |
| FC-141-10myy | CF$_3$CF=CFCF$_2$CF$_3$ | 1,1,1,2,3,4,4,5,5,5-decafluoro-2-pentene |
| FC-141-10cy | CF$_2$=CFCF$_2$CF$_2$CF$_3$ | 1,1,2,3,3,4,4,5,5,5-decafluoro-1-pentene |
| HFC-1429mzt | (CF$_3$)$_2$C=CHCF$_3$ | 1,1,1,4,4,4-hexafluoro-2-(trifluoromethyl)-2-butene |
| HFC-1429myz | CF$_3$CF=CHCF$_2$CF$_3$ | 1,1,1,2,4,4,5,5,5-nonafluoro-2-pentene |
| HFC-1429mzy | CF$_3$CH=CFCF$_2$CF$_3$ | 1,1,1,3,4,4,5,5,5-nonafluoro-2-pentene |
| HFC-1429eyc | CHF=CFCF$_2$CF$_2$CF$_3$ | 1,2,3,3,4,4,5,5,5-nonafluoro-1-pentene |
| HFC-1429czc | CF$_2$=CHCF$_2$CF$_2$CF$_3$ | 1,1,3,3,4,4,5,5,5-nonafluoro-1-pentene |
| HFC-1429cycc | CF$_2$=CFCF$_2$CF$_2$CHF$_2$ | 1,1,2,3,3,4,4,5,5-nonafluoro-1-pentene |
| HFC-1429pyy | CHF$_2$CF=CFCF$_2$CF$_3$ | 1,1,2,3,4,4,5,5,5-nonafluoro-2-pentene |
| HFC-1429myyc | CF$_3$CF=CFCF$_2$CHF$_2$ | 1,1,1,2,3,4,4,5,5-nonafluoro-2-pentene |
| HFC-1429myye | CF$_3$CF=CFCHFCF$_3$ | 1,1,1,2,3,4,5,5,5-nonafluoro-2-pentene |
| HFC-1429eyym | CHF=CFCF(CF$_3$)$_2$ | 1,2,3,4,4,4-hexafluoro-3-(trifluoromethyl)-1-butene |
| HFC-1429cyzm | CF$_2$=CFCH(CF$_3$)$_2$ | 1,1,2,4,4,4-hexafluoro-3-(trifluoromethyl)-1-butene |
| HFC-1429mzt | CF$_3$CH=C(CF$_3$)$_2$ | 1,1,1,4,4,4-hexafluoro-2-(trifluoromethyl)-2-butene |
| HFC-1429czym | CF$_2$=CHCF(CF$_3$)$_2$ | 1,1,3,4,4,4-hexafluoro-3-(trifluoromethyl)-1-butene |
| HFC-1438fy | CH$_2$=CFCF$_2$CF$_2$CF$_3$ | 2,3,3,4,4,5,5,5-octafluoro-1-pentene |
| HFC-1438eycc | CHF=CFCF$_2$CF$_2$CHF$_2$ | 1,2,3,3,4,4,5,5-octafluoro-1-pentene |
| HFC-1438ftmc | CH$_2$=C(CF$_3$)CF$_2$CF$_3$ | 3,3,4,4,4-pentafluoro-2-(trifluoromethyl)-1-butene |
| HFC-1438czzm | CF$_2$=CHCH(CF$_3$)$_2$ | 1,1,4,4,4-pentafluoro-3-(trifluoromethyl)-1-butene |
| HFC-1438ezym | CHF=CHCF(CF$_3$)$_2$ | 1,3,4,4,4-pentafluoro-3-(trifluoromethyl)-1-butene |
| HFC-1438ctmf | CF$_2$=C(CF$_3$)CH$_2$CF$_3$ | 1,1,4,4,4-pentafluoro-2-(trifluoromethyl)-1-butene |
| HFC-1447fzy | (CF$_3$)$_2$CFCH=CH$_2$ | 3,4,4,4-tetrafluoro-3-(trifluoromethyl)-1-butene |
| HFC-1447fz | CF$_3$CF$_2$CF$_2$CH=CH$_2$ | 3,3,4,4,5,5,5-heptafluoro-1-pentene |
| HFC-1447fycc | CH$_2$=CFCF$_2$CF$_2$CHF$_2$ | 2,3,3,4,4,5,5-heptafluoro-1-pentene |
| HFC-1447czcf | CF$_2$=CHCF$_2$CH$_2$CF$_3$ | 1,1,3,3,5,5,5-heptafluoro-1-pentene |
| HFC-1447mytm | CF$_3$CF=C(CF$_3$)(CH$_3$) | 1,1,1,2,4,4,4-heptafluoro-3-methyl-2-butene |
| HFC-1447fyz | CH$_2$=CFCH(CF$_3$)$_2$ | 2,4,4,4-tetrafluoro-3-(trifluoromethyl)-1-butene |
| HFC-1447ezz | CHF=CHCH(CF$_3$)$_2$ | 1,4,4,4-tetrafluoro-3-(trifluoromethyl)-1-butene |
| HFC-1447qzt | CH$_2$FCH=C(CF$_3$)$_2$ | 1,4,4,4-tetrafluoro-2-(trifluoromethyl)-2-butene |
| HFC-1447syt | CH$_3$CF=C(CF$_3$)$_2$ | 2,4,4,4-tetrafluoro-2-(trifluoromethyl)-2-butene |
| HFC-1456szt | (CF$_3$)$_2$C=CHCH$_3$ | 3-(trifluoromethyl)-4,4,4-trifluoro-2-butene |
| HFC-1456szy | CF$_3$CF$_2$CF=CHCH$_3$ | 3,4,4,5,5,5-hexafluoro-2-pentene |

TABLE 3-continued

| Name | Structure | Chemical name |
|---|---|---|
| HFC-1456mstz | $CF_3C(CH_3)=CHCF_3$ | 1,1,1,4,4,4-hexafluoro-2-methyl-2-butene |
| HFC-1456fzce | $CH_2=CHCF_2CHFCF_3$ | 3,3,4,5,5,5-hexafluoro-1-pentene |
| HFC-1456ftmf | $CH_2=C(CF_3)CH_2CF_3$ | 4,4,4-trifluoro-2-(trifluoromethyl)-1-butene |
| FC-151-12c | $CF_3(CF_2)_3CF=CF_2$ | 1,1,2,3,3,4,4,5,5,6,6,6-dodecafluoro-1-hexene (or perfluoro-1-hexene) |
| FC-151-12mcy | $CF_3CF_2CF=CFCF_2CF_3$ | 1,1,1,2,2,3,4,5,5,6,6,6-dodecafluoro-3-hexene (or perfluoro-3-hexene) |
| FC-151-12mmtt | $(CF_3)_2C=C(CF_3)_2$ | 1,1,1,4,4,4-hexafluoro-2,3-bis(trifluoromethyl)-2-butene |
| FC-151-12mmzz | $(CF_3)_2CFCF=CFCF_3$ | 1,1,1,2,3,4,5,5,5-nonafluoro-4-(trifluoromethyl)-2-pentene |
| HFC-152-11mmtz | $(CF_3)_2C=CHC_2F_5$ | 1,1,1,4,4,5,5,5-octafluoro-2-(trifluoromethyl)-2-pentene |
| HFC-152-11mmyyz | $(CF_3)_2CFCF=CHCF_3$ | 1,1,1,3,4,5,5,5-octafluoro-4-(trifluoromethyl)-2-pentene |
| PFBE (or HFC-1549fz) | $CF_3CF_2CF_2CF_2CH=CH_2$ | 3,3,4,4,5,5,6,6,6-nonafluoro-1-hexene (or perfluorobutylethylene) |
| HFC-1549fztmm | $CH_2=CHC(CF_3)_3$ | 4,4,4-trifluoro-3,3-bis(trifluoromethyl)-1-butene |
| HFC-1549mmtts | $(CF_3)_2C=C(CH_3)(CF_3)$ | 1,1,1,4,4,4-hexafluoro-3-methyl-2-(trifluoromethyl)-2-butene |
| HFC-1549fycz | $CH_2=CFCF_2CH(CF_3)_2$ | 2,3,3,5,5,5-hexafluoro-4-(trifluoromethyl)-1-pentene |
| HFC-1549myts | $CF_3CF=C(CH_3)CF_2CF_3$ | 1,1,1,2,4,4,5,5,5-nonafluoro-3-methyl-2-pentene |
| HFC-1549mzzz | $CF_3CH=CHCH(CF_3)_2$ | 1,1,1,5,5,5-hexafluoro-4-(trifluoromethyl)-2-pentene |
| HFC-1558szy | $CF_3CF_2CF_2CF=CHCH_3$ | 3,4,4,5,5,6,6,6-octafluoro-2-hexene |
| HFC-1558fzccc | $CH_2=CHCF_2CF_2CF_2CHF_2$ | 3,3,4,4,5,5,6,6-octafluoro-2-hexene |
| HFC-1558mmtzc | $(CF_3)_2C=CHCF_2CH_3$ | 1,1,1,4,4-pentafluoro-2-(trifluoromethyl)-2-pentene |
| HFC-1558ftmf | $CH_2=C(CF_3)CH_2C_2F_5$ | 4,4,5,5,5-pentafluoro-2-(trifluoromethyl)-1-pentene |
| HFC-1567fts | $CF_3CF_2CF_2C(CH_3)=CH_2$ | 3,3,4,4,5,5,5-heptafluoro-2-methyl-1-pentene |
| HFC-1567szz | $CF_3CF_2CF_2CH=CHCH_3$ | 4,4,5,5,6,6,6-heptafluoro-2-hexene |
| HFC-1567fzfc | $CH_2=CHCH_2CF_2C_2F_5$ | 4,4,5,5,6,6,6-heptafluoro-1-hexene |
| HFC-1567sfyy | $CF_3CF_2CF=CFC_2H_5$ | 1,1,1,2,2,3,4-heptafluoro-3-hexene |
| HFC-1567fzfy | $CH_2=CHCH_2CF(CF_3)_2$ | 4,5,5,5-tetrafluoro-4-(trifluoromethyl)-1-pentene |
| HFC-1567myzzm | $CF_3CF=CHCH(CF_3)(CH_3)$ | 1,1,1,2,5,5,5-heptafluoro-4-methyl-2-pentene |
| HFC-1567mmtyf | $(CF_3)_2C=CFC_2H_5$ | 1,1,1,3-tetrafluoro-2-(trifluoromethyl)-2-pentene |
| FC-161-14myy | $CF_3CF=CFCF_2CF_2C_2F_5$ | 1,1,1,2,3,4,4,5,5,6,6,7,7,7-tetradecafluoro-2-heptene |
| FC-161-14mcyy | $CF_3CF_2CF=CFCF_2C_2F_5$ | 1,1,1,2,2,3,4,5,5,6,6,7,7,7-tetradecafluoro-2-heptene |
| HFC-162-13mzy | $CF_3CH=CFCF_2CF_2C_2F_5$ | 1,1,1,3,4,4,5,5,6,6,7,7,7-tridecafluoro-2-heptene |
| HFC162-13myz | $CF_3CF=CHCF_2CF_2C_2F_5$ | 1,1,1,2,4,4,5,5,6,6,7,7,7-tridecafluoro-2-heptene |
| HFC-162-13mczy | $CF_3CF_2CH=CFCF_2C_2F_5$ | 1,1,1,2,2,4,5,5,6,6,7,7,7-tridecafluoro-3-heptene |
| HFC-162-13mcyz | $CF_3CF_2CF=CHCF_2C_2F_5$ | 1,1,1,2,2,3,5,5,6,6,7,7,7-tridecafluoro-3-heptene |

The compounds listed in Table 2 and Table 3 are available commercially or may be prepared by processes known in the art or as described herein.

1,1,1,4,4-pentafluoro-2-butene may be prepared from 1,1,1,2,4,4-hexafluorobutane ($CHF_2CH_2CHFCF_3$) by dehydrofluorination over solid KOH in the vapor phase at room temperature. The synthesis of 1,1,1,2,4,4-hexafluorobutane is described in U.S. Pat. No. 6,066,768, incorporated herein by reference.

1,1,1,4,4,4-hexafluoro-2-butene may be prepared from 1,1,1,4,4,4-hexafluoro-2-iodobutane ($CF_3CHICH_2CF_3$) by reaction with KOH using a phase transfer catalyst at about 60° C. The synthesis of 1,1,1,4,4,4-hexafluoro-2-iodobutane may be carried out by reaction of perfluoromethyl iodide ($CF_3I$) and 3,3,3-trifluoropropene ($CF_3CH=CH_2$) at about 200° C. under autogenous pressure for about 8 hours.

3,4,4,5,5,5-hexafluoro-2-pentene may be prepared by dehydrofluorination of 1,1,1,2,2,3,3-heptafluoropentane ($CF_3CF_2CF_2CH_2CH_3$) using solid KOH or over a carbon catalyst at 200-300° C. 1,1,1,2,2,3,3-heptafluoropentane may be prepared by hydrogenation of 3,3,4,4,5,5,5-heptafluoro-1-pentene ($CF_3CF_2CF_2CH=CH_2$).

1,1,1,2,3,4-hexafluoro-2-butene may be prepared by dehydrofluorination of 1,1,1,2,3,3,4-heptafluorobutane ($CH_2FCF_2CHFCF_3$) using solid KOH.

1,1,1,2,4,4-hexafluoro-2-butene may be prepared by dehydrofluorination of 1,1,1,2,2,4,4-heptafluorobutane ($CHF_2CH_2CF_2CF_3$) using solid KOH.

1,1,1,3,4,4-hexafluoro2-butene may be prepared by dehydrofluorination of 1,1,1,3,3,4,4-heptafluorobutane ($CF_3CH_2CF_2CHF_2$) using solid KOH.

1,1,1,2,4-pentafluoro-2-butene may be prepared by dehydrofluorination of 1,1,1,2,2,3-hexafluorobutane ($CH_2FCH_2CF_2CF_3$) using solid KOH.

1,1,1,3,4-pentafluoro-2-butene may be prepared by dehydrofluorination of 1,1,1,3,3,4-hexafluorobutane ($CF_3CH_2CF_2CH_2F$) using solid KOH.

1,1,1,3-tetrafluoro-2-butene may be prepared by reacting 1,1,1,3,3-pentafluorobutane ($CF_3CH_2CF_2CH_3$) with aqueous KOH at 120° C.

1,1,1,4,4,5,5,5-octafluoro-2-pentene may be prepared from ($CF_3CHICH_2CF_2CF_3$) by reaction with KOH using a phase transfer catalyst at about 60° C. The synthesis of 4-iodo-1,1,1,2,2,5,5,5-octafluoropentane may be carried out by reaction of perfluoroethyliodide ($CF_3CF_2I$) and 3,3,3-trifluoropropene at about 200° C. under autogenous pressure for about 8 hours.

1,1,1,2,2,5,5,6,6,6-decafluoro-3-hexene may be prepared from 1,1,1,2,2,5,5,6,6,6-decafluoro-3-iodohexane ($CF_3CF_2CHICH_2CF_2CF_3$) by reaction with KOH using a phase transfer catalyst at about 60° C. The synthesis of 1,1,1,2,2,5,5,6,6,6-decafluoro-3-iodohexane may be carried out by reaction of perfluoroethyliodide ($CF_3CF_2I$) and 3,3,4,4,4-pentafluoro-1-butene ($CF_3CF_2CH=CH_2$) at about 200° C. under autogenous pressure for about 8 hours.

1,1,1,4,5,5,5-heptafluoro-4-(trifluoromethyl)-2-pentene may be prepared by the dehydrofluorination of 1,1,1,2,5,5,5-heptafluoro-4-iodo-2-(trifluoromethyl)-pentane ($CF_3CHICH_2CF(CF_3)_2$) with KOH in isopropanol. $CF_3CHICH_2CF(CF_3)_2$ is made from reaction of $(CF_3)_2CFI$ with $CF_3CH=CH_2$ at high temperature, such as about 200° C.

1,1,1,4,4,5,5,6,6,6-decafluoro-2-hexene may be prepared by the reaction of 1,1,1,4,4,4-hexafluoro-2-butene ($CF_3CH=CHCF_3$) with tetrafluoroethylene ($CF_2=CF_2$) and antimony pentafluoride ($SbF_5$).

2,3,3,4,4-pentafluoro-1-butene may be prepared by dehydrofluorination of 1,1,2,2,3,3-hexafluorobutane over fluorided alumina at elevated temperature.

2,3,3,4,4,5,5,5-ocatafluoro-1-pentene may be prepared by dehydrofluorination of 2,2,3,3,4,4,5,5,5-nonafluoropentane over solid KOH.

1,2,3,3,4,4,5,5-octafluoro-1-pentene may be prepared by dehydrofluorination of 2,2,3,3,4,4,5,5,5-nonafluoropentane over fluorided alumina at elevated temperature.

Many of the compounds of Formula I, Formula II, Table 1, Table 2, and Table 3 exist as different configurational isomers or stereoisomers. When the specific isomer is not designated, the present invention is intended to include all single configurational isomers, single stereoisomers, or any combination thereof. For instance, F11E is meant to represent the E-isomer, Z-isomer, or any combination or mixture of both isomers in any ratio. As another example, HFC-1225ye is meant to represent the E-isomer, Z-isomer, or any combination or mixture of both isomers in any ratio.

The term "entrainer" is used herein to describe any compound that would be effective in separation of fluoroolefins from mixtures comprising HF and fluoroolefin in an azeotropic distillation process. Included as useful entrainers are those compounds that form azeotropes with one or more of the components of a mixture, including fluoroolefins, HF, and possible hydrofluorocarbons for which the boiling point of at least one of such azeotropes is lower than the boiling point of the fluoroolefin/HF azeotrope.

Entrainers may be selected from the group consisting of hydrocarbons, chlorocarbons, chlorofluorocarbons, hydrochlorofluorocarbons, hydrofluorocarbons, perfluorocarbons, fluoroethers, HFPO, $SF_6$, chlorine, hexafluoroacetone, and mixtures thereof.

Hydrocarbon entrainers comprise compounds containing 1 to 5 carbon atoms and hydrogen. Hydrocarbon entrainers may be linear, branched, cyclic, saturated or unsaturated compounds. Representative hydrocarbon entrainers include but are not limited to methane, ethane, ethylene, acetylene, vinylacetylene, n-propane, propylene, propyne, cyclopropane, cyclopropene, propadiene, n-butane, isobutane, 1-butene, isobutene, 1,3-butadiene, 2,2-dimethylpropane, cis-2-butene, trans-2-butene, 1-butyne, n-pentane, isopentane, neopentane, cyclopentane, 1-pentene, 2-pentene, and mixtures thereof.

Chlorocarbon entrainers comprise compounds containing carbon, chlorine and optionally hydrogen, including but not limited to methylene chloride ($CH_2Cl_2$), and methyl chloride ($CH_3Cl$).

Chlorofluorocarbon (CFC) entrainers comprise compounds with carbon, chlorine and fluorine. Representative CFCs include but are not limited to dichlorodifluoromethane (CFC-12), 2-chloro-1,1,2-trifluoroethylene, chloropentafluoroethane (CFC-115), 1,2-dichloro-1,1,2,2-tetrafluoroethane (CFC-114), 1,1-dichloro-1,2,2,2-tetrafluoroethane (CFC-114a), 1,1,2-trichloro-1,2,2-trifluoroethane (CFC-113), 1,1,1-trichloro-2,2,2-trifluoroethane (CFC-113a), 1,1,2-trichloro-1,2,3,3,3-pentafluoropropane (CFC-215bb), 2,2-dichloro-1,1,1,3,3,3-hexafluoropropane (CFC-216aa), 1,2-dichloro-1,1,2,3,3,3-hexafluoropropane (CFC-216ba), 2-chloro-1,1,1,2,3,3,3-heptafluoropropane (CFC-217ba), 2-chloro-1,1,3,3,3-pentafluoropropene (CFC-1215xc), and mixtures thereof.

Hydrochlorofluorocarbon (HCFC) entrainers comprise compounds with carbon, chlorine, fluorine and hydrogen. Representative HCFCs include but are not limited to dichlorofluoromethane (HCFC-21), 1,1-dichloro-3,3,3-trifluoroethane (HCFC-123), 1,1-dichloro-1-fluoroethane (HCFC-141b), 2-chloro-1,1,1,2-tetrafluoroethane (HCFC-124), 1-chloro-1,1,2,2-tetrafluoroethane (HCFC-124a), 2-chloro-1,1,1-trifluoroethane (HCFC-133a), 1-chloro-1,1-difluoroethane (HCFC-142b), 2-chloro-1,1-difluoroethylene (HCFC-1122), and mixtures thereof.

Hydrofluorocarbon (HFC) entrainers comprise compounds that contain carbon, hydrogen and fluorine. Representative HFCs include but are not limited to 1,1,2-trifluoroethylene (HFC-1123), 1,1-difluoroethylene (HFC-1132a), 1,2,3,3,3-pentafluoropropene (HFC-1225ye, either of the Z- or E-isomers or a mixture thereof), 2,3,3,3-tetrafluoropropene (HFC-1234yf), 3,3,3-trifluoropropene (HFC-1243zf), 1,3,3,3-tetrafluoropropene (HFC-1234ze, either of the Z- or E-isomers or a mixture thereof), 1,1,1,3,4,4,5,5,5-nonafluoro-2-pentene (HFC-1429mzy), 1,1,1,2,2,4,5,5,6,6,7,7,7-tridecafluoro-3-heptene (HFC-162-13mczy), 1,1,1,2,2,3,5,5,6,6,7,7,7-tridecafluoro-3-heptene (HFC-162-13mcyz), and mixtures thereof.

Perfluorocarbon (PFC) entrainers comprise compounds with carbon and fluorine only. Representative PFCs include but are not limited to hexafluoroethane (PFC-116), octafluoropropane (PFC-218), 1,1,1,4,4,4-hexafluoro-2-butyne (PFBY-2), hexafluoropropylene (HFP, PFC-1216), hexafluorocyclopropane (PFC-C216), octafluorocyclobutane (PFC-C318), decafluorobutane (PFC-31-10, any isomer(s)), 2,3-dichloro-1,1,1,4,4,4-hexafluoro-2-butene (PFC-1316mxx), octafluoro-2-butene (PFC-1318my, cis and trans), hexafluorobutadiene (PFC-2316), and mixtures thereof.

Fluoroether entrainers comprise compounds with carbon, fluorine, optionally hydrogen and at least one ether group oxygen. Representative fluoroethers include but are not limited to trifluoromethyl-difluoromethyl ether (CF$_3$OCHF$_2$, HFOC-125E), 1,1-difluorodimethyl ether, tetrafluorodimethylether (HFOC-134E), difluoromethyl methyl ether (CHF$_2$OCH$_3$, HFOC-152aE), pentafluoroethyl methyl ether, and mixtures thereof.

Miscellaneous other compounds that may be useful as entrainers include HFPO, chlorine (Cl$_2$), hexafluoroacetone, PMVE (perfluoromethylvinylether), PEVE (perfluoroethylvinylether), and mixtures thereof.

Entrainers as described above are available commercially or may be produced by methods known in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

2. Separation Process—Azeotropic Distillation with No Entrainer

It has been discovered that some fluoroolefins form azeotrope compositions with HF. Generally, the fluoroolefin/HF azeotrope composition will boil at a lower temperature than either of the corresponding pure compounds. Several examples of such fluoroolefin/HF azeotropes are disclosed in U.S. Patent Publication numbers 2007-0100173 A1, 2007-0100174 A1, 2007-0099811 A1, 2007-0100175 A1, 2007-0100176 A1, and 2006-0116538 A1.

It has been unexpectedly calculated that in a few cases azeotrope compositions comprising fluoroolefins and HF may form two liquid phases when condensed and/or cooled. The two phases comprise a fluoroolefin-rich phase and an HF-rich phase. This phase behavior allows unique separation schemes utilizing liquid-liquid separation (such as decantation) of the two phases that are not possible with many saturated hydrofluorocarbons, which in general do not phase separate in the same manner.

In one embodiment, the present disclosure provides a process for separating a mixture comprising HF and fluoroolefin, said process comprising a) feeding the composition comprising HF and fluoroolefin to a first distillation column; b) removing an azeotrope composition comprising HF and fluoroolefin as a first distillate and either i) HF or ii) fluoroolefin as a first column bottoms composition; c) condensing the first distillate to form two liquid phases, being i) an HF-rich phase and ii) a fluoroolefin-rich phase; and d) recycling a first liquid phase enriched in the same compound that is removed as the first column bottoms, said first liquid phase being either i) HF-rich phase or ii) fluoroolefin-rich phase, back to the first distillation column.

Additionally, in another embodiment, the process as described in the paragraph above may further comprise feeding a second liquid phase not recycled in step (d), said second liquid phase being either i) HF-rich phase or ii) fluoroolefin-rich phase, to a second distillation zone, and recovering the compound not recovered in step (b) as the first column bottoms composition as the second column bottoms composition.

In another embodiment, a process is provided for separating a fluoroolefin from a mixture comprising hydrogen fluoride and said fluoroolefin, wherein said fluoroolefin is present in a concentration greater than the azeotrope concentration for hydrogen fluoride and said fluoroolefin, said process comprising: a) feeding said mixture comprising hydrogen fluoride and said fluoroolefin to a first distillation column; b) removing an azeotrope composition comprising hydrogen fluoride and fluoroolefin as a first distillate from the first distillation column; c) recovering fluoroolefin essentially free of hydrogen fluoride as a first bottoms composition from the first distillation column; and d) condensing the first distillate to form two liquid phases, being i) a hydrogen fluoride-rich phase and ii) a fluoroolefin-rich phase; and e) recycling the fluoroolefin-rich phase to the first distillation column.

In another embodiment, the process may further comprise: a) feeding the hydrogen fluoride-rich phase to a second distillation column, and b) recovering hydrogen fluoride essentially free of fluoroolefin from the bottom of the second distillation column.

In another embodiment, the second distillate comprising HF and fluoroolefin may be recycled to the two liquid phases.

In one embodiment, wherein the composition comprising HF and fluoroolefin has a concentration of fluoroolefin that is greater than the azeotrope concentration for fluoroolefin and HF, the first distillation column removes the excess fluoroolefin from the bottom of the column and the azeotrope composition exits the top of the column as the distillate. In another embodiment, the azeotrope composition comprising HF and fluoroolefin may be condensed and cooled thereby forming two liquid phases, an HF-rich phase and a fluoroolefin-rich phase.

In one embodiment, the fluoroolefin-rich phase is recycled back to the first distillation column and the HF-rich phase is fed to a second distillation column. As the HF-rich phase may have HF in excess of the azeotrope composition for HF/fluoroolefin, the excess HF will be removed from the second distillation column bottom.

Referring now to FIG. 1, one embodiment of this process is illustrated. A composition comprising HF and fluoroolefin is fed to a first column 110 via stream 100. This first column is operated under appropriate conditions to approach the low-boiling HF/fluoroolefin azeotrope. Because fluoroolefin is being fed to this first column in excess of that needed to form the azeotrope with the HF, fluoroolefin is recovered as the bottoms of the column via stream 120, while a composition near to the HF/fluoroolefin azeotrope is recovered as distillate via stream 130. Stream 130 is condensed in 140, mixed with a nearly azeotropic composition recycled from a second column 210 via stream 250 and the combined stream is subcooled in cooler 160 and sent to decanter 180 where the combined stream 170 separates into separate fluoroolefin-rich (190) and HF-rich (200) streams. Stream 190 is recycled to the first column as reflux. Stream 200 is fed to the top stage of the second distillation column 210, operated under conditions to approach the HF/fluoroolefin azeotrope. Because the HF is being fed to this second column in excess of that needed to form the low-boiling HF/fluoroolefin azeotrope, HF is recovered as the bottoms of the column via stream 220 while a composition close to the HF/fluoroolefin azeotrope is recovered as distillate via stream 230. Stream 230 is condensed in 240, mixed with the nearly azeotropic composition from the first column via stream 150 and fed to cooler 160 and then decanter 180.

In another embodiment, a process is provided for separating hydrogen fluoride from a mixture comprising hydrogen fluoride and a fluoroolefin, wherein hydrogen fluoride is present in a concentration greater than the azeotrope concentration for hydrogen fluoride and said fluoroolefin, said process comprising: a) feeding said mixture comprising hydrogen fluoride and fluoroolefin to a first distillation column; b) removing an azeotrope composition comprising fluoroolefin and HF as a first distillate from the first distillation column; c) recovering hydrogen fluoride essentially free of fluoroolefin from the bottom of the first distillation column d) condensing the first distillate to form two liquid phases, being an fluoroolefin-rich phase and a hydrogen fluoride-rich phase; and e) recycling the HF-rich phase to the first distillation column.

In another embodiment, the process may further comprise: a) feeding the fluoroolefin-rich phase to a second distillation column; and b) recovering fluoroolefin essentially free of hydrogen fluoride from the bottom of the second distillation column.

In another embodiment, the process may further comprise: recycling the hydrogen fluoride-rich phase to the first distillation column.

In another embodiment, the composition comprising HF and fluoroolefin has a greater concentration of HF than the azeotrope composition for HF and fluoroolefin. The excess HF may be removed from the bottom of the first distillation column and the azeotrope composition exits as the distillate. In another embodiment, the azeotrope composition comprising HF and fluoroolefin may be condensed and cooled thereby forming two liquid phases, an HF-rich phase and a fluoroolefin-rich phase. For this embodiment, the HF-rich phase is recycled back to the first distillation column and the fluoroolefin-rich phase is fed to a second distillation column. As the fluoroolefin-rich phase may have fluoroolefin in excess of the azeotrope composition for HF/fluoroolefin, the excess fluoroolefin may be removed from the second distillation column bottom as fluoroolefin essentially free of HF.

Referring again to FIG. 1, another embodiment of this process is illustrated. A composition comprising HF and fluoroolefin is fed to a first column 110 via stream 100. This first column is operated under appropriate conditions to approach the low-boiling HF/fluoroolefin azeotrope. Because HF is being fed to this first column in excess of that needed to form the azeotrope with the fluoroolefin, HF is recovered as the bottoms of the column via stream 120, while a composition near to the HF/fluoroolefin azeotrope is recovered as distillate via stream 130. Stream 130 is condensed in 140, mixed with a nearly azeotropic composition recycled from a second column via stream 250 and the combined stream is sub-cooled in cooler 160 and sent to decanter 180 where the combined stream 170 separates into separate HF-rich (190) and fluoroolefin-rich (200) streams. Stream 190 is recycled to the first column as reflux. Stream 200 is fed to the top stage of the second distillation column 210, operated under conditions to approach the HF/fluoroolefin azeotrope. Because fluoroolefin is being fed to this second column in excess of that needed to form the low-boiling HF/fluoroolefin azeotrope, Fluoroolefin is recovered as the bottoms of the column via stream 220, while a composition close to the HF/fluoroolefin azeotrope is recovered as distillate via stream 230. Stream 230 is condensed in 240, mixed with the nearly azeotropic composition from the first column via stream 150 and fed to cooler 160 and then decanter 180.

In one embodiment the operating conditions for the first and second distillation columns will depend upon the fluoroolefin being purified and the relative amounts of HF and fluoroolefin in the composition to be separated.

In one embodiment, the first and second distillation column may operate at from about 14.7 psia (101 kPa) to about 300 psia (2068 kPa), with a top temperature of from about −50° C. to about 200° C. and a bottom temperature from about −30° C. to about 220° C. In another embodiment, the pressure will range from about 50 psia (345 kPa) to about 250 psia (1724 kPa), with a top temperature of from about −25° C. to about 100° C. and a bottom temperature from about 0° C. to about 150° C.

3. Separation Process—Azeotropic Distillation with an Entrainer

Azeotropic distillation for separating fluoroolefin from mixtures of HF and fluoroolefin may, in another embodiment, be carried out using an entrainer compound. For the process including an entrainer, the azeotrope composition need not phase separate upon condensing and cooling as described above.

In one embodiment, the entrainer serves to provide an improved liquid-liquid phase separation for a system wherein that separation would otherwise not be effective.

In one embodiment, the fluoroolefin is present in the HF/fluoroolefin mixture in a concentration greater than the azeotrope concentration for said fluoroolefin and HF. Thus, in one embodiment is provided a process for the purification of a fluoroolefin from a mixture comprising fluoroolefin and HF, wherein said fluoroolefin is present in said mixture in a concentration greater than the azeotrope concentration for said fluoroolefin and HF, said process comprising:

a. adding an entrainer to the mixture comprising fluoroolefin and HF thus forming a second mixture;

b. distilling said second mixture in a first distillation step to form a first distillate composition comprising HF, fluoroolefin, and entrainer, and a first bottoms composition comprising fluoroolefin essentially free of HF and entrainer;

c. condensing said first distillate composition to form two liquid phases, being i) an HF-rich phase and ii) an entrainer-rich phase; and d. optionally recycling the entrainer-rich phase back to the first distillation step. In another embodiment, the process further comprises feeding the HF-rich phase to a second distillation step and forming a second distillate composition comprising entrainer, fluoroolefin and HF and a bottoms composition comprising HF essentially free of fluoroolefin and entrainer. In another embodiment, the process may further comprise recycling said second distillate composition back to the two liquid phases.

The process for separating a fluoroolefin from a first composition comprising HF and fluoroolefin comprises contacting said first composition with an entrainer to form a second composition. The contacting may occur in a first distillation column, or the second composition may be formed by mixing the components prior to feeding to a distillation column in a pre-mixing step.

The weight ratio of the HF and fluoroolefin in the first composition will depend upon the means of producing the composition. In one embodiment, the HF may be from about 3 weight percent to about 85 weight percent of the composition; the fluoroolefin may be from about 97 weight percent to about 15 weight percent.

In another embodiment, the HF may be from about 5 weight percent to about 50 weight percent and the fluoroolefin may be from about 95 weight percent to about 50 weight percent In yet another embodiment the composition comprising HF and fluoroolefin may be produced in a dehydrofluorination reactor resulting in a 50/50 mole ratio of HF to the fluoroolefin.

In one embodiment, the compositions comprising HF and fluoroolefin may be prepared by any convenient method to combine the desired amounts of the individual components. A preferred method is to weigh the desired component amounts and thereafter combine the components in an appropriate vessel. Agitation may be used, if desired.

Alternatively, the compositions comprising HF and fluoroolefin may be prepared by feeding the effluent from a reactor, including a dehydrofluorination reactor that contains HF and fluoroolefin, to the first distillation column. The entrainer may be added at a separate feed point such that the second composition is formed directly in the distillation column. Alternatively, the entrainer may be mixed with the first composition comprising HF and fluoroolefin thus forming the second composition prior to the distillation column in a pre-mixing step.

In one embodiment of the separation process, a composition comprising fluoroolefin and HF is fed directly to a first distillation column. In another embodiment, the fluoroolefin and HF may be pre-mixed with an entrainer prior to the distillation column. The pre-mixing step may occur in a cooler (160 in FIG. 2). Then the cooled mixture is fed to a decanter (180 in FIG. 2) prior to feeding to the distillation column.

In one embodiment, the first distillate composition comprises a low boiling azeotrope of HF and entrainer optionally containing minor amounts of fluoroolefin. Further, in another embodiment, the fluoroolefin essentially free of HF and optionally minor amounts of entrainer may be recovered from the bottom of the first distillation column.

The operating variables for the first distillation column will depend strongly on the entrainer being used in the separation process. In general the first distillation column may operate at pressures from about 14.7 psia (101 kPa) to about 500 psia (3448 kPa) with a top temperature of from about −50° C. to about 100° C. and a bottom temperature of from about −30° C. to about 200° C. In another embodiment, the first distillation column will operate at pressures from about 100 psia (690 kPa) to about 400 psia (2758 kPa) with a top temperature of from about −50° C. to about 50° C. and a bottom temperature from about 10° C. to about 150° C.

It was surprisingly calculated that in some few cases, azeotropes of HF and compounds used as entrainers will separate into HF-rich and entrainer-rich liquid fractions upon condensing and being cooled. In one embodiment, the first distillate composition may be fed to a liquid separation zone (e.g. decanter). The first distillate composition comprising an azeotrope of HF and entrainer may be phase separated forming two liquid phases, one being HF-rich and the other being entrainer-rich. The lower density phase may be recovered from the top of the liquid separation zone and the higher density phase may be recovered from the bottom of the liquid separation zone. The entrainer-rich phase (whether higher or lower density) may be fed back to the first distillation column. In one embodiment the HF-rich phase may be fed to a second distillation column or in another embodiment, the HF-rich phase may be split to send some portion back to the first distillation column (in order to provide more reflux and allow the first distillation column to operate properly) and the remainder may be fed to the second distillation column. The second distillation column allows recovery of HF essentially free of fluoroolefin and entrainer as a bottoms composition. The top composition comprising fluoroolefin, HF and entrainer may be recycled to the liquid separation zone, be utilized in some other manner, or disposed. The operating variables for the second distillation column will depend strongly on the entrainer being used in the separation process. In general the second distillation column may operate at pressures from about 14.7 psia (101 kPa) to about 500 psia (3448 kPa) with a top temperature of from about −50° C. to about 100° C. and a bottom temperature of from about −30° C. to about 200° C. In another embodiment, the first distillation column will operate at pressures from about 100 psia (690 kPa) to about 400 psia (2758 kPa) with a top temperature of from about −25° C. to about 50° C. and a bottom temperature from about zero ° C. to about 150° C.

Figure 2:
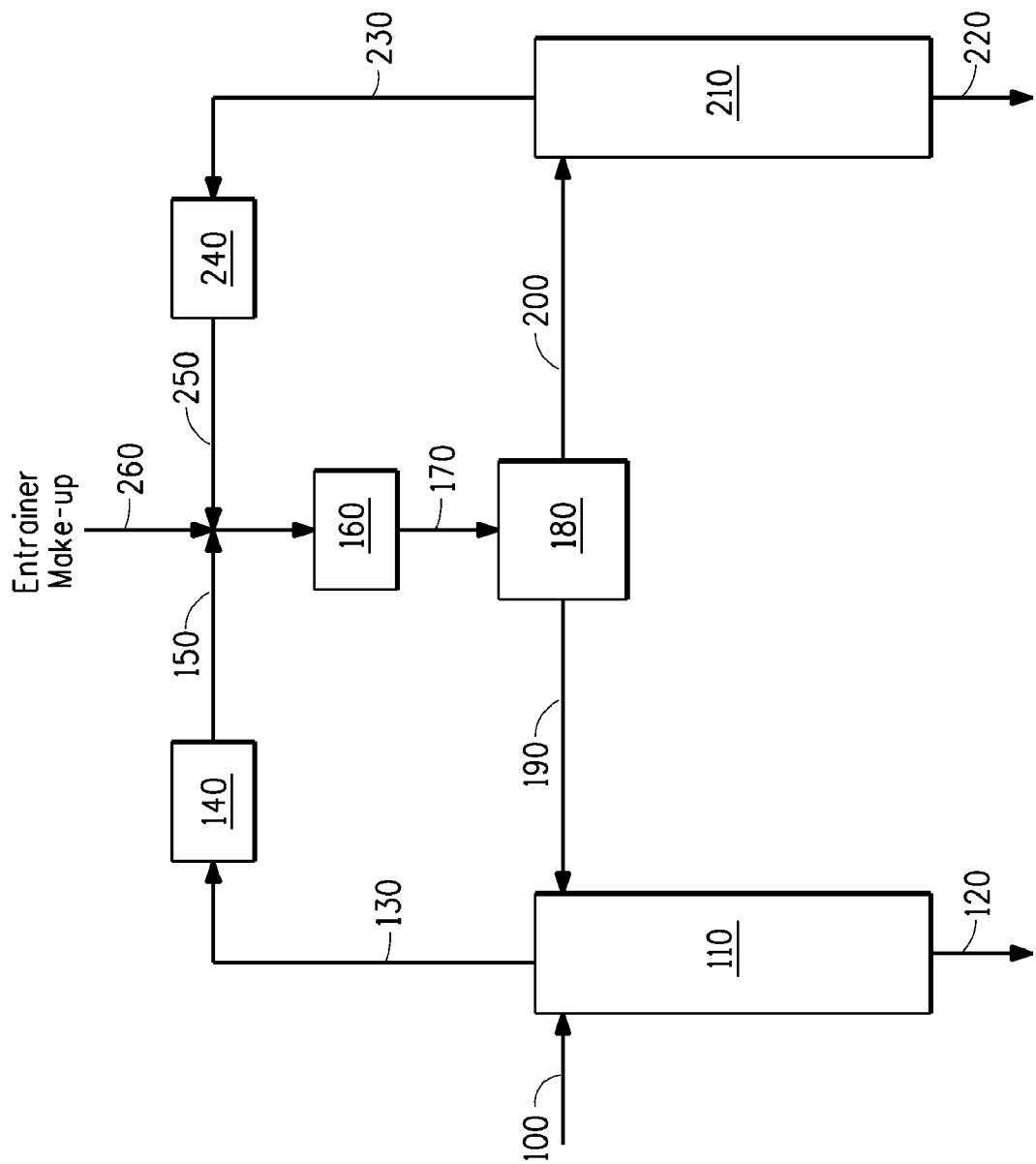
FIG. 2 is an illustration of one embodiment of an azeotropic distillation for the separation of HF and a fluoroolefin with an added entrainer.

Referring now to FIG. 2, a composition comprising HF and fluoroolefin is fed to a first distillation column 110 via stream 100. An entrainer-rich composition is also fed to the top stage of column 110 via stream 190. If the combined amount of fluoroolefin in streams 100 and 190 is in excess of that needed to form the low-boiling HF/fluoroolefin azeotrope, fluoroolefin is recovered essentially free of both HF and entrainer from the bottom of column 110 via stream 120. A ternary composition comprising HF, fluoroolefin, and entrainer, but enriched in fluoroolefin relative to stream 190, leaves the top of the first column as the first distillate stream 130. Stream 130 is condensed by condenser 140 forming stream 150 and mixed with a condensed second distillate stream 250 from a second distillation column. In one embodiment, additional entrainer may be added via stream 260, if needed. Combined streams 150, 250, and 260 are fed to cooler 160 and then to decanter 180 where the sub-cooled liquid stream 170 separates into entrainer-rich and HF-rich liquid phase compositions which leave the decanter via streams 190 and 200, respectively. The fluoroolefin present distributes between the two liquid phases with the majority ending up in the entrainer-rich phase. The HF-rich composition stream 200 is fed to the top stage of the second distillation column 210. Because the amount of HF in stream 200 is in excess of that needed to form a low-boiling HF/fluoroolefin azeotrope, HF is recovered as a product stream essentially free of both fluoroolefin and entrainer from the bottom of column 210 via stream 220. A ternary composition comprising HF, fluoroolefin and entrainer, but enriched in entrainer relative to stream 200, leaves the top of the second column as the second distillate stream 230. Stream 230 is condensed in condenser 240, forming stream 250, and combined with streams 150 and 260 previously described.

Alternatively, in another embodiment, rather than feed the HF/fluoroolefin mixture directly to the distillation column 110, the mixture may be fed to cooler 160 and then to decanter 180 where the mixture phase separates. Then stream 190 carries the mixture of HF, fluoroolefin and entrainer to the first distillation column 110.

In another embodiment, the concentration of HF in the HF/fluoroolefin mixture is greater than the concentration in the azeotrope of fluoroolefin and HF. Thus, in another embodiment is provided a process for the purification of HF from a mixture comprising a fluoroolefin and HF, wherein HF is present in a concentration greater than the azeotrope concentration for HF and said fluoroolefin, said process comprising:

a. adding an entrainer to the mixture comprising fluoroolefin and HF thus forming a second mixture;

b. distilling said second mixture in a first distillation step to form a first distillate composition comprising HF, entrainer, and a fluoroolefin, and a first bottoms composition comprising HF essentially free of fluoroolefin and entrainer;

c. condensing said first distillate composition to form two liquid phases, being i) an entrainer-rich phase and ii) an HF-rich phase; and d. optionally recycling the HF-rich phase back to the first distillation step. In another embodiment, the process may further comprising feeding the HF-rich phase to a second distillation step and forming a second distillate composition comprising entrainer, HF, and fluoroolefin, and a bottoms composition comprising fluoroolefin essentially free of entrainer. In another embodiment, the process may further comprise recycling said second distillate composition back to the two liquid phases.

Referring again to FIG. 2, a composition comprising HF and fluoroolefin is fed to a first distillation column 110 via stream 100. An HF-rich composition is also fed to the top stage of column 110 via stream 190. If the combined amount of HF in streams 100 and 190 is in excess of that needed to form the low-boiling HF/fluoroolefin azeotrope, HF is recovered essentially free of both fluoroolefin and entrainer from the bottom of column 110 via stream 120. A composition near the HF/fluoroolefin azeotrope with a minor amount of entrainer is recovered as the first distillate via stream 130. Stream 130 is condensed by condenser 140 forming stream 150 and mixed with a condensed second distillate stream 250 from a second distillation column. In one embodiment, additional entrainer may be added via stream 260, if needed. Combined streams 150, 250, and 260 are fed to cooler 160 and then to decanter 180 where the sub-cooled liquid stream 170 separates into HF-rich and entrainer-rich liquid phase compositions which leave the decanter via streams 190 and 200, respectively. The fluoroolefin present distributes between the two liquid phases with the majority ending up in the entrainer-rich phase. The entrainer-rich composition stream 200 is fed to the top stage of the second distillation column 210. Because the amount of fluoroolefin in stream 200 is in excess of that needed to form a low-boiling entrainer/fluoroolefin azeotrope, fluoroolefin is recovered as a product stream essentially free of both HF and entrainer from the bottom of column 210 via stream 220. A ternary composition comprising entrainer, fluoroolefin, and HF, but enriched in entrainer relative to stream 200 leaves the top of the second column as the second distillate stream 230. Stream 230 is condensed in condenser 240, forming stream 250, and combined with streams 150 and 260 previously described.

Alternatively, in another embodiment, rather than feed the HF/fluoroolefin mixture directly to the distillation column 110, the mixture may be fed to cooler 160 and then to decanter 180 where the mixture phase separates. Then stream 190 carries the mixture of HF, fluoroolefin and entrainer as the HF-rich phase to the first distillation column 110.

4. Separation of HFC-236 from HFC-1225ye and HF

HFC-1225ye is a valuable fluorocarbon useful as a refrigerant, blowing agent, aerosol propellant, and sterilant among other uses. HFC-1225ye exists as either of two isomers, HFC-Z-1225ye and HFC-E-1225ye. Hereafter, by HFC-1225ye is meant either of the two isomers and/or mixtures of the two isomers.

HFC-1225ye may be produced by dehydrofluorination of certain HFC-236 (hexafluoropropane) isomers. By HFC-236 is meant any isomer of hexafluoropropane and any combinations of any isomers of hexafluoropropane that can yield HFC-1225ye upon dehydrofluorination. Isomers of hexafluoropropane include HFC-236ea (1,1,1,2,3,3-hexafluoropropane) and HFC-236cb (1,1,1,2,2,3-hexafluoropropane).

HFC-1225ye may be prepared by the vapor phase dehydrofluorination of HFC-236ea or HFC-236cb by processes known in the art, such as those described in U.S. Pat. No. 5,396,000, U.S. Pat. No. 5,679,875, U.S. Pat. No. 6,031,141, and U.S. Pat. No. 6,369,284. For example, HFC-1225ye can be prepared by passing HFC-236ea, HFC-236cb or mixtures of HFC-236ea and HFC-236cb over a chrome oxide catalyst at elevated temperatures, for example, at above 300 deg C. The product stream from this reaction contains HFC-1225ye, HF and any unreacted HFC-236ea and/or HFC-236cb.

In one embodiment, a process is provided for the separation of HFC-1225ye from a mixture of HFC-1225ye, HF, and at least one of HFC-236ea or HFC-236cb, said process comprising:

a) subjecting said mixture to a first distillation step, wherein additional HFC-1225ye is fed from a second distillation step, to form a first distillate comprising an azeotrope of HFC-1225ye and HF and a first bottoms composition comprising at least one of HFC-236ea or HFC-236cb;

b) feeding said first distillate to a second distillation step to form a second distillate comprising an azeotrope of HFC-1225ye and HF and a second bottoms composition comprising HFC-1225ye essentially free of HF;

c) condensing said second distillate to form two liquid phases, being i) an HF-rich phase and ii) an HFC-1225ye-rich phase; and d) recycling the HFC-1225ye-rich phase from (c) back to the second distillation step. In another embodiment, the process may further comprise feeding the HF-rich phase to a third distillation step to form a third distillate comprising an azeotrope of HFC-1225ye and HF and a third bottoms composition comprising HF essentially free of HFC-1225ye.

In this embodiment the azeotropic distillation involves providing an excess of HFC-1225ye to the distillation column in addition to that produced from the dehydrofluorination reaction of HFC-236ea and/or HFC-236cb. In this embodiment, HFC-1225ye serves as an entrainer in the distillation process. If the proper total amount of HFC-1225ye is fed to the column, then all the HF may be taken overhead as an azeotrope composition containing HFC-1225ye and HF. Enough HFC-1225ye can be provided, for example, by feeding supplemental HFC-1225ye to the distillation column over that exiting in the dehydrofluorination reaction product stream. Thus, the HFC-236ea and/or HFC-236cb removed from the column bottoms may be essentially free of HF.

For example, a reactor product mixture comprising HF, HFC-1225ye and HFC-236ea may be fed to a first distillation column operated under conditions to form the HF/HFC-1225ye azeotrope with the HF/HFC-1225ye azeotrope being removed from the distillation column as the overhead distillate. The HF in this distillate may then be separated and removed from the HFC-1225ye by other means, e.g. by using pressure swing distillation or the methods as disclosed herein. Some portion of the HFC-1225ye so obtained can be recycled back to the first distillation column in quantities sufficient so that all the HF fed to the first distillation column is removed from that column as the HF/HFC-1225ye azeotrope, thus producing a HFC-236ea bottoms stream essentially free of HF.

Where the composition to be separated is formed by dehydrohalogenating either of HFC-236ea or HFC-236cb, it is desirable to recycle any unreacted HFC-236ea or HFC-236cb back to the reactor so that they may be converted to HFC-1225ye. However, it is necessary that HF and HFC-1225ye be removed from said unreacted HFC-236ea or HFC-236cb prior to being recycled so as not to inhibit the equilibrium reaction. It is also necessary that the HF be removed from the HFC-1225ye to allow its use as a refrigerant or in other applications.

Figure 3:
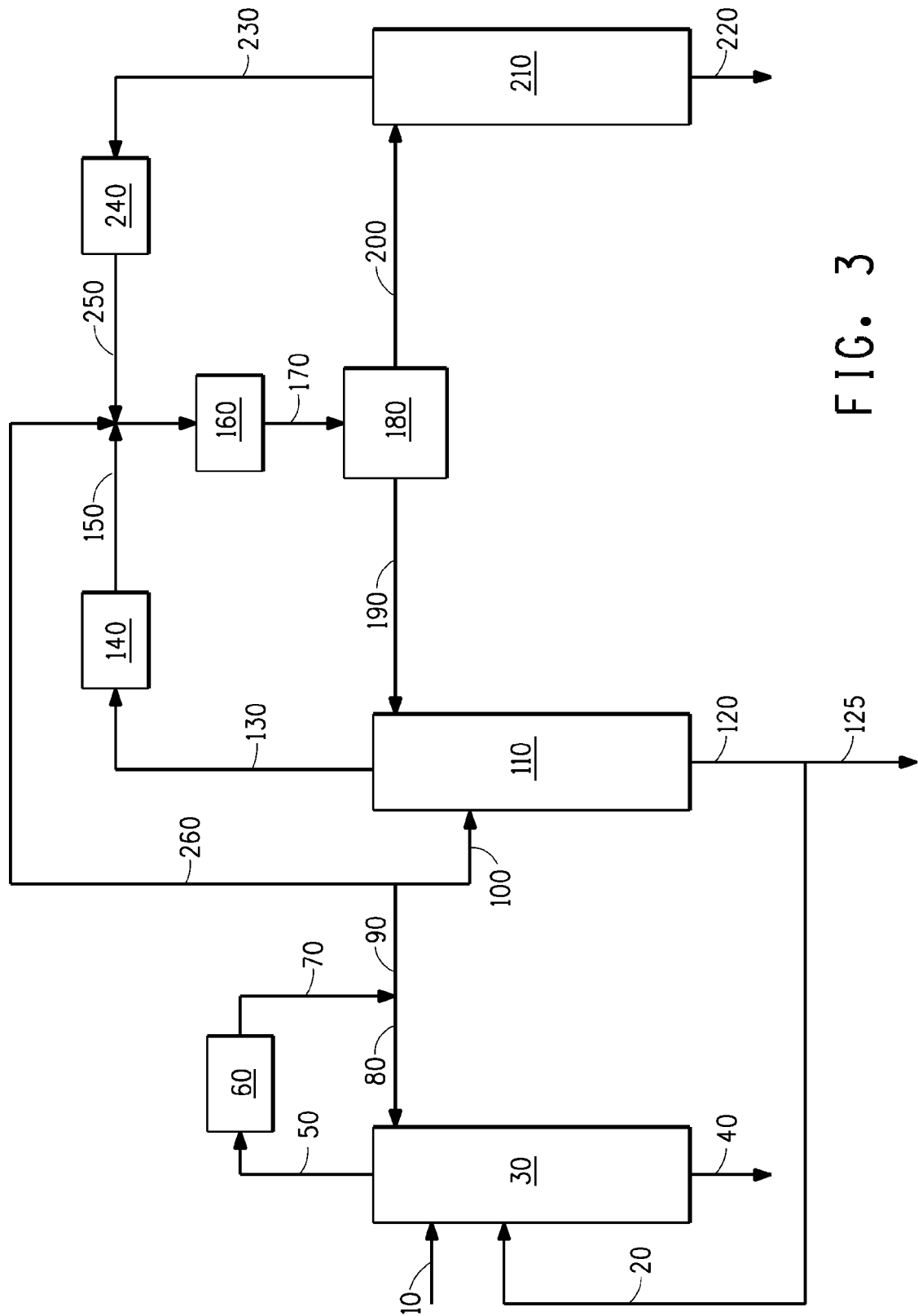
FIG. 3 is an illustration of one embodiment of a process to separate at least one of HFC-236ea and HFC-236cb from a mixture comprising HFC-1225ye, HF and said at least one of HFC-236ea and HFC-236cb via azeotropic distillation wherein HFC-1225ye acts as an entrainer followed by a process in which HFC-1225ye and HF are separated from a mixture comprising HFC-1225ye and HF, but now substantially free of HFC-236ea and/or HFC-236cb, by azeotropic distillation without the addition of another chemical compound to function as an entrainer.

Referring now to FIG. 3, a stream comprising HF, HFC-1225ye, and at least one of HFC-236ea and HFC-236cb is fed to a first distillation column via stream 10, with the column operated under conditions to approach the low-boiling HF/HFC-1225ye azeotrope, which is removed as distillate via streams 50, 70, and 90. Enough supplemental HFC-1225ye is recycled from the second column bottoms to this first column via stream 20 to enable all of the HF to be removed from the HFC-236cb and/or HFC-236ea. The HFC-236cb and/or HFC-236ea are obtained essentially free of HFC-1225ye and HF as the bottoms product from this column via stream 40.

The near HF/HFC-1225ye azeotropic composition in stream 50 is condensed and divided into reflux 80 and distillate 90 streams. Distillate stream 90 may be fed to a second distillation column 110 via stream 100 as shown and indicated, mixed with distillate streams 150 and 250 from the second and third columns, respectively, and sent to cooler 160 and decanter 180, or be divided between these two destinations. Because of the desire to remove all of the HF overhead in column 30, excess HFC-1225ye would be recycled to column 30, making the composition of streams 50, 70, 80, 90, and 100 lie on the HFC-1225ye-rich side of the azeotrope. Therefore, if distillate stream 90 is sent via stream 100 to a second distillation column, it should be sent to the column which produces purified HFC-1225ye as the bottoms product.

In one embodiment, distillate stream 90 via stream 260 is mixed with distillate streams 150 and 250 from the second and third columns, respectively, and sent to cooler 160, forming sub-cooled stream 170, which is fed to decanter 180. In the decanter, stream 170 separates into HFC-1225ye-rich and HF-rich liquid fractions, which are removed as streams 190 and 200. The HFC-1225ye-rich stream from the decanter is fed via stream 190 to a second distillation column 110 containing 19 theoretical stages and operated under conditions to approach the HFC-1225ye/HF azeotrope, which is distilled overhead as distillate stream 130, condensed in condenser 140, and mixed with the distillates from the first and third columns via stream 150. Column 110 produces a bottoms stream of HFC-1225ye essentially free of HF via stream 120. Part of the HFC-1225ye bottoms stream 120 is recycled to the first column via stream 20, as previously described, and the rest becomes the purified HFC-1225ye product removed via stream 125. The HF-rich stream from the decanter is fed via stream 200 to a third distillation column 210 operated under conditions to approach the HFC-1225ye/HF azeotrope, which is distilled overhead as distillate as stream 230 which is condensed in condenser 250 and mixed with the distillates from the first and second columns via stream 250. Column 210 produces a bottoms stream of HF essentially free of HFC-1225ye via stream 220.

In another aspect of this invention, an entrainer may be added to enable separation of the HF from the HFC-1225ye, or of the HF from the HFC-1225ye and HFC-236ea and/or HFC-236cb.

For example, the mixture of HF, HFC-1225ye, HFC-236ea and/or HFC-236cb may be formed by any practical means, such as by feeding at least one of HFC-236cb or HFC-236ea over a chrome oxide catalyst at elevated temperature. The mixture of HF, HFC-1225ye, HFC-236ea and/or HFC-236cb may be fed to a distillation column. A suitable entrainer is then also fed to the distillation column, either as a separate stream or by being mixed in with the HF/HFC-1225ye/HFC-236cb and/or HFC-236ea mixture prior to feeding it to the distillation column. The distillation column is then operated under conditions sufficient to form a low-boiling azeotrope composition between the entrainer and HF, with the HF and entrainer removed as the column distillate, and the HFC-1225ye, HFC-236ea and/or HFC-236cb recovered from the column bottoms essentially free of HF. The HFC-1225ye may then be separated from the HFC-236ea and/or HFC-236cb by any usual means including conventional distillation, with the HFC-1225ye being recovered as product and with the HFC-236ea and/or HFC-236cb optionally being recycled back to the reaction step to produce HFC-1225ye.

Thus in another embodiment is provided a process for separating HF from a mixture comprising HFC-1225ye, HF, and at least one of HFC-236ea or HFC-236cb. The process comprises:

a. adding an entrainer to the mixture comprising HFC-1225ye, HF, and at least one of HFC-236ea or HFC-236cb thus forming a second mixture;

b. distilling said second mixture in a first distillation step to form a first distillate composition comprising HF and entrainer and a first bottoms composition comprising HFC-1225ye and at least one of HFC-236ea or HFC-236cb;

c. condensing said first distillate composition to form two liquid phases, being (i) an entrainer-rich phase and (ii) an HF-rich phase; and d. recycling the entrainer-rich phase back to the first distillation step.

In another embodiment, the process may further comprise feeding the HF-rich phase to a second distillation step and forming a second distillate composition comprising an azeotrope of entrainer and HF and a second bottoms composition comprising HF essentially free of entrainer. In another embodiment, the process may further comprise recycling said second distillate composition back to the two liquid phases.

Figure 4:
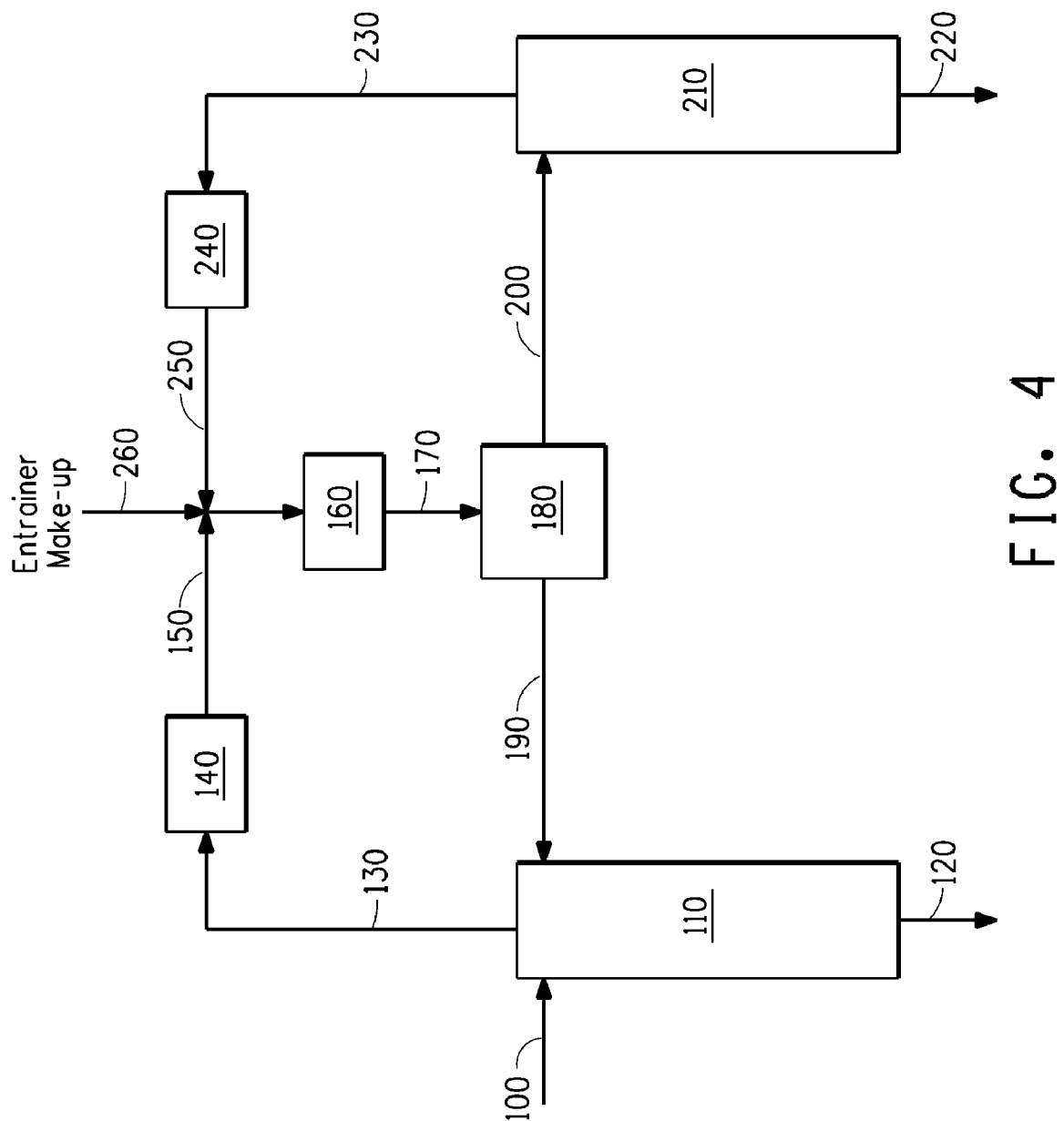
FIG. 4 is an illustration of one embodiment of a process to separate HFC-1225ye and at least one of HFC-236ea and HFC-236cb from a mixture comprising HFC-1225ye, HF and said at least one of HFC-236ea and HFC-236cb via azeotropic distillation wherein a supplemental entrainer is fed to the distillation.

Referring now to FIG. 4, a stream comprising HF, HFC-1225ye, and at least one of HFC-236ea or HFC-236cb is fed to a first distillation column 110 via stream 100. An entrainer-rich stream is also fed to this column via stream 190. Column 110 is operated under conditions to cause HF to distill overhead with the entrainer due to the influence of the low-boiling HF/entrainer azeotrope. Sufficient entrainer is fed to this first column via stream 190 such that HFC-1225ye and HFC-236ea or HFC-236cb may be obtained essentially free of entrainer and HF as the bottoms from column 110 via stream 120. The HFC-1225ye and HFC-236ea or HFC-236cb in stream 120 may then optionally be separated from each other by conventional distillation and the HFC-236ea or HFC-236cb optionally recycled back to a dehydrofluorination reactor to form HFC-1225ye. The distillate from column 110, removed via stream 130, contains essentially all of the entrainer and HF in column feeds 100 and 190 and, optionally, some HFC-236ea or HFC-236cb and/or HFC-1225ye. This first distillate stream 130 is condensed by condenser 140 to form stream 150, which is then mixed with condensed distillate stream 250 from the second distillation column and, as needed, additional fresh entrainer added via stream 260. This combined stream is sub-cooled by cooler 160 and sent via stream 170 to decanter 180 where it separates into separate entrainer-rich and HF-rich liquid fractions which are removed via streams 190 and 200, respectively. The majority of the HFC-236ea or HFC-236cb and HFC-1225ye present in the decanter partition into the entrainer-rich phase fraction. The entrainer-rich fraction is fed to the first distillation column 110 via stream 190. The HF-rich fraction from the decanter is fed via stream 200 to a second distillation column 210 containing 8 theoretical stages and operated under conditions such that a bottoms stream of HF essentially free of HFC-236ea or HFC-236cb, HFC-1225ye, and entrainer is produced and removed via stream 220. The distillate from column 210, removed via stream 230 and containing essentially all of the HFC-236ea or HFC-236cb, HFC-1225ye, and entrainer present in the column feed (stream 200) plus the HF not recovered in product stream 220, is condensed by condenser 240 and removed via stream 250. Condensed distillate stream 250 is combined with both the condensed distillate stream 150 from the first column and, as needed, fresh entrainer, added via stream 260, then cooled and fed to the decanter for further separation.

In another embodiment, a hydrofluorocarbon (HFC), which forms a homogeneous azeotrope with HF, can be separated from a mixture comprising HF, the HFC and a fluoroolefin by azeotropic distillation using the fluoroolefin as an entrainer, followed by separation of the fluoroolefin and HF by azeotropic distillation using an added compound as the entrainer. HF and the fluoroolefin are not required to be partially miscible at reduced temperatures for such a separation process to work as long as the HF-fluoroolefin azeotrope has a lower boiling point than the HF-HFC azeotrope. For illustration purposes, the fluoroolefin is HFC-1225ye and the HFC is HFC-236ea and/or HFC-236cb.

Figure 5:
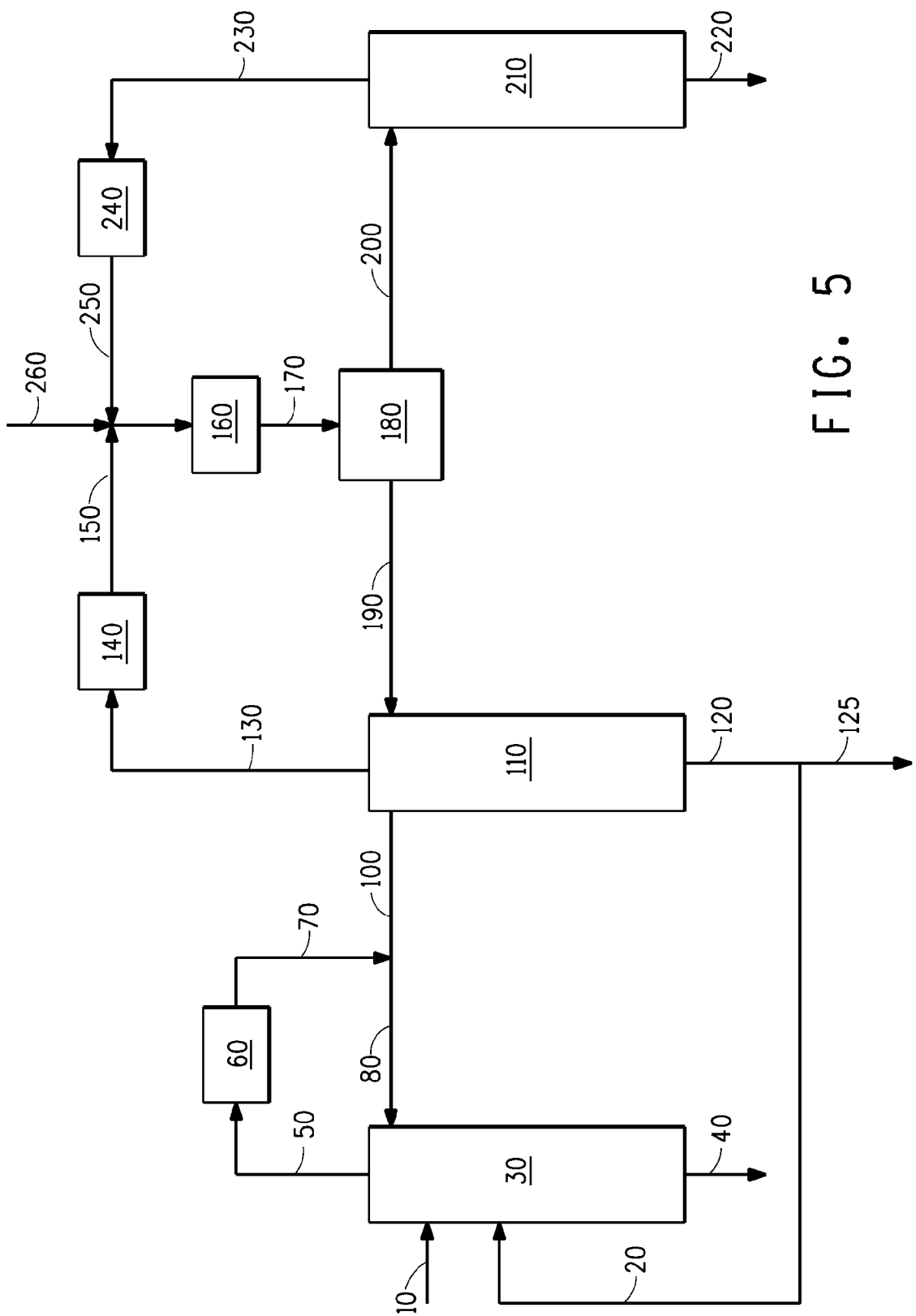
FIG. 5 is an illustration of one embodiment of a process to separate at least one of HFC-236ea and HFC-236cb from a mixture comprising HFC-1225ye, HF and said at least one of HFC-236ea and HFC-236cb via azeotropic distillation wherein HFC-1225ye acts as an entrainer followed by a process in which HFC-1225ye and HF are separated from a mixture comprising HFC-1225ye and HF, but now substantially free of HFC-236ea and/or HFC-236cb, by azeotropic distillation with an added entrainer.

Referring now to FIG. 5, a stream comprising HF, HFC-1225ye, and at least one of HFC-236ea and HFC-236cb is fed to a first distillation column 30 via stream 10, with the column operated under conditions to approach the low-boiling HF/HFC-1225ye azeotrope, which is removed as distillate via streams 50, 70, and 100. This first column can be designed and operated in such a way that the near azeotropic distillate is essentially free of HFC-236ea and/or HFC-236cb. By recycling enough supplemental HFC-1225ye from the second column bottoms to the first column via stream 20, essentially all of the HF can be distilled overhead as the HF/HFC-1225ye azeotrope such that HFC-236cb and/or HFC-236ea are obtained essentially free of HFC-1225ye and HF as the bottoms product from column 30 via stream 40. The HFC-236ea and/or HFC-236cb may then optionally be recycled back to a reactor for production of HFC-1225ye, or may be further purified and then recycled. This demonstrates the use of the fluoroolefin as an entrainer to remove HF from an HFC.

As described for FIG. 3, the distillate from the first column may be fed to a second distillation column, mixed with the distillate streams from a second and third column, cooled, and then sent to a decanter, or split between these two destinations. In this embodiment, the distillate from the first column 30 is fed via stream 100 to a second column 110. An entrainer-rich stream is also fed to this second column via stream 190. Distillation column 110 is operated under conditions such that the distillate, removed via stream 130, contains essentially all of the entrainer and HF in the column feeds 100 and 190 and produces an HFC-1225ye bottoms product essentially free of HF and entrainer which is removed via stream 120. Part of the HFC-1225ye bottoms stream 120 is recycled to the first column via stream 20, as previously described, and the rest becomes the purified HFC-1225ye product removed via stream 125. Distillate stream 130 is condensed by condenser 140 to form stream 150, which is then mixed with the condensed distillate stream 250 from the second distillation column and, as needed, fresh entrainer added via stream 260. This combined stream is cooled by cooler 160 and sent via stream 170 to decanter 180 where it separates into separate entrainer-rich and HF-rich liquid fractions, which are removed via streams 190 and 200, respectively. The majority of the HFC-1225ye present in the decanter partitions into the entrainer-rich phase fraction. The decanter entrainer-rich fraction is fed to column 110 via stream 190. The decanter HF-rich fraction is fed, via stream 200, to a third distillation column 210 operated under conditions which produce a bottoms product consisting of HF essentially free of HFC-1225zc and the entrainer, which is removed via stream 220. The distillate from column 210, which is removed via stream 230 and contains essentially all of the HFC-1225ye and entrainer present in the column feed (stream 200) and any HF not recovered in product stream 220, is condensed by condenser 240, forming stream 250. Condensed distillate stream 250 is combined with both the condensed distillate stream 150 from the second column and, as needed, fresh entrainer, added via stream 260, then cooled and fed to the decanter via stream 170 for further separation.

In one embodiment, entrainers for HF separation from HFC-1225ye and optionally HFC-236ea and/or HFC-236cb include: CFC-115 (chloropentafluoroethane), CFC-114 (1,2-dichloro-1,1,2,2-tetrafluoroethane), CFC-114a (1,1-dichloro-1,2,2,2-tetrafluoroethane), HCFC-21 (dichlorofluoromethane), HCFC-124 (1-chloro-1,2,2,2-tetrafluoroethane), HCFC-124a (1-chloro-1,1,2,2-tetrafluoroethane), HCFC-133a (1-chloro-2,2,2-trifluoroethane), HCFC-142b (1-chloro-1,1-difluoroethane), HCFC-1122 (1-chloro-2,2-difluoroethylene), HFC-1234ze (1,3,3,3-tetrafluoro-1-propene), HFC-1123 (trifluoroethylene), HFC-1234yf (2,3,3,3-tetrafluoro-1-propene), PFC-218 (octafluoroethane), PFC-C216 (trifluorocyclopropane), cis- and trans-PFC-1318 (octafluoro-2-butene), PFC-1216 (hexafluoropropene, HFP), PFC-C318 (octafluorocyclobutane), PFC-31-10my (decafluorobutane), PFC-2316 (hexafluorobutadiene), PEVE (perfluoroethylvinyl ether), PMVE (perfluoromethylvinyl ether), $SF_6$ (sulfur hexafluoride), $Cl_2$ (Chlorine), Cyclopropane, $C_2H_6$ (Ethane), propane, n-butane, isobutane, 2,2-dimethylpropane, 1-butene, isobutene, 1,3-butadiene, cis- and trans-2-butene, 1-butyne, vinylacetylene, hexafluoroacetone, 1,1-difluorodimethyl ether, pentafluoroethylmethyl ether, tetrafluorodimethyl ether, and mixtures thereof. In another embodiment, the entrainers that are effective for separation of HF from HFC-1225ye include n-propane and ethane.

5. Other Fluoroolefins and Separation Processes Utilizing Azeotropes with HF

Other fluoroolefin/HF azeotropes have been disclosed that may be used in separation processes as described herein for HFC-1225ye and HFC-236.

U.S. Patent Publication no. 2007-0100173 A1 discloses the azeotrope and azeotrope-like (also known as near-azeotrope) compositions for HFC-1234ze (1,3,3,3-tetrafluoropropene) and HF. These azeotrope and azeotrope-like compositions may be used in processes for separating a fluoroolefin from a mixture comprising HF and fluoroolefin. Additionally, as HFC-1234ze may be prepared by dehydrofluorination of HFC-245fa (1,1,1,3,3-pentafluoropropane) or HFC-245eb (1,1,1,2,3-pentafluoropropane) the compositions as described therein may be used in similar methods for separation or purification of HFC-1234ze from mixtures comprising HFC-1234ze, HF and at least one of HFC-245fa or HFC-245eb.

In another embodiment, a process is provided for the separation of HFC-1234ze from a mixture of HFC-1234ze, HF, and at least one of HFC-245fa or HFC-245eb, said process comprising:

a) subjecting said mixture to a first distillation step, wherein additional HFC-1234ze is fed from a second distillation step, to form a first distillate comprising an azeotrope of HFC-1234ze and HF and a first bottoms composition comprising at least one of HFC-245fa or HFC-245eb;

b) feeding said first distillate to a second distillation step to form a second distillate comprising an azeotrope of HFC-1234ze and HF and a second bottoms composition comprising HFC-1234ze essentially free of HF;

c) condensing said second distillate to form two liquid phases, being i) an HF-rich phase and ii) an HFC-1234ze-rich phase; and d) recycling the HFC-1234ze-rich phase from (c) back to the first distillation step. In another embodiment, the process may further comprise feeding the HF-rich phase to a third distillation step to form a third distillate comprising an azeotrope of HFC-1234ze and HF and a third bottoms composition comprising HF essentially free of HFC-1234ze.

In another embodiment is provided a process for separating HF from a mixture comprising HFC-1234ze, HF, and at least one of HFC-245fa or HFC-245eb. The process comprises:
  a. adding an entrainer to the mixture comprising HFC-1234ze, HF, and at least one of HFC-245fa or HFC-245eb thus forming a second mixture;
  b. distilling said second mixture in a first distillation step to form a first distillate composition comprising HF and entrainer and a first bottoms composition comprising HFC-1234ze and at least one of HFC-245fa or HFC-245eb;
  c. condensing said first distillate composition to form two liquid phases, being (i) an entrainer-rich phase and (ii) an HF-rich phase; and
  d. recycling the entrainer-rich phase back to the first distillation step.

In another embodiment, the process may further comprising feeding the HF-rich phase to a second distillation step and forming a second distillate composition comprising an azeotrope of entrainer and HF and a second bottoms composition comprising HF essentially free of entrainer. In another embodiment, the process may further comprising recycling said second distillate composition back to the two liquid phases.

U.S. Patent Publication no. 2007-0100175 A1 discloses the azeotrope and azeotrope-like (also known as near-azeotrope) compositions for HFC-1234yf (2,3,3,3-tetrafluoropropene) and HF. These azeotrope and azeotrope-like compositions may be used in processes for separating a fluoroolefin from a mixture comprising HF and fluoroolefin. Additionally, as HFC-1234yf may be prepared by dehydrofluorination of HFC-245cb (1,1,1,2,2-pentafluoropropane) or HFC-245eb (1,1,1,2,3-pentafluoropropane) the compositions as described therein may be used in similar methods for separation or purification of HFC-1234yf from mixtures comprising HFC-1234yf, HF and at least one of HFC-245cb or HFC-245eb.

In another embodiment, a process is provided for the separation of HFC-1234yf from a mixture of HFC-1234yf, HF, and at least one of HFC-245cb or HFC-245eb, said process comprising:
  a) subjecting said mixture to a first distillation step, wherein additional HFC-1234yf is fed from a second distillation step, to form a first distillate comprising an azeotrope of HFC-1234yf and HF and a first bottoms composition comprising at least one of HFC-245cb or HFC-245eb;
  b) feeding said first distillate to a second distillation step to form a second distillate comprising an azeotrope of HFC-1234yf and HF and a second bottoms composition comprising HFC-1234yf essentially free of HF;
  c) condensing said second distillate to form two liquid phases, being i) an HF-rich phase and ii) an HFC-1234yf-rich phase; and
  d) recycling the HFC-1234yf-rich phase from (c) back to the first distillation step. In another embodiment, the process may further comprise feeding the HF-rich phase to a third distillation step to form a third distillate comprising an azeotrope of HFC-1234yf and HF and a third bottoms composition comprising HF essentially free of HFC-1234yf.

In another embodiment, a process is provided for separating HF from a mixture comprising HFC-1234yf, HF, and at least one of HFC-245cb or HFC-245eb. The process comprises:
  a. adding an entrainer to the mixture comprising HFC-1234yf, HF, and at least one of HFC-245cb or HFC-245eb thus forming a second mixture;
  b. distilling said second mixture in a first distillation step to form a first distillate composition comprising HF and entrainer and a first bottoms composition comprising HFC-1234yf and at least one of HFC-245cb or HFC-245eb;
  c. condensing said first distillate composition to form two liquid phases, being (i) an entrainer-rich phase and (ii) an HF-rich phase; and
  d. recycling the entrainer-rich phase back to the first distillation step.

In another embodiment, the process may further comprise feeding the HF-rich phase to a second distillation step and forming a second distillate composition comprising an azeotrope of entrainer and HF and a second bottoms composition comprising HF essentially free of entrainer. In another embodiment, the process may further comprise recycling said second distillate composition back to the two liquid phases.

U.S. Patent Publication no. US2007-0099811 A1 discloses the azeotrope and azeotrope-like (also known as near-azeotrope) compositions for HFC-1429 (nonafluoropentene) and HF. These azeotrope and azeotrope-like compositions may be used in processes for separating a fluoroolefin from a mixture comprising HF and fluoroolefin. Additionally, as HFC-1429 may be prepared by dehydrofluorination of HFC-43-10mee (1,1,1,2,3,4,4,5,5,5-decafluoropentane) the compositions as described therein may be used in similar methods for separation or purification of HFC-1429 from mixtures comprising HFC-1429, HF and HFC-43-10mee.

In one embodiment, a process is provided for the separation of HFC-1429 from a mixture of HFC-1429, HF, and HFC-43-10mee, said process comprising:
  a) subjecting said mixture to a first distillation step, wherein additional HFC-1429 is fed from a second distillation step, to form a first distillate comprising an azeotrope of HFC-1429 and HF and a first bottoms composition comprising HFC-43-10mee;
  b) feeding said first distillate to a second distillation step to form a second distillate comprising an azeotrope of HFC-1429 and HF and a second bottoms composition comprising HFC-1429 essentially free of HF;
  c) condensing said second distillate to form two liquid phases, being i) an HF-rich phase and ii) an HFC-1429-rich phase; and
  d) recycling the HFC-1429-rich phase from (c) back to the first distillation step. In another embodiment, the process may further comprise feeding the HF-rich phase to a third distillation step to form a third distillate comprising an azeotrope of HFC-1429 and HF and a third bottoms composition comprising HF essentially free of HFC-1429.

In one embodiment, a process is provided for separating HF from a mixture comprising HFC-1429, HF, and HFC-43-10mee. The process comprises:
  a. adding an entrainer to the mixture comprising HFC-1429, HF, and HFC-43-10mee thus forming a second mixture;
  b. distilling said second mixture in a first distillation step to form a first distillate composition comprising HF and entrainer and a first bottoms composition comprising HFC-1429 and HFC-43-10mee;
  c. condensing said first distillate composition to form two liquid phases, being (i) an entrainer-rich phase and (ii) an HF-rich phase; and
  d. recycling the entrainer-rich phase back to the first distillation step.

In another embodiment, the process may further comprise feeding the HF-rich phase to a second distillation step and forming a second distillate composition comprising an azeotrope of entrainer and HF and a second bottoms composition comprising HF essentially free of entrainer. In another embodiment, the process may further comprising recycling said second distillate composition back to the two liquid phases.

U.S. Patent Publication no. 2006-0116538 A1 discloses the azeotrope and azeotrope-like (also known as near-azeotrope) compositions for HFC-1225zc (1,1,3,3,3-pentafluoropropene) and HF. These azeotrope and azeotrope-like compositions may be used in processes for separating a fluoroolefin from a mixture comprising HF and fluoroolefin. Additionally, as HFC-1225zc may be prepared by dehydrofluorination of HFC-236fa (1,1,1,3,3,3-hexafluoropropane) or HFC-236ea (1,1,1,2,3,3-hexafluoropropane) the compositions as described therein may be used in similar methods for separation or purification of HFC-1225zc from mixtures comprising HFC-1225zc, HF and at least one of HFC-236fa or HFC-236ea.

In one embodiment, a process is provided for the separation of HFC-1225zc from a mixture of HFC-1225zc, HF, and at least one of HFC-236fa or HFC-236ea, said process comprising:

a) subjecting said mixture to a first distillation step, wherein additional HFC-1225zc is fed from a second distillation step, to form a first distillate comprising an azeotrope of HFC-1225zc and HF and a first bottoms composition comprising at least one of HFC-236fa or HFC-236ea;

b) feeding said first distillate to a second distillation step to form a second distillate comprising an azeotrope of HFC-1225zc and HF and a second bottoms composition comprising HFC-1225zc essentially free of HF;

c) condensing said second distillate to form two liquid phases, being i) an HF-rich phase and ii) an HFC-1225zc-rich phase; and d) recycling the HFC-1225zc-rich phase from (c) back to the first distillation step. In another embodiment, the process may further comprise feeding the HF-rich phase to a third distillation step to form a third distillate comprising an azeotrope of HFC-1225zc and HF and a third bottoms composition comprising HF essentially free of HFC-1225zc.

In one embodiment, a process is provided for separating HF from a mixture comprising HFC-1225zc, HF, and at least one of HFC-236fa or HFC-236ea. The process comprises:

a. adding an entrainer to the mixture comprising HFC-1225zc, HF, and at least one of HFC-236fa or HFC-236ea thus forming a second mixture;

b. distilling said second mixture in a first distillation step to form a first distillate composition comprising HF and entrainer and a first bottoms composition comprising HFC-1225zc and at least one of HFC-236fa or HFC-236ea;

c. condensing said first distillate composition to form two liquid phases, being (i) an entrainer-rich phase and (ii) an HF-rich phase; and d. recycling the entrainer-rich phase back to the first distillation step.

In another embodiment, the process may further comprise feeding the HF-rich phase to a second distillation step and forming a second distillate composition comprising an azeotrope of entrainer and HF and a second bottoms composition comprising HF essentially free of entrainer. In another embodiment, the process may further comprise recycling said second distillate composition back to the two liquid phases.

EXAMPLES

The concepts described herein will be further described in the following examples, which do not limit the scope of the invention described in the claims.

Example 1

Dehydrofluorination of HFC-236ea to HFC-1225ye (E and Z Isomers) Over Carbonaceous Catalyst To a Hastelloy nickel alloy reactor (1.0" OD×0.854" ID×9.5" L) was charged 14.32 g (25 mL) of spherical (8 mesh) three dimensional matrix porous carbonaceous material prepared substantially as described in U.S. Pat. No. 4,978,649. The packed portion of the reactor was heated by a 5"×1" ceramic band heater clamped to the outside of the reactor. A thermocouple, positioned between the reactor wall and the heater measured the reactor temperature. After charging the reactor with the carbonaceous material, nitrogen (10 mL/min) was passed through the reactor and the temperature was raised to 200° C. during a period of one hour and maintained at this temperature for an additional 4 hours. The reactor temperature was then raised to the desired operating temperature and a flow of HFC-236ea and nitrogen was started through the reactor.

A portion of the total reactor effluent was sampled on-line for organic product analysis using a gas chromatograph equipped with a mass selective detector (GC-MS). The bulk of the reactor effluent containing organic products and also inorganic acid, such as HF, was treated with aqueous caustic for neutralization.

The results obtained in GC mole percent are summarized in Table 3.

TABLE 4

| Reactor Temp. (° C.) | 236ea feed (mL/min) | $N_2$ feed (mL/min) | Mole Percent | | | |
|---|---|---|---|---|---|---|
| | | | Z-1225ye | E-1225ye | 236ea | Unknowns |
| 200 | 10 | 20 | 0.03 | ND | 99.97 | ND |
| 250 | 10 | 20 | 0.2 | 0.03 | 99.8 | ND |
| 300 | 10 | 20 | 1.4 | 0.22 | 98.4 | 0.01 |
| 350 | 10 | 20 | 5.4 | 0.96 | 93.1 | 0.5 |
| 400 | 10 | 20 | 38.1 | 9.0 | 51.7 | 1.1 |
| 400 | 10 | 10 | 37.9 | 8.7 | 51.6 | 1.8 |
| 400 | 10 | 5 | 42.6 | 9.5 | 46.7 | 1.2 |
| 400 | 10 | 40 | 13.2 | 2.5 | 71.6 | 12.7 |

ND = not detected

Example 2

Azeotropic Distillation for the Separation of HFC-1225ye from HF without an Entrainer Example 2 demonstrates that HF may be separated from HFC-1225ye by azeotropic distillation with no entrainer. Referring now to FIG. 1, a composition comprising HF and HFC-1225ye is fed to a first column 110 via stream 100. This first column contains 8 theoretical stages and is operated under appropriate conditions to approach the low-boiling HF/HFC-1225ye azeotrope. Because HF is being fed to this first column in excess of that needed to form the azeotrope with the HFC-1225ye, HF is recovered as a product stream out the bottoms of the column via stream 120, while a composition near to the HF/HFC-1225ye azeotrope is recovered as distillate via stream 130. Stream 130 is condensed in 140, mixed with the nearly azeotropic composition recycled from the second column via stream 250 and the combined stream is sub-cooled in cooler 160 and sent to decanter 180 where the combined stream 170 separates into separate HF-rich (190) and HFC-1225ye-rich (200) streams. Stream 190 is recycled to the first column as reflux. Stream 200 is fed to the top stage of a second distillation column 210, containing 19 theoretical stages and operated under conditions to approach the HF/HFC-1225ye azeotrope. Because HFC-1225ye is being fed to this second column in excess of that needed to form the low-boiling HF/HFC-1225ye azeotrope, HFC-1225ye is recovered as a product stream out the bottoms of the column via stream 220 while a composition close to the HF/HFC-1225ye azeotrope is recovered as distillate via stream 230. Stream 230 is condensed in 240, mixed with the nearly azeotropic composition from the first column via stream 150 and fed to cooler 160 and then decanter 180.

The data in Table 5 were calculated using measured and calculated thermodynamic properties.

theoretical stages via stream 100. An HF-rich and propane-lean composition is also fed to the top stage of column 110 via stream 190. Because the combined amount of HF in streams 100 and 190 is in excess of that needed to form the low-boiling HF/HFC-1225ye azeotrope, HF is recovered as a product stream essentially free of both HFC-1225ye and propane from the bottom of column 110 via stream 120. A composition near the HF/HFC-1225ye azeotrope is recovered as the distillate via stream 130. Stream 130 is condensed by condenser 140 forming stream 150 and mixed with both the condensed distillate stream 250 from a second distillation column and, as needed, additional propane added via stream 260. Combined streams 150, 250, and 260 are sent to cooler 160 and then to decanter 180 where the sub-cooled liquid stream 170 separates into HF-rich and propane-rich liquid phase fractions which are removed via streams 190 and 200, respectively. The HFC-1225ye present in the decanter primarily distributes into the propane-rich liquid phase fraction. Stream 190 is recycled to the first column. The HF-lean liquid phase fraction in the decanter is fed to the top stage of a second distillation column 210 via stream 200. Because the amount of HFC-1225ye in stream 200 is in excess of that needed to form the low-boiling propane/HFC-1225ye, HFC-1225ye/HF, and propane/HFC-1225ye/HF azeotropes, i.e., the composition of stream 200 lies in the distillation region bounded by these three azeotrope compositions and pure HFC-1225ye, HFC-1225ye is recovered as a product stream essentially free of both HF and propane from the bottom of column 210 via stream 220. A ternary composition enriched in propane relative to stream 200 and in the same distillation region leaves the top of the second column as the distillate via stream 230. Stream 230 is condensed by condenser 240, forming stream 250, and combined with streams 150 and 260 as previously described.

The data in Table 6 were calculated using measured and calculated thermodynamic properties

TABLE 5

| Component or variable | First dist. col. feed | First column distillate | First dist. col. bottom (HF product) | HF rich phase (from decanter) | HFC-1225ye rich phase (from decanter) | Second distillate | Second dist. col. Bottom (HFC-1225ye product) |
|---|---|---|---|---|---|---|---|
| Stream No. | 100 | 130 | 120 | 190 | 200 | 230 | 220 |
| HF, wt % | 13.2 | 8.1 | 100 | 40.8 | 1.3 | 7.5 | 1 ppm |
| HFC-1225ye, wt % | 86.8 | 91.9 | 10 ppm | 59.2 | 98.7 | 92.5 | 100 |
| Temp, ° C. | 30.0 | 46.8 | 102.2 | −40.0 | −40.0 | 46.6 | 53.2 |
| Pres, psia (kPa) | 165 | 160 | 160 | 159 | 159 | 160 | 160 |

Example 3

Azeotropic Distillation for the Separation of HFC-1225ye from HF Using Propane as the Entrainer Example 3 demonstrates that HF may be separated from HFC-1225ye by azeotropic distillation using propane as the entrainer. This ternary mixture forms three minimum-boiling binary azeotropes and a minimum-boiling ternary azeotrope.

Referring now to FIG. 2, a composition consisting of HF and HFC-1225ye is fed to a first column 110 containing 8

TABLE 6

| Component or variable | First dist. col. feed | First distillate | First dist. col. bottom (HF product) | HF rich phase (from decanter) | Propane rich phase (from decanter) | Second distillate | Second dist. col. Bottom (HFC-1225ye product) |
|---|---|---|---|---|---|---|---|
| Stream No. | 100 | 130 | 120 | 190 | 200 | 230 | 220 |
| HF, wt % | 13.2 | 8.1 | 100 | 39.2 | 0.6 | 0.9 | <1 ppm |
| HFC-1225ye, wt % | 86.8 | 91.7 | 1 ppm | 59.5 | 84.7 | 77.4 | 100 |

TABLE 6-continued

| Component or variable | First dist. col. feed | First distillate | First dist. col. bottom (HF product) | HF rich phase (from decanter) | Propane rich phase (from decanter) | Second distillate | Second dist. col. Bottom (HFC-1225ye product) |
|---|---|---|---|---|---|---|---|
| Propane, wt % | 0 | 0.2 | <1 ppm | 1.3 | 14.7 | 21.7 | 10 ppm |
| Temp, ° C. | 25.0 | 16.4 | 66.6 | −20.0 | −20.0 | 11.6 | 20.8 |
| Pres, psia (kPa) | 115 | 65 | 65 | 65 | 65 | 65 | 65 |

Example 4

Azeotropic Distillation for Separating HFC-1225ye and HF from HFC-236ea

A mixture of HF, HFC-1225ye, and HFC-236ea is fed to a distillation column for the purpose of purification of the HFC-236ea. HFC-236ea and HF form a low-boiling azeotrope which does not separate into two liquid phases and which prevents all of the HF from being removed from mixtures comprising HFC-236ea by ordinary fractional distillation. The boiling temperature of the HF/HFC-236ea azeotrope is higher than that of the HF/HFC-1225ye azeotrope. The distillation column in this example is operated under conditions to form a composition approaching that of the low-boiling HF/HFC-1225ye azeotrope at the top of the column. However, in this example, there is insufficient HFC-1225ye present to remove all of the HF in the distillate at the near HF/HFC-1225ye azeotrope composition. Consequently, some HF remains with the HFC-236ea exiting the column bottoms.

The data in Table 7 were obtained by calculation using measured and calculated thermodynamic properties.

TABLE 7

| Component or variable | Column feed | Column overhead (distillate) | Column bottoms |
|---|---|---|---|
| HFC-236ea, mol % | 33.4 | 1 ppm | 66.0 |
| HFC-1225ye, mol % | 33.3 | 67.4 | 180 ppm |
| HF, mol % | 33.3 | 32.6 | 34.0 |
| Temp, ° C. | — | −10.0 | 13.8 |
| Pressure, psi (kPa) | — | 24.7 (170) | 26.7 (184) |

Example 5

Azeotropic Distillation for Separating HFC-1225ye and HF from HFC-236ea

A mixture of HF, HFC-1225ye, and HFC-236ea is fed to a distillation column for the purpose of purification of the HFC-236ea. The distillation column in this example is operated under conditions to form a composition approaching that of the low-boiling HF/HFC-1225ye azeotrope at the top of the column. In contrast to Example 4, there is enough HFC-1225ye present in the feed mixture such that all of the HF exits in the distillate at a composition close to the HF/HFC-1225ye azeotrope, leaving the HFC-236ea obtained as column bottoms essentially free of HF.

The data in Table 8 were obtained by calculation using measured and calculated thermodynamic properties.

TABLE 8

| Component or variable | Column feed | Column overhead (distillate) | Column bottoms |
|---|---|---|---|
| HFC-236ea, mol % | 24.4 | 1 ppm | 99.99 |
| HFC-1225ye, mol % | 51.2 | 67.7 | 68 ppm |
| HF, mol % | 24.4 | 32.3 | trace |
| Temp, ° C. | — | −8.3 | 21.8 |
| Pressure, psi (kPa) | — | 24.7 (170) | 26.7 (184) |

Example 6

This Example shows how HF, HFC-1225ye, HFC-236ea and/or HFC-236cb may be separated using HFC-1225ye as an entrainer. One possible source for such a mixture is in an HFC-236ea and/or HFC-236cb dehydrofluorination process operated with partial conversion. Like HFC-236ea, HFC-236cb forms an azeotrope with HF that does not separate into two liquid phases and that has a higher boiling point than the HF/HFC-1225ye azeotrope.

Referring now to FIG. 3, a stream comprising HF, HFC-1225ye, and at least one of HFC-236ea and HFC-236cb is fed to the $33^{rd}$ stage from the top of a first distillation column containing 40 theoretical stages via stream 10, with the column operated under conditions to approach the low-boiling HF/HFC-1225ye azeotrope, which is removed as distillate via streams 50, 70, and 90. Enough supplemental HFC-1225ye is recycled from the second column bottoms to $12^{th}$ stage from the top of this first column via stream 20 to enable all of the HF to be removed from the HFC-236cb and/or HFC-236ea. The HFC-236cb and/or HFC-236ea are obtained essentially free of HFC-1225ye and HF as the bottoms product from this column via stream 40.

The near HF/HFC-1225ye azeotropic composition in stream 50 is condensed and divided into reflux (80) and distillate (90) streams. Column 30 is operated with a reflux ratio of 9.0. Distillate stream 90 may be fed to a second distillation column 110 via stream 100 as shown and indicated, mixed with distillate streams 150 and 250 from the second and third columns, respectively, and sent to cooler 160 and decanter 180, or be divided between these two destinations. Because of the desire to remove all of the HF overhead in column 30, excess HFC-1225ye would be recycled to column 30, making the composition of streams 50, 70, 80, 90, and 100 lie on the HFC-1225ye-rich side of the azeotrope. Therefore, if distillate stream 90 is sent via stream 100 to a second distillation column, it should be sent to the column which produces purified HFC-1225ye as the bottoms product.

For this example, distillate stream 90 via stream 260 is mixed with distillate streams 150 and 250 from the second and third columns, respectively, and sent to cooler 160, forming sub-cooled stream 170, which is fed to decanter 180. In the decanter, stream 170 separates into HFC-1225ye-rich and HF-rich liquid fractions, which are removed as streams 190 and 200. The HFC-1225ye-rich stream from the decanter is fed via stream 190 to a second distillation column 110 containing 19 theoretical stages and operated under conditions to approach the HFC-1225ye/HF azeotrope, which is distilled overhead as distillate stream 130, condensed in condenser 140, and mixed with the distillates from the first and third columns via stream 150. Column 110 produces a bottoms stream of HFC-1225ye essentially free of HF via stream 120. Part of the HFC-1225ye bottoms stream 120 is recycled to the first column via stream 20, as previously described, and the rest becomes the purified HFC-1225ye product removed via stream 125. The HF-rich stream from the decanter is fed via stream 200 to a third distillation column 210 containing 9 theoretical stages and operated under conditions to approach the HFC-1225ye/HF azeotrope, which is distilled overhead as distillate as stream 230 which is condensed in condenser 250 and mixed with the distillates from the first and second columns via stream 250. Column 210 produces a bottoms stream of HF essentially free of HFC-1225ye via stream 220.

The data in Table 9 were obtained by calculation using measured and calculated thermodynamic properties.

TABLE 9

| Component or variable | Feed (10) | First btms (40) | First Dist (50) | Second btms (120) | Second Dist (130) | 1225-rich phase (190) | HF-rich phase (200) | Third btms (220) | Third Dist (230) |
|---|---|---|---|---|---|---|---|---|---|
| HF, wt % | 4.03 | 4 ppm | 5.73 | 1 ppm | 7.36 | 1.32 | 40.76 | 100 | 8.52 |
| HFC-236cb, wt % | 71.33 | 99.71 | 1 ppm | 1 ppm | <1 ppm | 1 ppm | <1 ppm | <1 ppm | <1 ppm |
| HFC-1225ye, wt % | 24.64 | 0.29 | 94.27 | 100 | 92.64 | 98.68 | 59.24 | 1 ppm | 91.48 |
| Temp, °C. | 27.7 | 35.8 | 11.8 | 37.1 | 31.6 | −40.0 | −40.0 | 84.9 | 32.2 |
| Pressure, psia | 60.6 | 54.8 | 54.8 | 104.8 | 104.7 | 104.7 | 104.7 | 104.8 | 104.7 |

Example 7

This Example shows one way in which HF may be separated from a fluoroolefin and its dehydrofluorination precursor, for example HFC-1225ye and HFC-236ea and/or HFC-236cb or HFC-1225zc and HFC-236fa, by azeotropic distillation using an added entrainer. Like both HFC-236cb and HFC-236ea, HFC-236fa forms an azeotrope with HF that does not separate into two liquid phases and that has a higher boiling temperature than the HF/HFC-1225zc azeotrope. The composition of feed mixture in this example is such as one might obtain from a dehydrofluorination reactor operated with partial conversion, i.e., it contains equimolar amounts of HF and fluoroolefin.

Referring now to FIG. 4, a stream comprising HF, HFC-1225zc, and HFC-236fa is fed to a first distillation column 110 via stream 100. An entrainer-rich stream is also fed to this column via stream 190. In this example, CFC-115 is used as the entrainer. CFC-115 forms a low-boiling azeotrope with HF that separates into two liquid phases upon condensation and whose boiling temperature is lower than the other azeotropes in the mixture Column 110 contains 34 theoretical stages and is operated under conditions to cause HF to distill overhead with the entrainer due to the influence of the low-boiling HF/CFC-115 azeotrope. Sufficient CFC-115 is fed to this first column via stream 190 such that HFC-1225zc and HFC-236fa may be obtained essentially free of CFC-115 and HF as the bottoms from column 110 via stream 120. The HFC-1225zc and HFC-236fa in stream 120 may then optionally be separated from each other by conventional distillation and the HFC-236fa optionally recycled back to a dehydrofluorination reactor to form HFC-1225zc. The distillate from column 110, removed via stream 130, contains essentially all of the CFC-115 and HF in column feeds 100 and 190 and, optionally, some HFC-236fa and/or HFC-1225zc. This first distillate stream 130 is condensed by condenser 140 to form stream 150, which is then mixed with condensed distillate stream 250 from the second distillation column and, as needed, additional fresh CFC-115 added via stream 260. This combined stream is sub-cooled by cooler 160 and sent via stream 170 to decanter 180 where it separates into separate entrainer-rich and HF-rich liquid fractions which are removed via streams 190 and 200, respectively. The majority of the HFC-236fa and HFC-1225zc present in the decanter partition into the CFC-115-rich phase fraction. The entrainer-rich fraction is fed to the first distillation column 110 via stream 190. The HF-rich fraction from the decanter is fed via stream 200 to a second distillation column 210 containing 8 theoretical stages and operated under conditions such that a bottoms stream of HF essentially free of HFC-236fa, HFC-1225zc, and CFC-115 is produced and removed via stream 220. The distillate from column 210, removed via stream 230 and containing essentially all of the HFC-236fa, HFC-1225zc, and CFC-115 present in the column feed (stream 200) plus the HF not recovered in product stream 220, is condensed by condenser 240 and removed via stream 250. Condensed distillate stream 250 is combined with both the condensed distillate stream 150 from the first column and, as needed, fresh entrainer, added via stream 260, then cooled and fed to the decanter for further separation.

The data in Table 10 were obtained by calculation using measured and calculated thermodynamic properties.

TABLE 10

| Component or variable | Feed (100) | First col btm (120) | First Dist (130) | Entrainer-rich phase (190) | HF-rich phase (200) | Second col btm (220) | Second Dist (230) |
|---|---|---|---|---|---|---|---|
| HFC-236fa, wt % | 57.14 | 60.56 | 11.81 | 12.19 | 6.51 | <1 ppm | 8.05 |
| HFC-1225zc, wt % | 37.22 | 39.44 | 20.30 | 20.95 | 8.63 | <1 ppm | 10.67 |
| HF, wt % | 5.64 | <1 ppm | 4.05 | 0.94 | 66.30 | 100.0 | 58.33 |
| CFC-115, wt % | 0 | 1 ppm | 63.84 | 65.91 | 18.52 | <1 ppm | 22.95 |

TABLE 10-continued

| Component or variable | Feed (100) | First col btm (120) | First Dist (130) | Entrainer-rich phase (190) | HF-rich phase (200) | Second col btm (220) | Second Dist (230) |
|---|---|---|---|---|---|---|---|
| Temp, °C. | 30.0 | 29.2 | 7.1 | −25.0 | −25.0 | 66.7 | 58.2 |
| Pres, psia | 114.7 | 64.8 | 64.7 | 64.7 | 64.7 | 64.7 | 64.7 |

Example 8

This Example shows how an HFC which forms a homogeneous azeotrope with HF can be separated from a mixture comprising HF, the HFC and a fluoroolefin by azeotropic distillation using the fluoroolefin as an entrainer, followed by separation of the fluoroolefin and HF by azeotropic distillation using an added compound as the entrainer. HF and the fluoroolefin are not required to be partially miscible at reduced temperatures for such a separation process to work as long as the HF-fluoroolefin azeotrope has a lower boiling point than the HF-HFC azeotrope. For illustration purposes, the fluoroolefin is HFC-1225ye and the HFC is HFC-236ea and/or HFC-236cb.

Referring now to FIG. 5, a stream comprising HF, HFC-1225ye, and at least one of HFC-236ea and HFC-236cb is fed to a first distillation column 30 via stream 10, with the column operated under conditions to approach the low-boiling HF/HFC-1225ye azeotrope, which is removed as distillate via streams 50, 70, and 100. This first column can be designed and operated in such a way that the near azeotropic distillate is essentially free of HFC-236ea and/or HFC-236cb. By recycling enough supplemental HFC-1225ye from the second column bottoms to the first column via stream 20, essentially all of the HF can be distilled overhead as the HF/HFC-1225ye azeotrope such that HFC-236cb and/or HFC-236ea are obtained essentially free of HFC-1225ye and HF as the bottoms product from column 30 via stream 40. The HFC-236ea and/or HFC-236cb may then optionally be recycled back to a reactor for production of HFC-1225ye, or may be further purified and then recycled. This demonstrates the use of the fluoroolefin as an entrainer to remove HF from an HFC.

As described in Example 6, the distillate from the first column may be fed to a second distillation column, mixed with the distillate streams from a second and third column, cooled, and then sent to a decanter, or split between these two destinations. For this example, the distillate from the first column 30 is fed via stream 100 to a second column 110. An entrainer-rich stream is also fed to this second column via stream 190. Distillation column 110 is operated under conditions such that the distillate, removed via stream 130, contains essentially all of the entrainer and HF in the column feeds 100 and 190 and produces an HFC-1225ye bottoms product essentially free of HF and entrainer which is removed via stream 120. Part of the HFC-1225ye bottoms stream 120 is recycled to the first column via stream 20, as previously described, and the rest becomes the purified HFC-1225ye product removed via stream 125. Distillate stream 130 is condensed by condenser 140 to form stream 150, which is then mixed with the condensed distillate stream 250 from the second distillation column and, as needed, fresh entrainer added via stream 260. This combined stream is cooled by cooler 160 and sent via stream 170 to decanter 180 where it separates into separate entrainer-rich and HF-rich liquid fractions, which are removed via streams 190 and 200, respectively. The majority of the HFC-1225ye present in the decanter partitions into the entrainer-rich phase fraction. The decanter entrainer-rich fraction is fed to column 110 via stream 190. The decanter HF-rich fraction is fed, via stream 200, to a third distillation column (210) operated under conditions which produce a bottoms product consisting of HF essentially free of HFC-1225ye and the entrainer, which is removed via stream 220. The distillate from column 210, which is removed via stream 230 and contains essentially all of the HFC-1225ye and entrainer present in the column feed (stream 200) and any HF not recovered in product stream 220, is condensed by condenser 240, forming stream 250. Condensed distillate stream 250 is combined with both the condensed distillate stream 150 from the second column and, as needed, fresh entrainer, added via stream 260, then cooled and fed to the decanter via stream 170 for further separation.

Example 9

This example shows how an HFC that forms a homogeneous azeotrope with HF and a fluoroolefin that forms an azeotrope with HF and is partially miscible with HF can both be separated from a mixture comprising HF, the HFC and the fluoroolefin by azeotropic distillation using the fluoroolefin as an entrainer as long as the HF-fluoroolefin azeotrope has a lower boiling point than the HF-HFC azeotrope. For illustration purposes, in this example the fluoroolefin is HFC-1225ye, the HFC is HFC-236ea and/or HFC-236cb, and the feed mixture has a composition such as might be obtained from a dehydrofluorination reactor operated with partial conversion, that is, the mixture contains equimolar amounts of HF and the fluoroolefin.

Figure 6:
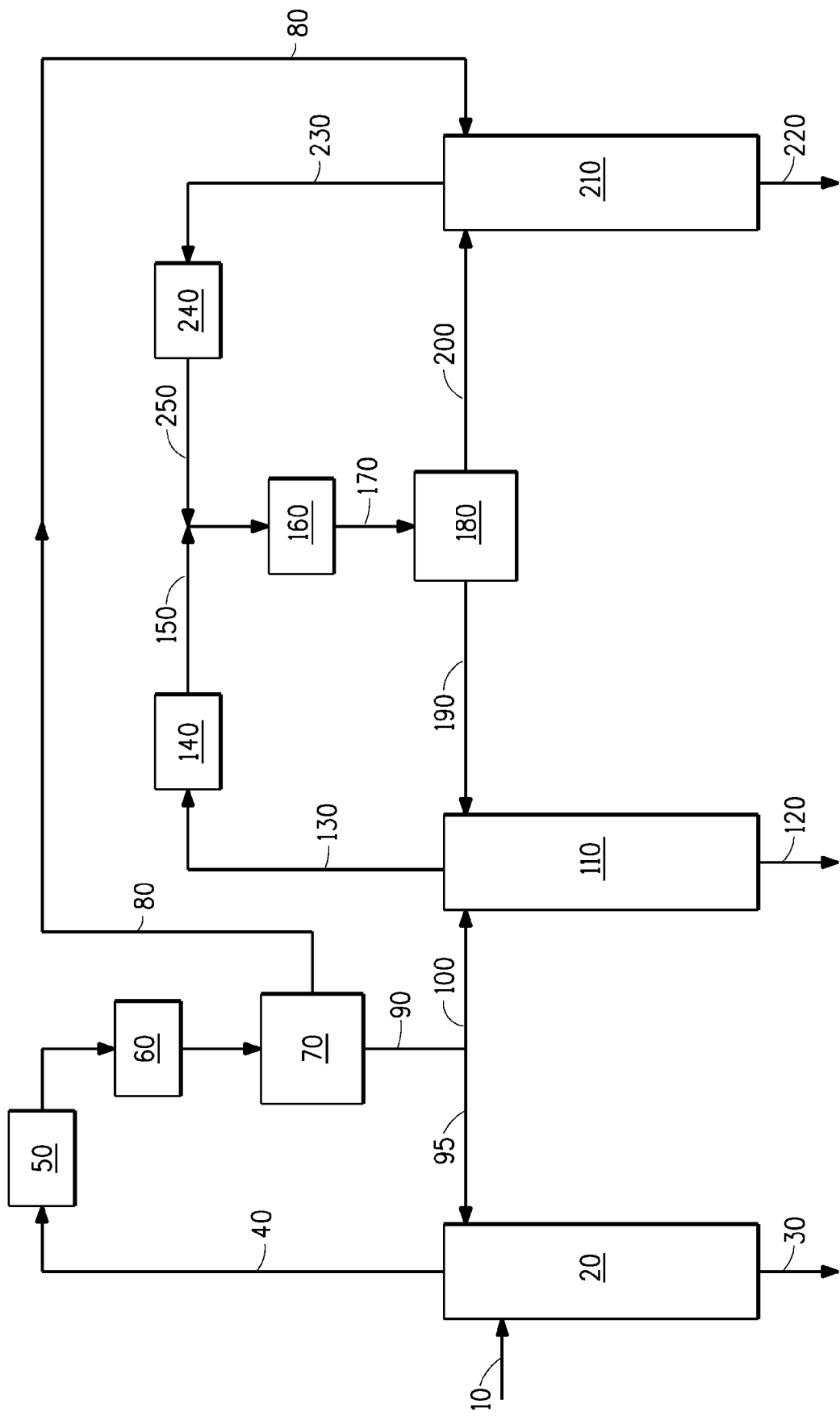
FIG. 6 illustrates another embodiment of the process shown in FIG. 3 wherein the two-phase mixture leaving the condenser of the first column is decanted and separated into HFC-1225ye-rich and HF-rich streams which are fed to the HFC-1225ye and HF columns, respectively.

As in Examples 6 and 8, the HFC-236ea and/or HFC-236cb present are separated from HF and HFC-1225ye by azeotropic distillation in a first distillation column (20) using the HFC-1225ye in the feed mixture as the entrainer. As before, additional HFC-1225ye is needed to distill all of the HF away from the HFC-236ea and/or HFC-236cb. Referring now to FIG. 6, the difference in this example is that a first cooler (60) and a first decanter (70) are added after the first distillation column's condenser (50) such that the distillate separates into HF-rich and HFC-1225ye-rich liquid phase fractions in the decanter, which are removed via streams 80 and 90, respectively. Part of the HFC-1225ye-rich stream (90) is returned to the first column as reflux via stream 95 and the remaining portion is fed to a second distillation column (110) via stream 100 where it is separated into an HFC-1225ye bottoms product, removed via stream 120, that is essentially free of HF and a distillate composition near to the HF/HFC-1225ye azeotrope, removed via stream 130, as described in Example 8. Because the reflux stream (95) is enriched in HFC-1225ye relative to the HFC-1225ye/HF azeotropic composition, the reflux stream (95) supplies the additional HFC-1225ye needed to make the HFC-236ea and/or HFC-236cb bottoms product from the first column, removed via stream 30, essentially free of HF, thereby reducing the amount of purified HFC-1225ye that must be recycled from the second column to the first column. As shown in FIG. 6, at sufficiently high reflux flows, the need for recycling any of the purified HFC-1225ye from the bottom of the second column to the first column can be completely eliminated. The first decanter's HF-rich phase fraction is fed to a third distillation column (210) via stream 80. Both feeds (streams 80 and 200) to the third column have compositions containing excess HF relative to the HF/HFC-1225ye azeotrope so that an HF bottoms product essentially free of HFC-1225ye may be obtained in column 210 and removed via stream 220. The distillate from the third column has a composition near to the HF/HFC-1225ye azeotrope and is removed via stream 230. As in earlier examples, the distillates (streams 130 and 230) from columns 110 and 210 are condensed in condensers 140 and 240, forming streams 150 and 250, respectively, mixed together, and sent first to a second cooler (160) and then to a second decanter (180) where separate HFC-1225ye-rich and HF-rich liquid phase fractions are formed. The HFC-1225ye-rich fraction is removed from decanter 180 via stream 190 and fed to the second column 110 for further separation. The HF-rich fraction is removed from decanter 180 via stream 200 and fed to the third column 210 for further separation.

The data in Table 11 were obtained by calculation using measured and calculated thermodynamic properties.

TABLE 11

| Component of variable | Feed (10) | First btm (30) | First Dist (40) | First HF-rich phase (80) | First 1225ye-rich phase (90) | Sec. Btm (120) | Second Dist (130) | Third btms (220) | Third dist (230) |
|---|---|---|---|---|---|---|---|---|---|
| HF, wt % | 6.41 | <1 ppm | 1.84 | 40.76 | 1.32 | 1 ppm | 4.93 | 100.0 | 8.70 |
| HFC-236cb, wt % | 51.33 | 99.95 | 1 ppm | <1 ppm | 1 ppm | 1 ppm | <1 ppm | <1 ppm | <1 ppm |
| HFC-1225ye, wt % | 42.26 | 0.05 | 98.16 | 59.24 | 98.68 | 100.0 | 95.07 | 1 ppm | 91.30 |
| Temp, °C. | 37.0 | 36.2 | 13.4 | −40.0 | −40.0 | 15.5 | 12.1 | 60.7 | 12.1 |
| Pres, psia | 55.2 | 55.4 | 54.7 | 54.8 | 54.5 | 54.8 | 54.7 | 54.8 | 54.7 |

Example 10

Figure 7:
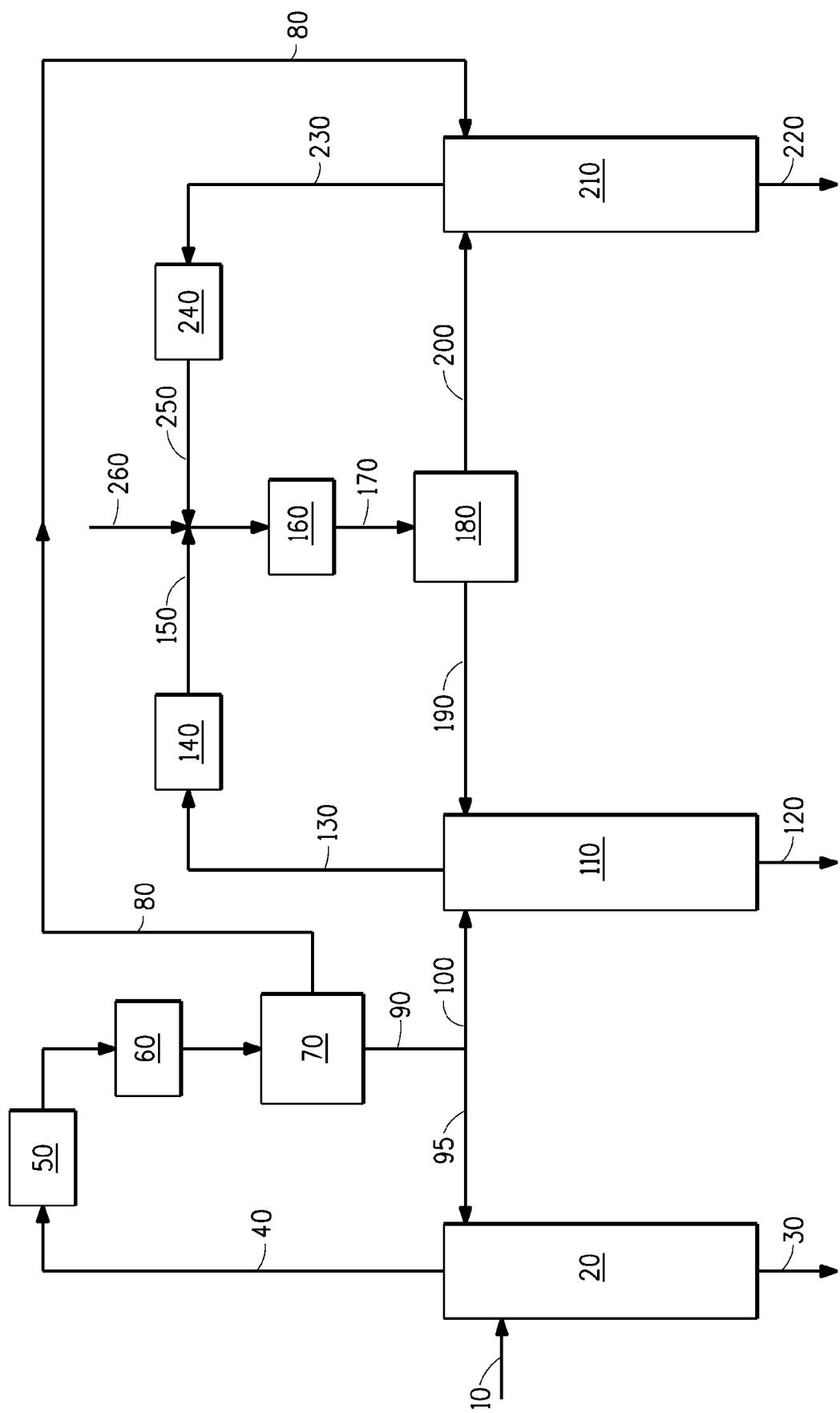
FIG. 7 illustrates another embodiment of the process shown in FIG. 5 wherein the two-phase mixture leaving the condenser of the first column is decanted and separated into HFC-1225ye-rich and HF-rich streams which are fed to the HFC-1225ye and HF columns, respectively.

This example shows how an HFC that forms an azeotrope with HF and a fluoroolefin that is partially miscible with and forms an azeotrope with HF can both be separated from a mixture comprising HF, the HFC and the fluoroolefin by azeotropic distillation. If the HF-fluoroolefin azeotrope has a lower boiling point than the HF-HFC azeotrope, the fluoroolefin can be used as the entrainer to remove the HFC from the mixture. The fluoroolefin and HF can be separated either by using the fluoroolefin as the entrainer, as shown in FIG. 6 and demonstrated in Example 8, or by using an added compound as the entrainer. The latter case is covered by this example. Referring now to FIG. 7, the first distillation column (20), condenser (50), cooler (60), and decanter (70) in this embodiment operates identically to the similarly numbered equipment in Example 10 as just described. The HF-rich and fluoroolefin-rich liquid distillate fractions from the first column's decanter (70) are fed via streams 80 and 100 to distillation columns 210 and 110 which recover purified HF and fluoroolefin, respectively. The remaining portion of the process shown in FIG. 7, i.e., distillation columns 110 and 210, condensers 140 and 240, cooler 160, decanter 180, and all of their associated streams, have the same function and operate similarly to the same numbered equipment shown in FIG. 5 and described in Example 8.

Figure 8:
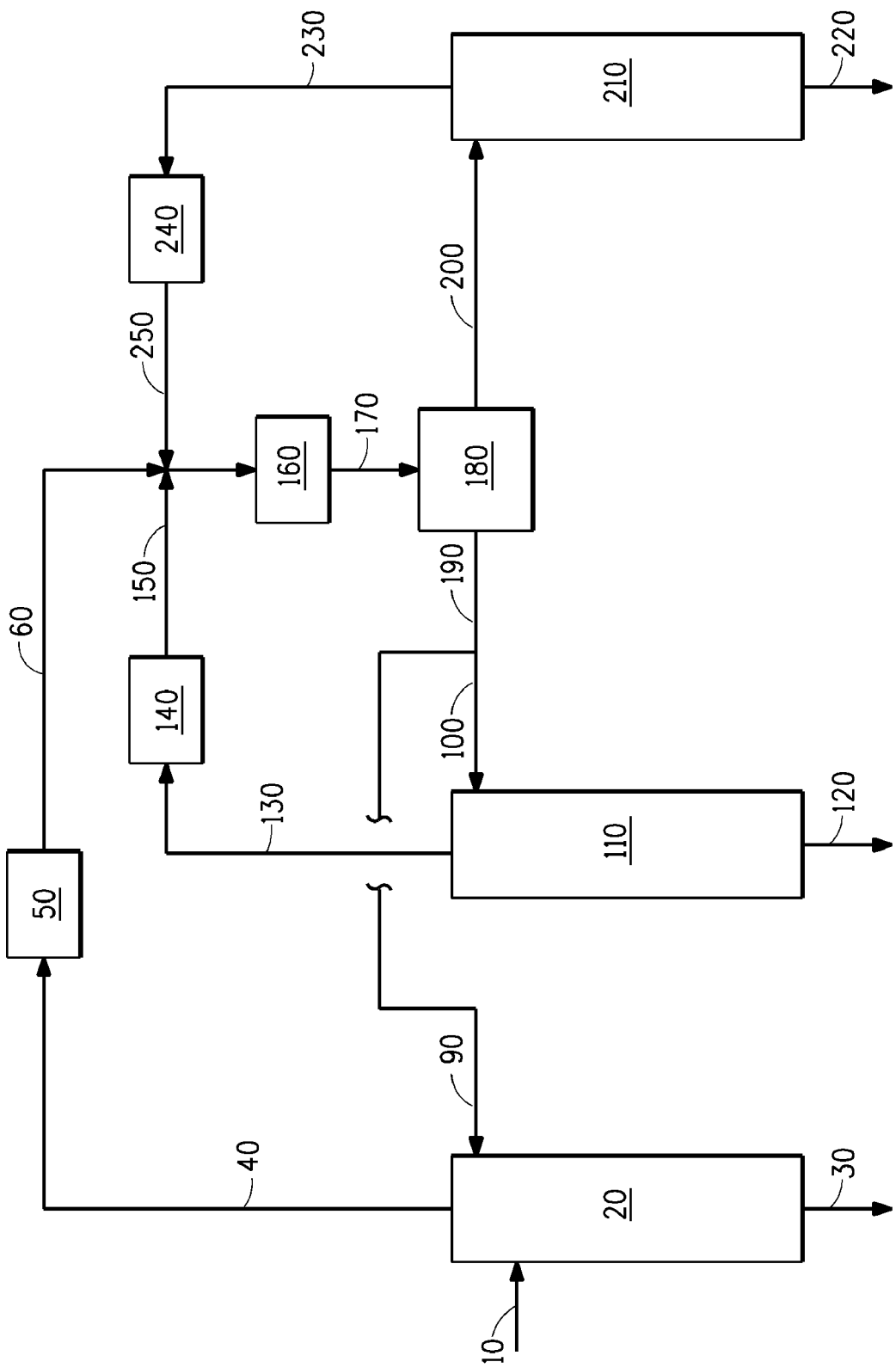
FIG. 8 illustrates another embodiment of the process shown in FIG. 6, wherein the three columns, 20, 110, and 220, share one decanter.

In other embodiments of the invention, (a) condensers 140 and 240 may be combined into a single unit, (b) coolers 60 and 160 can be combined into a single unit and decanters 70 and 180 can be combined into a unit, as shown in FIG. 8, and (c) the three condensers 50, 140 & 240 can be combined into a single unit, coolers 60 and 160 can be combined into a single unit and decanters 70 and 180 can be combined into a unit.

Example 11

Azeotropic Distillation for the Separation of HFC-1429mzy from HF without an Entrainer Example 11 demonstrates that HF may be separated from HFC-1429mzy (1,1,1,3,4,4,5,5,5-nonafluoro-2-pentene) by azeotropic distillation without an added entrainer. HFC-1429mzy and HF form a minimum-boiling azeotrope that prevents their complete separation by ordinary fractional distillation. Referring now to FIG. 1, a composition comprising HF and HFC-1429mzy is fed to a first column 110 via stream 100. This first column contains 7 theoretical stages and is operated under appropriate conditions to approach the low-boiling HF/HFC-1429mzy azeotrope. Because HFC-1429mzy is being fed to this first column in excess of that needed to form the azeotrope with the HF, HFC-1429mzy is recovered as a product stream out the bottoms of the column via stream 120, while a composition near to the HF/HFC-1429mzy azeotrope is recovered as distillate via stream 130. Stream 130 is condensed in 140, mixed with the nearly azeotropic composition recycled from the second column via stream 250 and the combined stream is sub-cooled in cooler 160 and sent to decanter 180 where the combined stream 170 separates into an HFC-1429mzy-rich (190) and an HF-rich (200) streams. Stream 190 is recycled to the top stage of the first column. Stream 200 is fed to the top stage of a second distillation column 210, containing 12 theoretical stages and operated under conditions to approach the HF/HFC-1429mzy azeotrope. Because HF is being fed to this second column in excess of that needed to form the low-boiling HF/HFC-1429mzy azeotrope, HF is recovered as a product stream out the bottoms of the column via stream 220 while a composition close to the HF/HFC-1429mzy azeotrope is recovered as distillate via stream 230. Stream 230 is condensed in 240, mixed with the nearly azeotropic composition from the first column via stream 150 and fed to cooler 160 and then decanter 180.

The data in Table 12 were calculated using measured and calculated thermodynamic properties.

TABLE 12

| Component of variable | First dist. col. feed | First column distillate | First dist. col. bottom (HFC-1429mzy product) | HFC-1429mzy rich phase (from decanter) | HF-rich phase (from decanter) | Second distillate | Second dist. col. Bottom (HF product) |
|---|---|---|---|---|---|---|---|
| Stream No. | 100 | 130 | 120 | 190 | 200 | 230 | 220 |
| HF, wt % | 3.6 | 20.8 | 1 ppm | 4.4 | 65.7 | 23.2 | 100 |
| HFC-1429mzy, wt % | 96.4 | 79.2 | 100 | 95.6 | 34.3 | 76.8 | 1 ppm |
| Temp, ° C. | 30.0 | 49.1 | 75.7 | 40.0 | 40.0 | 48.8 | 66.7 |
| Pres, psia (kPa) | 95 | 65 | 65 | 65 | 65 | 65 | 65 |

Example 12

Azeotropic Distillation for the Separation of PFC-1216 from HF without an Entrainer Example 12 demonstrates that HF may be separated from PFC-1216 (hexafluoropropylene or HFP) by azeotropic distillation without an added entrainer. HF and HFP form a minimum-boiling azeotrope that prevents their complete separation by ordinary fractional distillation. Referring now to FIG. 1, a composition comprising HF and HFP is fed to a first column 110 via stream 100. This first column contains 8 theoretical stages and is operated under appropriate conditions to approach the low-boiling HF/HFP azeotrope. Because HF is being fed to this first column in excess of that needed to form the azeotrope with the HFP, HF is recovered as a product stream out the bottoms of the column via stream 120, while a composition near to the HF/HFP azeotrope is recovered as distillate via stream 130. Stream 130 is condensed in 140, mixed with the nearly azeotropic composition recycled from the second column via stream 250 and the combined stream is sub-cooled in cooler 160 and sent to decanter 180 where the combined stream 170 separates into separate HF-rich 190 and HFP-rich 200 streams. Stream 190 is recycled to the top stage of the first column. Stream 200 is fed to the top stage of a second distillation column 210, containing 26 theoretical stages and operated under conditions to approach the HF/HFP azeotrope. Because HFP is being fed to this second column in excess of that needed to form the low-boiling HF/HFP azeotrope, HFP is recovered as a product stream out the bottoms of the column via stream 220 while a composition close to the HF/HFP azeotrope is recovered as distillate via stream 230. Stream 230 is condensed in 240, mixed with the nearly azeotropic composition from the first column via stream 150 and fed to cooler 160 and then decanter 180.

The data in Table 13 were calculated using measured and calculated thermodynamic properties.

TABLE 13

| Component or variable | First dist. col. feed | First column distillate | First dist. col. bottom (HF product) | HF rich phase (from decanter) | HFP-rich phase (from decanter) | Second distillate | Second dist. col. Bottom (HFP product) |
|---|---|---|---|---|---|---|---|
| Stream No. | 100 | 130 | 120 | 190 | 200 | 230 | 220 |
| HF, wt % | 8.2 | 7.1 | 100 | 52.7 | 1.3 | 7.0 | 1 ppm |
| HFP, wt % | 91.8 | 92.9 | 10 ppm | 47.3 | 98.7 | 93.0 | 100 |
| Temp, ° C. | 30.0 | 27.4 | 88.6 | −25 | −25.0 | 27.2 | 32.7 |
| Pres, psia (kPa) | 165 | 115 | 115 | 115 | 115 | 115 | 115 |

Example 13

Azeotropic Distillation for the Separation of HFC-1225zc and HF Using CFC-115 as the Entrainer Example 13 demonstrates that HF and a fluoroolefin that form an azeotrope may be separated into essentially pure components by azeotropic distillation without requiring that the HF and the fluoroolefin be partially miscible. For illustration purposes, HFC-1225zc is used as the fluoroolefin in this example and CFC-115 is used as the azeotropic distillation entrainer. The CFC-115, HFC-1225zc, HF ternary mixture contains two minimum-boiling binary azeotropes between HF and HFC-1225zc and between HF and CFC-115 with the HF/CFC-115 azeotrope having the lower boiling point. In addition, HF and CFC-115 are only partially miscible.

Referring now to FIG. 2, a composition consisting of HF and HFC-1225zc is fed to a first column 110 containing 8 theoretical stages via stream 100. An HF-rich and CFC-115-lean mixture is also fed to the top stage of column 110 via stream 190. Because the combined amount of HF in streams 100 and 190 is in excess of that needed to form the low-boiling HF/HFC-1225zc azeotrope, column 110 is operated under conditions to recover the "excess" HF as a bottoms product essentially free of both HFC-1225zc and CFC-115, which is removed via stream 120, and to produce a distillate with a composition close to the HF/HFC-1225zc azeotrope, which is removed via stream 130. Stream 130 is condensed in condenser 140, forming stream 150, and mixed with both the condensed distillate stream 250 from a second distillation column and, as needed, fresh CFC-115 added via stream 260. Combined streams 150, 250, and 260 are sent first to cooler 160 and then to decanter 180 where the sub-cooled liquid stream 170 separates into HF-rich and CFC-1,5-rich liquid phase fractions which are removed via streams 190 and 200, respectively. The HFC-1225zc present in the decanter primarily distributes into the CFC-115-rich liquid phase fraction. HF-rich stream 190 is recycled to the first column as previously described. The HF-lean liquid phase fraction in the decanter is fed to the top stage of a second distillation column 210 containing 34 theoretical stages via stream 200. Because the concentration of HF in stream 200 is small enough for the composition of stream 200 to lie on the organic side of the HF/HFC-1225zc and HF/CFC-115 azeotropes and the distillation boundary running between the two azeotropes, HFC-1225zc essentially free of both HF and CFC-115 can be recovered as the bottoms product from column 210 via stream 220. A ternary composition enriched in CFC-115 and depleted in HFC-1225zc relative to stream 200 is removed from the top of column 210 as the distillate via stream 230. In the extreme, the composition of distillate 230 can approach the composition of the HF/CFC-115 azeotrope. Stream 230 is condensed in condenser 240, forming stream 250, and then combined with streams 150 and 260 as previously described.

The data in Table 14 were calculated using measured and calculated thermodynamic properties

TABLE 14

| Component or variable | Feed (100) | First btms (120) | First dist (130) | HF-rich phase (190) | Entrainer-rich phase (200) | Second btms (220) | Second dist (230) |
|---|---|---|---|---|---|---|---|
| HFC-1225zc, wt % | 86.84 | 10 ppm | 90.51 | 26.37 | 60.86 | 100.0 | 45.72 |
| HF, wt % | 13.16 | 100.0 | 7.96 | 61.75 | 1.09 | <1 ppm | 1.52 |
| CFC-115, wt % | 0.0 | <1 ppm | 1.53 | 11.89 | 38.05 | 1 ppm | 52.76 |
| Temp, ° C. | 30.0 | 66.6 | 14.9 | −25.0 | −25.0 | 18.2 | 7.1 |
| Pres, psia | 114.7 | 64.7 | 64.7 | 64.7 | 64.7 | 64.8 | 64.7 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A process for separating a mixture comprising HF and fluoroolefin, said process comprising:
    a. feeding the composition comprising HF and fluoroolefin to a first distillation column;
    b. removing an azeotrope composition comprising HF and fluoroolefin as a first distillate and either i) HF or ii) fluoroolefin as a first column bottoms composition;
    c. condensing the first distillate to form 2 liquid phases, being i) an HF-rich phase and ii) a fluoroolefin-rich phase and separating said 2 liquid phases in a decanter; and
    d. recycling a first liquid phase enriched in the same compound that is removed as the first column bottoms, said first liquid phase being either i) HF-rich phase or ii) fluoroolefin-rich phase, back to the first distillation column.

2. The process of claim 1, further comprising feeding a second liquid phase not recycled in step (d), said second liquid phase being either i) HF-rich phase or ii) fluoroolefin-rich phase, to a second distillation column, and recovering the compound not recovered in step (b) as the first column bottoms composition as the second column bottoms composition.

3. The process of claim 1, wherein said fluoroolefin is selected from the group consisting of:
    (i) fluoroolefins of the formula E- or Z—$R^1CH=CHR^2$, wherein $R^1$ and $R^2$ are, independently, $C_1$ to $C_6$ perfluoroalkyl groups;
    (ii) cyclic fluoroolefins of the formula cyclo-[CX=CY(CZW)$_n$-], wherein X, Y, Z, and W, independently, are H or F, and n is an integer from 2 to 5; and
    (iii) fluoroolefins selected from the group consisting of:
    tetrafluoroethylene ($CF_2=CF_2$); hexafluoropropene ($CF_3CF=CF_2$); 1,2,3,3,3-pentafluoro-1-propene (CHF=$CFCF_3$), 1,1,3,3,3-pentafluoro-1-propene ($CF_2=CHCF_3$), 1,1,2,3,3-pentafluoro-1-propene ($CF_2=CFCHF_2$), 1,2,3,3-tetrafluoro-1-propene (CHF=$CFCHF_2$), 2,3,3,3-tetrafluoro-1-propene ($CH_2$=CFCF$_3$), 1,3,3,3-tetrafluoro-1-propene (CHF=CHCF$_3$), 1,1,2,3-tetrafluoro-1-propene (CF$_2$=CFCH$_2$F), 1,1,3,3-tetrafluoro-1-propene (CF$_2$=CHCHF$_2$), 1,2,3,3-tetrafluoro-1-propene (CHF=CFCHF$_2$), 3,3,3-trifluoro-1-propene (CH$_2$=CHCF$_3$), 2,3,3-trifluoro-1-propene (CHF$_2$CF=CH$_2$); 1,1,2-trifluoro-1-propene (CH$_3$CF=CF$_2$); 1,2,3-trifluoro-1-propene (CH$_2$FCF=CF$_2$); 1,1,3-trifluoro-1-propene (CH$_2$FCH=CF$_2$); 1,3,3-trifluoro-1-propene (CHF$_2$CH=CHF); 1,1,1,2,3,4,4,4-octafluoro-2-butene (CF$_3$CF=CFCF$_3$); 1,1,2,3,3,4,4,4-octafluoro-1-butene (CF$_3$CF$_2$CF=CF$_2$); 1,1,1,2,4,4,4-heptafluoro-2-butene (CF$_3$CF=CHCF$_3$); 1,2,3,3,4,4,4-heptafluoro-1-butene (CHF=CFCF$_2$CF$_3$); 1,1,1,2,3,4,4-heptafluoro-2-butene (CHF$_2$CF=CFCF$_3$); 1,3,3,3-tetrafluoro-2-(trifluoromethyl)-1-propene ((CF$_3$)$_2$C=CHF); 1,1,3,3,4,4,4-heptafluoro-1-butene (CF$_2$=CHCF$_2$CF$_3$); 1,1,2,3,4,4,4-heptafluoro-1-butene (CF$_2$=CFCHFCF$_3$); 1,1,2,3,3,4,4-heptafluoro-1-butene (CF$_2$=CFCF$_2$CHF$_2$); 2,3,3,4,4,4-hexafluoro-1-butene (CF$_3$CF$_2$CF=CH$_2$); 1,3,3,4,4,4-hexafluoro-1-butene (CHF=CHCF$_2$CF$_3$); 1,2,3,4,4,4-hexafluoro-1-butene (CHF=CFCHFCF$_3$); 1,2,3,3,4,4-hexafluoro-1-butene (CHF=CFCF$_2$CHF$_2$); 1,1,2,3,4,4-hexafluoro-2-butene (CHF$_2$CF=CFCHF$_2$); 1,1,1,2,3,4-hexafluoro-2-butene (CH$_2$FCF=CFCF$_3$); 1,1,1,2,4,4-hexafluoro-2-butene (CH$_2$FCH=CFCF$_3$); 1,1,1,3,4,4-hexafluoro-2-butene (CF$_3$CH=CFCHF$_2$); 1,1,2,3,3,4-hexafluoro-1-butene (CF$_2$=CFCF$_2$CH$_2$F); 1,1,2,3,4,4-hexafluoro-1-butene (CF$_2$=CFCHFCHF$_2$); 3,3,3-trifluoro-2-(trifluoromethyl)-1-propene (CH$_2$=C(CF$_3$)$_2$); 1,1,1,2,4-pentafluoro-2-butene (CH$_2$FCH=CFCF$_3$); 1,1,1,3,4-pentafluoro-2-butene (CF$_3$CH=CFCH$_2$F); 3,3,4,4,4-pentafluoro-1-butene (CF$_3$CF$_2$CH=CH$_2$); 1,1,1,4,4-pentafluoro-2-butene (CHF$_2$CH=CHCF$_3$); 1,1,1,2,3-pentafluoro-2-butene (CH$_3$CF=CFCF$_3$); 2,3,3,4,4-pentafluoro-1-butene (CH$_2$=CFCF$_2$CHF$_2$); 1,1,2,4,4-pentafluoro-2-butene (CHF$_2$CF=CHCHF$_2$); 1,1,2,3,3-pentafluoro-1-butene (CH$_3$CF$_2$CF=CF$_2$); 1,1,2,3,4-pentafluoro-2-butene (CH$_2$FCF=CFCHF$_2$); 1,1,3,3,3-pentafluoro-2-methyl-1-propene (CF$_2$=C(CF$_3$)(CH$_3$)); 2-(difluoromethyl)-3,3,3-trifluoro-1-propene (CH$_2$=C(CHF$_2$)(CF$_3$)); 2,3,4,4,4-pentafluoro-1-butene (CH$_2$=CFCHFCF$_3$); 1,2,4,4,4-pentafluoro-1-butene (CHF=CFCH$_2$CF$_3$); 1,3,4,4,4-pentafluoro-1-butene (CHF=CHCHFCF$_3$); 1,3,3,4,4-pentafluoro-1-butene (CHF=CHCF$_2$CHF$_2$); 1,2,3,4,4-pentafluoro-1-butene (CHF=CFCHFCHF$_2$); 3,3,4,4-tetrafluoro-1-butene (CH$_2$=CHCF$_2$CHF$_2$); 1,1-difluoro-2-(difluoromethyl)-1-propene (CF$_2$=C(CHF$_2$)(CH$_3$)); 1,3,3,3-tetrafluoro-2-methyl-1-propene (CHF=C(CF$_3$)(CH$_3$)); 3,3-difluoro-2-(difluoromethyl)-1-propene (CH$_2$=C(CHF$_2$)$_2$); 1,1,1,2-tetrafluoro-2-butene (CF$_3$CF=CHCH$_3$); 1,1,1,3-tetrafluoro-2-butene (CH$_3$CF=CHCF$_3$); 1,1,1,2,3,4,4,5,5,5-decafluoro-2-pentene (CF$_3$CF=CFCF$_2$CF$_3$); 1,1,2,3,3,4,4,5,5,5-decafluoro-1-pentene (CF$_2$=CFCF$_2$CF$_2$CF$_3$); 1,1,1,4,4,4-hexafluoro-2-(trifluoromethyl)-2-butene ((CF$_3$)$_2$C=CHCF$_3$); 1,1,1,2,4,4,5,5,5-nonafluoro-2-pentene (CF$_3$CF=CHCF$_2$CF$_3$); 1,1,1,3,4,4,5,5,5-nonafluoro-2-pentene (CF$_3$CH=CFCF$_2$CF$_3$); 1,2,3,3,4,4,5,5,5-nonafluoro-1-pentene (CHF=CFCF$_2$CF$_2$CF$_3$); 1,1,3,3,4,4,5,5,5-nonafluoro-1-pentene (CF$_2$=CHCF$_2$CF$_2$CF$_3$); 1,1,2,3,3,4,4,5,5-nonafluoro-1-pentene (CF$_2$=CFCF$_2$CF$_2$CHF$_2$); 1,1,2,3,4,4,5,5,5-nonafluoro-2-pentene (CHF$_2$CF=CFCF$_2$CF$_3$); 1,1,1,2,3,4,4,5,5-nonafluoro-2-pentene (CF$_3$CF=CFCF$_2$CHF$_2$); 1,1,1,2,3,4,5,5,5-nonafluoro-2-pentene (CF$_3$CF=CFCHFCF$_3$); 1,2,3,4,4,4-hexafluoro-3-(trifluoromethyl)-1-butene (CHF=CFCF(CF$_3$)$_2$); 1,1,2,4,4,4-hexafluoro-3-(trifluoromethyl)-1-butene (CF$_2$=CFCH(CF$_3$)$_2$); 1,1,1,4,4,4-hexafluoro-2-(trifluoromethyl)-2-butene (CF$_3$CH=C(CF$_3$)$_2$); 1,1,3,4,4,4-hexafluoro-3-(trifluoromethyl)-1-butene (CF$_2$=CHCF(CF$_3$)$_2$); 2,3,3,4,4,5,5,5-octafluoro-1-pentene (CH$_2$=CFCF$_2$CF$_2$CF$_3$); 1,2,3,3,4,4,5,5-octafluoro-1-pentene (CHF=CFCF$_2$CF$_2$CHF$_2$); 3,3,4,4,4-pentafluoro-2-(trifluoromethyl)-1-butene (CH$_2$=C(CF$_3$)CF$_2$CF$_3$); 1,1,4,4,4-pentafluoro-3-(trifluoromethyl)-1-butene (CF$_2$=CHCH(CF$_3$)$_2$); 1,3,4,4,4-pentafluoro-3-(trifluoromethyl)-1-butene (CHF=CHCF(CF$_3$)$_2$); 1,1,4,4,4-pentafluoro-2-(trifluoromethyl)-1-butene (CF$_2$=C(CF$_3$)CH$_2$CF$_3$); 3,4,4,4-tetrafluoro-3-(trifluoromethyl)-1-butene ((CF$_3$)$_2$CFCH=CH$_2$); 3,3,4,4,5,5,5-heptafluoro-1-pentene (CF$_3$CF$_2$CF$_2$CH=CH$_2$); 2,3,3,4,4,5,5-heptafluoro-1-pentene (CH$_2$=CFCF$_2$CF$_2$CHF$_2$); 1,1,3,3,5,5,5-heptafluoro-1-butene (CF$_2$=CHCF$_2$CH$_2$CF$_3$); 1,1,1,2,4,4,4-heptafluoro-3-methyl-2-butene (CF$_3$CF=C(CF$_3$)(CH$_3$)); 2,4,4,4-tetrafluoro-3-(trifluoromethyl)-1-butene (CH$_2$=CFCH(CF$_3$)$_2$); 1,4,4,4-tetrafluoro-3-(trifluoromethyl)-1-butene (CHF=CHCH(CF$_3$)$_2$); 1,1,1,4-tetrafluoro-2-(trifluoromethyl)-2-butene (CH$_2$FCH=C(CF$_3$)$_2$); 1,1,1,3-tetrafluoro-2-(trifluoromethyl)-2-butene (CH$_3$CF=C(CF$_3$)$_2$); 1,1,1-trifluoro-2-(trifluoromethyl)-2-butene ((CF$_3$)$_2$C=CHCH$_3$); 3,4,4,5,5,5-hexafluoro-2-pentene (CF$_3$CF$_2$CF=CHCH$_3$); 1,1,1,4,4,4-hexafluoro-2-methyl-2-butene (CF$_3$C(CH$_3$)=CHCF$_3$); 3,3,4,5,5,5-hexafluoro-1-pentene (CH$_2$=CHCF$_2$CHFCF$_3$); 4,4,4-trifluoro-2-(trifluoromethyl)-1-butene (CH$_2$=C(CF$_3$)CH$_2$CF$_3$); 1,1,2,3,3,4,4,5,5,6,6,6-dodecafluoro-1-hexene (CF$_3$(CF$_2$)$_3$CF=CF$_2$); 1,1,1,2,2,3,4,5,5,6,6,6-dodecafluoro-3-hexene (CF$_3$CF$_2$CF=CFCF$_2$CF$_3$); 1,1,1,4,4,4-hexafluoro-2,3-bis(trifluoromethyl)-2-butene ((CF$_3$)$_2$C=C(CF$_3$)$_2$); 1,1,1,2,3,4,5,5,5-nonafluoro-4-(trifluoromethyl)-2-pentene ((CF$_3$)$_2$CFCF=CFCF$_3$); 1,1,1,4,4,5,5,5-octafluoro-2-(trifluoromethyl)-2-pentene ((CF$_3$)$_2$C=CHC$_2$F$_5$); 1,1,1,3,4,5,5,5-octafluoro-4-(trifluoromethyl)-2-pentene ((CF$_3$)$_2$CFCF=CHCF$_3$); 3,3,4,4,5,5,6,6,6-nonafluoro-1-hexene (CF$_3$CF$_2$CF$_2$CF$_2$CH=CH$_2$); 4,4,4-trifluoro-3,3-bis(trifluoromethyl)-1-butene (CH$_2$=CHC(CF$_3$)$_3$); 1,1,1,4,4,4-hexafluoro-3-methyl-2-(trifluoromethyl)-2-butene ((CF$_3$)$_2$C=C(CH$_3$)(CF$_3$)); 2,3,3,5,5,5-hexafluoro-4-(trifluoromethyl)-1-pentene (CH$_2$=CFCF$_2$CH(CF$_3$)$_2$); 1,1,1,2,4,4,5,5,5-nonafluoro-3-methyl-2-pentene (CF$_3$CF=C(CH$_3$)CF$_2$CF$_3$); 1,1,1,5,5,5-hexafluoro-4-(trifluoromethyl)-2-pentene (CF$_3$CH=CHCH(CF$_3$)$_2$); 3,4,4,5,5,6,6,6-octafluoro-2-hexene (CF$_3$CF$_2$CF$_2$CF=CHCH$_3$); 3,3,4,4,5,5,6,6-octafluoro1-hexene (CH$_2$=CHCF$_2$CF$_2$CF$_2$CHF$_2$); 1,1,1,4,4-pentafluoro-2-(trifluoromethyl)-2-pentene ((CF$_3$)$_2$C=CHCF$_2$CH$_3$); 4,4,5,5,5-pentafluoro-2-(trifluoromethyl)-1-pentene (CH$_2$=C(CF$_3$)CH$_2$C$_2$F$_5$); 3,3,4,4,5,5,5-heptafluoro-2-methyl-1- pentene (CF$_3$CF$_2$CF$_2$C(CH$_3$)=CH$_2$); 4,4,5,5,6,6,6-heptafluoro-2-hexene (CF$_3$CF$_2$CF$_2$CH=CHCH$_3$); 4,4,5,5,6,6,6-heptafluoro-1-hexene (CH$_2$=CHCH$_2$CF$_2$C$_2$F$_5$); 1,1,1,2,2,3,4-heptafluoro-3-hexene (CF$_3$CF$_2$CF=CFC$_2$H$_5$); 4,5,5,5-tetrafluoro-4-(trifluoromethyl)-1-pentene (CH$_2$=CHCH$_2$CF(CF$_3$)$_2$); 1,1,1,2,5,5,5-heptafluoro-4-methyl-2-pentene (CF$_3$CF=CHCH(CF$_3$)(CH$_3$)); 1,1,1,3-tetrafluoro-2-(trifluoromethyl)-2-pentene ((CF$_3$)$_2$C=CFC$_2$H$_5$); 1,1,1,2,3,4,4,5,5,6,6,7,7,7-tetradecafluoro-2-heptene (CF$_3$CF=CFCF$_2$CF$_2$C$_2$F$_5$); 1,1,1,2,2,3,4,5,5,6,6,7,7,7-tetradecafluoro-3-heptene (CF$_3$CF$_2$CF=CFCF$_2$C$_2$F$_5$); 1,1,1,3,4,4,5,5,6,6,7,7,7-tridecafluoro-2-heptene (CF$_3$CH=CFCF$_2$CF$_2$C$_2$F$_5$); 1,1,1,2,4,4,5,5,6,6,7,7,7-tridecafluoro-2-heptene (CF$_3$CF=CHCF$_2$CF$_2$C$_2$F$_5$); 1,1,1,2,2,4,5,5,6,6,7,7,7-tridecafluoro-3-heptene (CF$_3$CF$_2$CH=CFCF$_2$C$_2$F$_5$); and 1,1,1,2,2,3,5,5,6,6,7,7,7-tridecafluoro-3-heptene (CF$_3$CF$_2$CF=CHCF$_2$C$_2$F$_5$).

4. The process of claim 3 wherein said fluoroolefin comprises at least one compound selected from the group consisting of HFC-1225ye, HFC-1234ze, HFC-1234yf, and HFC-1243zf.

5. The process of claim 1, wherein said fluoroolefin is present in a concentration greater than the azeotrope composition for hydrogen fluoride and said fluoroolefin, and wherein the first column bottoms composition is fluoroolefin essentially free of hydrogen fluoride, and wherein said first liquid phase is enriched in fluoroolefin.

6. The process of claim 5 further comprising:
   i. feeding the hydrogen fluoride-rich phase from the decanter to a second distillation column, and
   ii. recovering hydrogen fluoride essentially free of fluoroolefin from the bottom of the second distillation column.

7. The process of claim 6, further comprising recycling a second distillate composition to the two liquid phases in the decanter.

8. The process of claim 1, wherein hydrogen fluoride is present in a concentration greater than the azeotrope concentration for hydrogen fluoride and said fluoroolefin, and wherein the first column bottoms composition is hydrogen fluoride essentially free of fluoroolefin, and wherein said first liquid phase is enriched in hydrogen fluoride.

9. The process of claim 8 further comprising:
   i. feeding the fluoroolefin-rich phase from the decanter to a second distillation column, and
   ii. recovering fluoroolefin essentially free of hydrogen fluoride from the bottom of the second distillation column.

10. The process of claim 9, further comprising recycling a second distillate composition to the two liquid phases in the decanter.

11. The process of claim 3, wherein said fluoroolefin is selected from the group consisting of:
1,1,1,4,4,4-hexafluorobut-2-ene; 1,1,1,4,4,5,5,5-octafluoropent-2-ene; 1,1,1,4,4,5,5,6,6,6-decafluorohex-2-ene; 1,1,1,4,5,5,5-heptafluoro-4-(trifluoromethyl)pent-2-ene; 1,1,1,2,2,5,5,6,6,6-decafluorohex-3-ene; 1,1,1,4,4,5,5,6,6,7,7,7-dodecafluorohept-2-ene; 1,1,1,4,4,5,6,6,6-nonafluoro-5-(trifluoromethyl)hex-2-ene; 1,1,1,4,5,5,6,6,6-nonfluoro-4-(trifluoromethyl)hex-2-ene; 1,1,1,5,5,5-hexafluoro-4,4-bis(trifluoromethyl)pent-2-ene; 1,1,1,2,2,5,5,6,6,7,7,7-dodecafluorohept-3-ene; 1,1,1,2,2,5,6,6,6-nonafluoro-5-(trifluoromethyl)hex-3-ene; 1,1,1,4,4,5,5,6,6,7,7,8,8,8-tetradecafluorooct-2-ene; 1,1,1,4,4,5,5,6,7,7,7-undecafluoro-6-(trifluoromethyl)hept-2-ene; 1,1,1,5,5,6,6,6-octafluoro-4,4-bis(trifluoromethyl)hex-2-ene; 1,1,1,2,2,5,5,6,6,7,7,8,8,8-tetradecafluorooct-3-ene; 1,1,1,2,2,5,5,6,7,7,7-undecafluoro-6-(trifluoromethyl)hept-3-ene; 1,1,1,2,2,5,6,6,7,7,7-undecafluoro-5-(trifluoromethyl)hept-3-ene; 1,1,1,2,2,6,6,6-octafluoro-5,5-bis(trifluoromethyl)hex-3-ene; 1,1,1,2,2,3,3,6,6,7,7,8,8,8-tetradecafluorooct-4-ene; 1,1,1,2,5,6,6,6-octafluoro-2,5-bis(trifluoromethyl)hex-3-ene; 1,1,1,2,5,5,6,6,7,7,7-undecafluoro-2-(trifluoromethyl)hept-3-ene; 1,1,1,4,4,5,5,6,6,7,7,8,8,9,9,9-hexadecafluoronon-2-ene; 1,1,1,4,5,5,6,6,7,7,8,8,8-tridecafluoro-4-(trifluoromethyl)hept-2-ene; 1,1,1,6,6,6-octafluoro-4,4-bis(trifluoromethyl)hept-2-ene; 1,1,1,2,2,5,5,6,6,7,7,8,8,9,9,9-hexadecafluoronon-3-ene; 1,1,1,2,2,5,5,6,6,7,8,8,8-tridecafluoro-7-(trifluoromethyl)oct-3-ene; 1,1,1,2,2,6,6,7,7,7-decafluoro-5,5-bis(trifluoromethyl)hept-3-ene; 1,1,1,2,2,3,3,6,6,7,7,8,8,9,9,9-hexadecafluoronon-4-ene; 1,1,1,2,2,3,3,6,6,7,8,8,8-tridecafluoro-7-(trifluoromethyl)oct-4-ene; 1,1,1,2,2,3,3,6,7,7,8,8,8-tridecafluoro-6-(trifluoromethyl)oct-4-ene; 1,1,1,5,5,6,6,7,7,7-decafluoro-2,2-bis(trifluoromethyl)hept-3-ene; 1,1,1,2,5,5,6,6,7,7,8,8,8-tridecafluoro-2(trifluoromethyl)oct-3-ene; 1,1,1,2,5,5,6,7,7,7-decafluoro-2,6-bis(trifluoromethyl)hept-3-ene; 1,1,1,2,5,6,6,7,7,7-decafluoro-2,5-bis(trifluoromethyl)hept-3-ene; 1,1,1,2,6,6,6-heptafluoro-2,5,5-tris(trifluoromethyl)hex-3-ene; 1,1,1,2,2,5,5,6,6,7,7,8,8,9,9,10,10,10-octadecafluorodec-3-ene; 1,1,1,2,2,5,6,6,7,7,8,8,9,9,9-pentadecafluoro-5-(trifluoromethyl)non-3-ene; 1,1,1,2,2,6,6,7,7,8,8,8-dodecafluoro-5,5-bis(trifluoromethyl)oct-3-ene; 1,1,1,2,2,3,3,6,6,7,7,8,8,9,9,10,10,10-octadecafluorodec-4-ene; 1,1,1,2,2,3,3,6,6,7,7,8,9,9,9-pentadecafluoro-8-(trifluoromethyl)non-4-ene; 1,1,1,2,2,3,3,7,7,8,8-dodecafluoro-6,6-bis(trifluoromethyl)oct-4-ene; 1,1,1,2,5,5,6,6,7,7,8,8,9,9,9-pentadecafluoro-2-(trifluoromethyl)non-3-ene; 1,1,1,2,5,5,6,6,7,8,8,8-dodecafluoro-2,7-bis(trifluoromethyl)oct-3-ene; 1,1,1,2,6,6,7,7,7-nonafluoro-2,5,5-tris(trifluoromethyl)hept-3-ene; 1,1,1,2,2,3,3,4,4,7,7,8,8,9,9,10,10,10-octadecafluorodec-5-ene; 1,1,1,2,3,3,6,6,7,7,8,8,9,9,9-pentadecafluoro-2-(trifluoromethyl)non-4-ene; 1,1,1,2,2,3,6,6,7,7,8,9,9,9-pentadecafluoro-3-(trifluoromethyl)non-4-ene; 1,1,1,5,5,6,6,7,7,8,8,8-dodecafluoro-2,2,-bis(trifluoromethyl)oct-3-ene; 1,1,1,2,3,3,6,6,7,8,8,8-dodecafluoro-2,7-bis(trifluoromethyl)oct-4-ene; 1,1,1,2,3,3,6,7,7,8,8,8-dodecafluoro-2,6-bis(trifluoromethyl)oct-4-ene; 1,1,1,5,5,6,7,7,7-nonafluoro-2,2,6-tris(trifluoromethyl)hept-3-ene; 1,1,1,2,2,3,6,7,7,8,8,8-dodecafluoro-3,6-bis(trifluoromethyl)oct-4-ene; 1,1,1,2,2,3,6,7,7,8,8,8-dodecafluoro-3,6-bis(trifluoromethyl)oct-4-ene; 1,1,1,5,6,6,7,7,7-nonafluoro-2,2,5-tris(trifluoromethyl)hept-3-ene; and 1,1,1,6,6,6-hexafluoro-2,2,5,5-tetrakis(trifluoromethyl)hex-3-ene.

12. The composition of claim 3, wherein said fluoroolefin is selected from the group consisting of:
1,2,3,3,4,4-hexafluorocyclobutene; 3,3,4,4-tetrafluorocyclobutene; 3,3,4,4,5,5,-hexafluorocyclopentene; 1,2,3,3,4,4,5,5-octafluorocyclopentene; and 1,2,3,3,4,4,5,5,6,6-decafluorocyclohexene.

* * * * *